US006964739B2

(12) United States Patent
Boyd et al.

(10) Patent No.: US 6,964,739 B2
(45) Date of Patent: Nov. 15, 2005

(54) DEVICE AND METHOD FOR GENERATING AND APPLYING OZONATED WATER

(75) Inventors: Brian T. Boyd, Fort Collins, CO (US); Brian R. Williams, Fort Collins, CO (US); Michael J. Quinn, Windsor, CO (US); Harold A. Luettgen, Windsor, CO (US)

(73) Assignee: Tersano Inc., Windsor (CA)

( * ) Notice: Subject to any disclaimer, the term of this patent is extended or adjusted under 35 U.S.C. 154(b) by 265 days.

(21) Appl. No.: 10/022,137

(22) Filed: Dec. 12, 2001

(65) Prior Publication Data

US 2002/0185423 A1 Dec. 12, 2002

Related U.S. Application Data

(60) Provisional application No. 60/261,534, filed on Jan. 12, 2001, provisional application No. 60/254,820, filed on Dec. 12, 2000, and provisional application No. 60/261,101, filed on Jan. 10, 2001.

(51) Int. Cl.$^7$ .................................................. C02F 1/78
(52) U.S. Cl. ...................... 210/167; 210/192; 210/194; 210/205
(58) Field of Search ................................ 210/167, 192, 210/194, 198.1, 205

(56) References Cited

U.S. PATENT DOCUMENTS

| | | | |
|---|---|---|---|
| 1,975,424 A | 10/1934 | John | ............................ 204/32 |
| 1,975,426 A | 10/1934 | John | ............................ 204/32 |
| 2,212,109 A | 8/1940 | Abraham | ........................ 62/89 |
| 2,334,377 A | 11/1943 | Bennett | ........................ 204/312 |
| 2,925,371 A | 2/1960 | Van Winckel et al. | |
| 3,126,302 A | 3/1964 | Drushella | |
| 3,195,719 A | 7/1965 | Giesler | .......................... 206/47 |
| 3,401,858 A | 9/1968 | White et al. | .................... 224/48 |
| 3,421,836 A | 1/1969 | Sundin et al. | ................... 21/53 |
| 3,495,699 A | 2/1970 | Giesler | ..................... 206/45.14 |
| 3,600,740 A | 8/1971 | Ogier | ............................ 15/257 |
| 3,617,385 A | 11/1971 | Gray | |
| 3,717,505 A | 2/1973 | Unkle et al. | |
| 3,742,301 A | 6/1973 | Burris | ............................ 317/4 |
| 3,823,728 A | 7/1974 | Burris | .......................... 137/88 |
| 3,846,176 A | 11/1974 | Kuhl | |
| 4,019,986 A | 4/1977 | Burris et al. | ................. 210/139 |

(Continued)

FOREIGN PATENT DOCUMENTS

| | | |
|---|---|---|
| DE | 40 16 157 A1 | 12/1990 |
| DE | 196 53 034 A1 | 7/1998 |
| DE | 198 23 880 A1 | 12/1998 |

(Continued)

OTHER PUBLICATIONS

Pallav Tatapudi and James M. Fenton, "Simultaneous Synthesis of Ozone and Hydrogen Peroxide in a Proton–Exchange–Membrane Electrochemical Reactor," May 1994, pp. 1174–1178.

(Continued)

Primary Examiner—Betsey Morrison Hoey
(74) Attorney, Agent, or Firm—Borden Ladner Gervais LLP; Curtis B. Behmann

(57) ABSTRACT

The present invention is a device and method for ozonating water and applying the ozonated water to surfaces for cleaning purposes. The instant invention allows a user to transform water into a liquid with more robust cleaning properties conveniently and in a short time. The present invention includes a cleaning apparatus having a reservoir containing water, the reservoir able to be easily manipulated by a user to dispense the water, a device for increasing the level of oxidative properties in the water, and a circulation flow path communicating with the reservoir and the device to allow at least some of the water in the reservoir to flow from the reservoir to the device and back to the reservoir.

17 Claims, 38 Drawing Sheets

U.S. PATENT DOCUMENTS

| | | |
|---|---|---|
| 4,078,987 A | 3/1978 | Specht |
| 4,214,969 A | 7/1980 | Lawrance ................. 204/255 |
| 4,219,035 A | 8/1980 | Deconinck ................ 132/84 D |
| 4,224,129 A | 9/1980 | McIntyre et al. ........... 204/263 |
| 4,316,782 A | 2/1982 | Foller et al. ................ 205/626 |
| 4,375,395 A | 3/1983 | Foller et al. ................ 205/626 |
| 4,416,747 A | 11/1983 | Menth et al. |
| 4,417,969 A | 11/1983 | Ezzell et al. ................ 204/252 |
| 4,500,401 A | 2/1985 | Clark et al. |
| D280,077 S | 8/1985 | Lemaire ..................... D9/372 |
| 4,541,989 A | 9/1985 | Foller .................... 422/186.07 |
| 4,555,335 A | 11/1985 | Burris ....................... 210/192 |
| 4,596,648 A | 6/1986 | Sweeney ................... 204/237 |
| D287,936 S | 1/1987 | Mills et al. .................. D9/372 |
| 4,684,585 A | 8/1987 | Tamminen ................. 429/69 |
| 4,720,334 A | 1/1988 | DuBois et al. |
| 4,732,274 A | 3/1988 | Bouton ...................... 206/561 |
| 4,759,847 A | 7/1988 | Medbury |
| 4,759,849 A | 7/1988 | Baumann et al. |
| 4,792,407 A | 12/1988 | Zeff et al. ................... 210/748 |
| 4,801,375 A | 1/1989 | Padilla ....................... 210/100 |
| 4,836,929 A | 6/1989 | Baumann et al. |
| 4,849,376 A | 7/1989 | Balzan et al. ............... 438/582 |
| 4,876,115 A | 10/1989 | Raistrick ................... 427/115 |
| 4,904,289 A | 2/1990 | Miyakami et al. ............ 62/157 |
| 4,927,800 A | 5/1990 | Nishiki et al. .............. 502/349 |
| 4,950,371 A | 8/1990 | McElroy .................... 205/628 |
| D311,863 S | 11/1990 | Vola ........................... D9/370 |
| 4,978,438 A | 12/1990 | Shimamune et al. |
| 4,992,126 A | 2/1991 | Door .......................... 156/182 |
| 5,083,442 A | 1/1992 | Vlock |
| 5,087,426 A | 2/1992 | Inoue et al. ................. 422/123 |
| 5,094,734 A | 3/1992 | Torrado |
| 5,097,556 A | 3/1992 | Engel et al. |
| 5,114,549 A | 5/1992 | Shimamune et al. |
| 5,121,612 A | 6/1992 | Guay et al. |
| 5,135,645 A | 8/1992 | Sklenak et al. |
| 5,141,618 A | 8/1992 | Cabaraux et al. ........... 204/257 |
| 5,145,350 A | 9/1992 | Dawson et al. ......... 422/186.15 |
| 5,154,807 A | 10/1992 | Harvey ...................... 204/131 |
| 5,154,895 A | 10/1992 | Moon .................... 422/186.07 |
| 5,158,454 A | 10/1992 | Viebahn et al. |
| D330,758 S | 11/1992 | Muderlak .................. D23/366 |
| 5,187,025 A | 2/1993 | Kelland et al. ............... 429/33 |
| 5,236,595 A | 8/1993 | Wang et al. |
| 5,242,764 A | 9/1993 | Dhar ............................ 429/30 |
| 5,246,792 A | 9/1993 | Watanabe .................... 429/33 |
| 5,250,370 A | 10/1993 | Faris ........................... 429/68 |
| 5,266,215 A | 11/1993 | Engelhard |
| 5,290,406 A | 3/1994 | Sawamoto et al. ......... 205/626 |
| 5,315,845 A | 5/1994 | Lee |
| 5,316,740 A | 5/1994 | Baker et al. ............ 422/186.07 |
| 5,316,741 A | 5/1994 | Sewell et al. .......... 422/186.21 |
| 5,372,689 A | 12/1994 | Carlson et al. |
| 5,385,711 A | 1/1995 | Baker et al. ............ 422/186.07 |
| 5,427,658 A | 6/1995 | Allen ......................... 205/556 |
| 5,433,866 A | 7/1995 | Hoppe et al. |
| 5,447,636 A | 9/1995 | Banerjee |
| 5,460,705 A | 10/1995 | Murphy et al. |
| 5,464,480 A | 11/1995 | Matthews |
| 5,498,347 A | 3/1996 | Richard |
| 5,505,856 A | 4/1996 | Campen et al. |
| 5,512,384 A | 4/1996 | Celeste et al. ................ 429/51 |
| 5,529,683 A | 6/1996 | Critz et al. ................. 205/350 |
| 5,536,592 A | 7/1996 | Celeste et al. ............... 429/68 |
| 5,542,264 A | 8/1996 | Hortin et al. |
| 5,547,551 A | 8/1996 | Bahar et al. |
| 5,547,584 A | 8/1996 | Capechart |
| 5,578,280 A | 11/1996 | Kazi et al. ............. 422/186.07 |
| 5,578,388 A | 11/1996 | Faita et al. ................... 429/30 |
| 5,582,717 A | 12/1996 | Di Santo |
| 5,589,052 A | 12/1996 | Shimamune et al. ........ 205/349 |
| 5,593,598 A | 1/1997 | McGinness et al. |
| 5,607,562 A | 3/1997 | Shimamune et al. ........ 204/265 |
| 5,614,332 A | 3/1997 | Pavelle et al. ................ 429/68 |
| 5,618,492 A | 4/1997 | Auten et al. |
| 5,626,769 A | 5/1997 | Sawamoto |
| D380,822 S | 7/1997 | Decker et al. ............. D23/366 |
| 5,653,877 A | 8/1997 | Mark |
| 5,654,109 A | 8/1997 | Plowman et al. |
| 5,656,246 A | 8/1997 | Patapoff et al. |
| 5,682,671 A | 11/1997 | Lund et al. |
| 5,683,576 A | 11/1997 | Olsen |
| 5,686,051 A | 11/1997 | Shiota et al. ........... 422/186.14 |
| 5,707,518 A | 1/1998 | Coates et al. |
| 5,711,887 A | 1/1998 | Gastman et al. |
| 5,712,061 A | 1/1998 | Spak et al. ................. 429/208 |
| 5,715,699 A | 2/1998 | Coates |
| 5,720,869 A | 2/1998 | Yamanaka et al. |
| 5,736,016 A | 4/1998 | Allen ......................... 204/237 |
| 5,741,416 A | 4/1998 | Tempest, Jr. |
| 5,746,954 A | 5/1998 | Aikman, Jr. |
| 5,753,100 A | 5/1998 | Lumsden |
| 5,756,228 A | 5/1998 | Roseanou .................... 429/68 |
| 5,759,970 A | 6/1998 | Prevost et al. |
| 5,766,453 A | 6/1998 | Morellato et al. |
| 5,766,488 A | 6/1998 | Uban et al. |
| 5,768,905 A | 6/1998 | Oh |
| 5,770,033 A | 6/1998 | Murphy et al. ............. 205/464 |
| 5,779,865 A | 7/1998 | Schulze et al. ............. 204/252 |
| 5,785,864 A | 7/1998 | Teran et al. |
| 5,787,537 A | 8/1998 | Mannillo |
| 5,788,930 A | 8/1998 | McMurray .................. 422/121 |
| 5,806,120 A | 9/1998 | McEachern |
| 5,813,245 A | 9/1998 | Coates et al. |
| 5,824,243 A | 10/1998 | Contreras .................. 261/36.1 |
| 5,824,274 A | 10/1998 | Long |
| 5,858,283 A | 1/1999 | Burris ...................... 261/122.1 |
| 5,946,919 A | 9/1999 | McKinney et al. ........... 62/3.7 |
| 5,958,619 A | 9/1999 | Celeste et al. |
| 5,972,196 A | 10/1999 | Murphy et al. ............. 205/466 |
| 5,989,407 A | 11/1999 | Andrews et al. |
| 5,993,618 A * | 11/1999 | Schulze et al. |
| 5,997,702 A | 12/1999 | Koganezawa et al. |
| 6,042,958 A | 3/2000 | Denton et al. |
| 6,057,054 A | 5/2000 | Barton et al. |
| 6,074,551 A | 6/2000 | Jones et al. |
| 6,110,333 A | 8/2000 | Spethmann et al. |
| 6,120,822 A | 9/2000 | Denvir et al. ............... 426/320 |
| 6,200,618 B1 | 3/2001 | Smith et al. |
| 6,206,260 B1 | 3/2001 | Covell et al. ............... 224/539 |
| 6,287,431 B1 | 9/2001 | Murphy et al. ............. 204/258 |
| 6,299,998 B1 | 10/2001 | Morris et al. |
| 6,309,521 B1 | 10/2001 | Andrews et al. |
| D453,373 S | 2/2002 | Drake et al. ............... D23/366 |
| D456,246 S | 4/2002 | Drake et al. ................. D9/337 |
| 6,365,026 B1 | 4/2002 | Andrews et al. |
| 6,368,740 B1 | 4/2002 | Dristy ......................... 429/35 |
| 6,423,439 B1 | 7/2002 | Barton et al. |
| 6,458,257 B1 | 10/2002 | Andrews et al. |
| 6,461,487 B1 | 10/2002 | Andrews et al. ............ 204/262 |
| 6,551,474 B1 | 4/2003 | Andrews et al. |
| 6,551,490 B2 | 4/2003 | Andrews et al. |
| 6,576,096 B1 | 6/2003 | Andrews et al. ............ 204/262 |
| 6,596,427 B1 | 7/2003 | Wozniczka et al. |
| 6,649,097 B2 | 11/2003 | Sasaki et al. ............... 264/102 |
| 6,770,396 B2 | 8/2004 | Hatoh et al. |
| 2002/0070123 A1 | 6/2002 | Andrews et al. |
| 2002/0130036 A1 | 9/2002 | Andrews et al. |
| 2002/0134674 A1 | 9/2002 | Andrews et al. ............ 204/242 |
| 2002/0139690 A1 | 10/2002 | Kanaya et al. |

| | | | |
|---|---|---|---|
| 2002/0164702 | A1 | 11/2002 | Valenzuela et al. |
| 2002/0185423 | A1 | 12/2002 | Boyd et al. .................. 210/167 |
| 2003/0029734 | A1 | 2/2003 | Andrews et al. ............ 205/626 |
| 2003/0080467 | A1 | 5/2003 | Andrews et al. |
| 2003/0209447 | A1 | 11/2003 | Andrews et al. |
| 2003/0235530 | A1 | 12/2003 | Cisar et al. |

FOREIGN PATENT DOCUMENTS

| | | |
|---|---|---|
| DE | 198 05 142 A | 8/1999 |
| EP | 0 048 559 A2 | 3/1982 |
| EP | 0 342 169 A2 | 11/1989 |
| EP | 0 711 731 A2 | 5/1996 |
| EP | 0 711 731 A3 | 2/1997 |
| EP | 0 822 271 A2 | 7/1997 |
| EP | 0 822 271 A3 | 4/1998 |
| EP | 0 884 794 A1 | 12/1998 |
| EP | 1 009 051 A2 | 6/2000 |
| EP | 1 038 993 A | 9/2000 |
| EP | 1 038 993 A1 | 9/2000 |
| EP | 1 149 054 | 10/2001 |
| FR | 2 041 731 A | 2/1971 |
| GB | 2 326 017 A | 12/1998 |
| JP | 60-074359 A | 4/1985 |
| JP | 01-183071 A | 7/1989 |
| JP | 05029001 A | 2/1993 |
| JP | 05109415 A | 4/1993 |
| JP | 2002-532236 A | 10/2002 |
| WO | WO 90/14312 | 11/1990 |
| WO | WO 94/07802 | 4/1994 |
| WO | WO 95/16730 | 6/1995 |
| WO | WO 97/25369 | 7/1997 |
| WO | WO 97/41168 | 11/1997 |
| WO | WO 98/33221 A | 7/1998 |
| WO | WO 98/42617 | 10/1998 |
| WO | WO 99/04446 | 1/1999 |
| WO | WO 00/35813 | 6/2000 |
| WO | WO 01/61074 | 2/2001 |
| WO | WO 01/35755 A1 | 5/2001 |
| WO | WO 02/48431 | 6/2002 |
| WO | WO 03/062494 | 7/2003 |

OTHER PUBLICATIONS

Pallav Tatapudi and James M. Fenton, "Synthesis of Hydrogen Peroxide in a Proton Exchange Membrane Electrochemical Reactor," Apr. 1993, pp. L55–L57.

Pallav Tatapudi and James M. Fenton, "Paired Synthesis of Ozone and Hydrogen Peroxide in An Electrochemical Reactor," pp. 275–285.

Pallav Tatapudi and James M. Fenton, "Synthesis of Ozone in a Proton Exchange Membrane Electrochemical Reactor," Dec. 1993, pp. 3527–3530.

Tom D. Rogers, G. Duncan Hitchens, Carlos E. Salinas, and Oliver J. Murphy, "Water Purification, Microbiological Control, Sterilization and Organic Waste Decomposition Using an Electrochemical Advanced Ozonation Process," Jul. 13–16, 1996, 10 pages.

G. Duncan Hitchens and Oliver J. Murphy, "Development of Proton–Exchange Membrane Electrochemical Reclaimed Water Post–Treatment System," Jul. 15–18, 1991, pp. 131–140.

Masahiro Watanabe, Yasutaka Satah, and Chiyoka Shimura, "Management of the Water Content in Polymer Electrolyte Membranes with Porous Fiber Wicks," Nov. 1993, pp. 3190–3193.

U.S. Appl. No. 09/981,670, filed Oct. 17, 2001, Andrews et al.

U.S. Appl. No. 10/262,558, filed Sep. 30, 2002, Andrews et al.

U.S. Appl. No. 10/079,722, filed Feb. 19, 2002, Andrews et al.

U.S. Appl. No. 09/926,344, filed Oct. 17, 2001, Kanaya et al.

U.S. Appl. No. 10/016,283, filed Nov. 30, 2001, Valenzuela et al.

U.S. Appl. No. 10/392,231, filed Mar. 19, 2003, Andrews et al.

M. Pourbaix, N. De Zoubov, C. Vanleugenhaghe & P. Van Rysselberghe, Lead 1, Section 17.5, Atlas of Electrochemical Equilibria, pp. 485–492 (1974).

http://www.quickpure.com, Alab, LLC website (last visited Nov. 26, 1999).

* cited by examiner

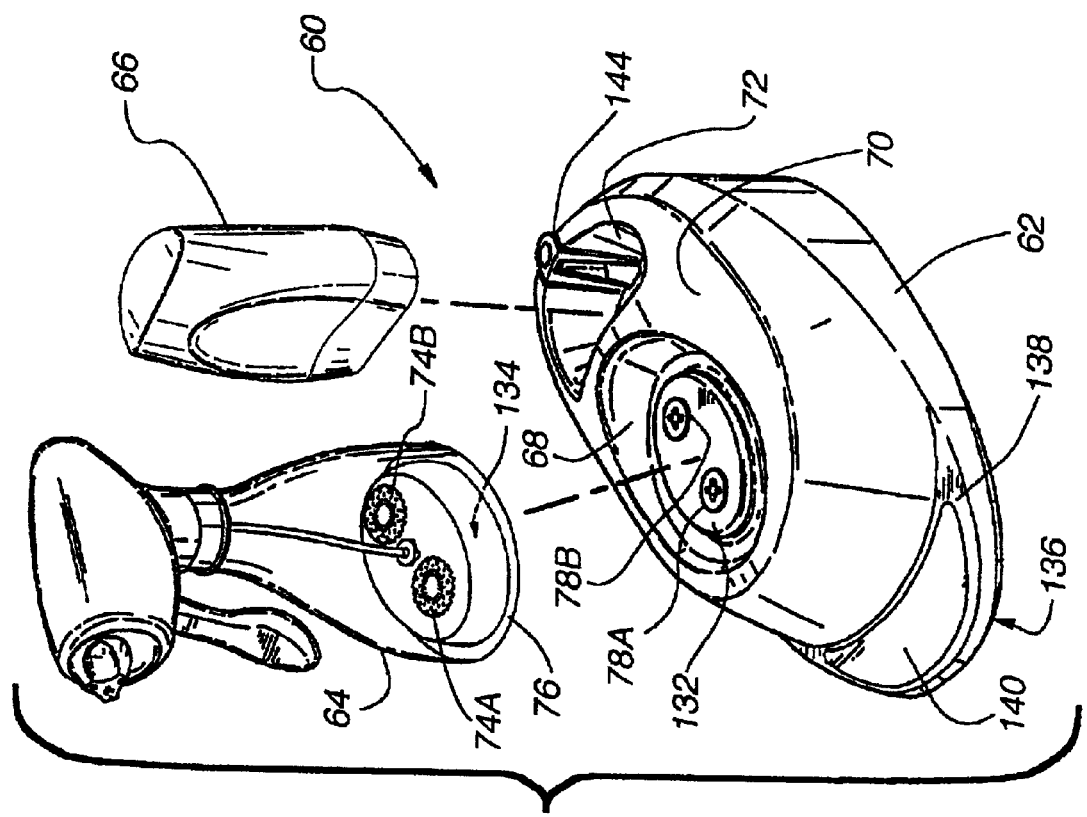
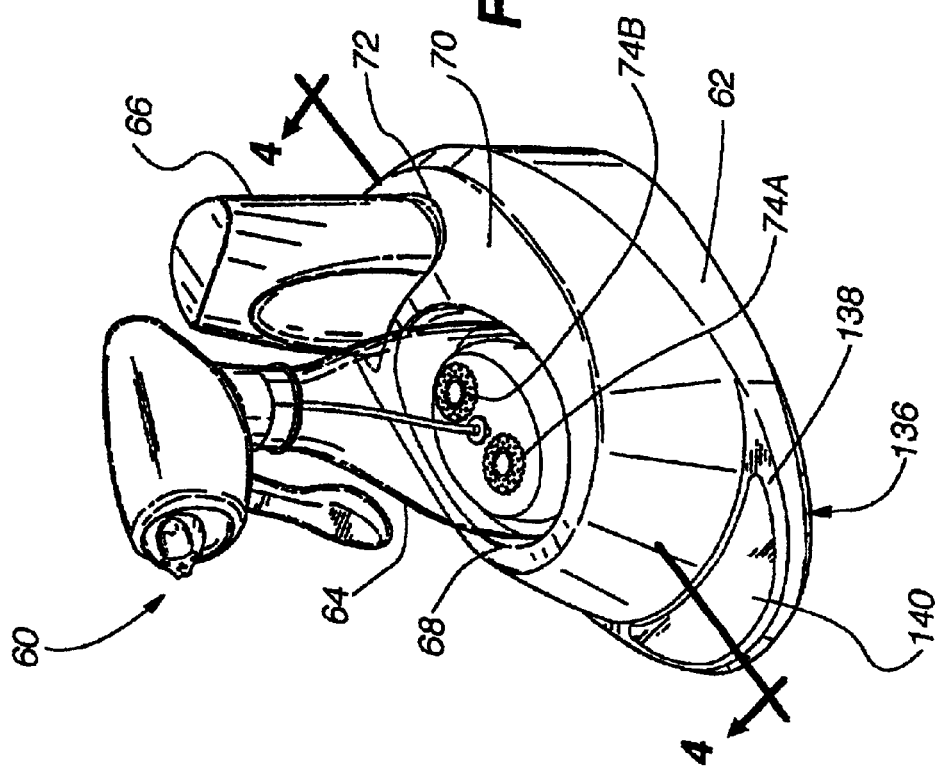

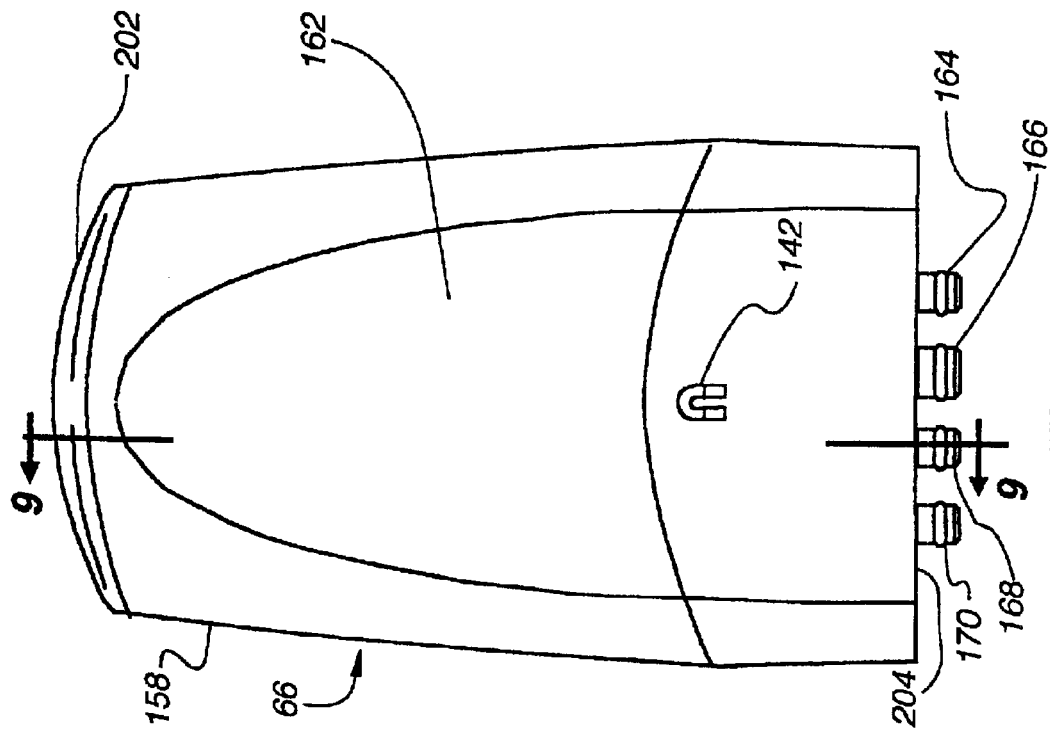
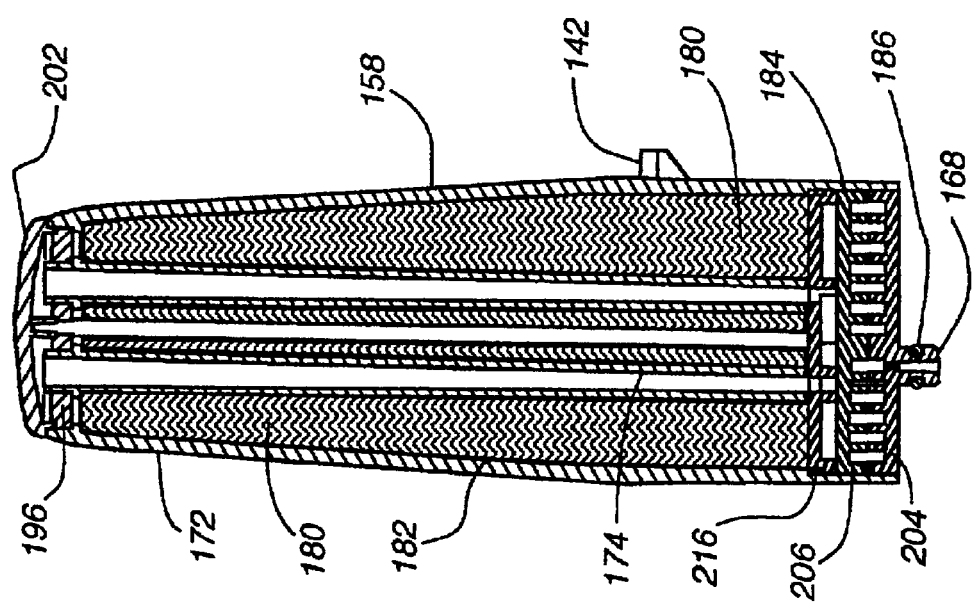

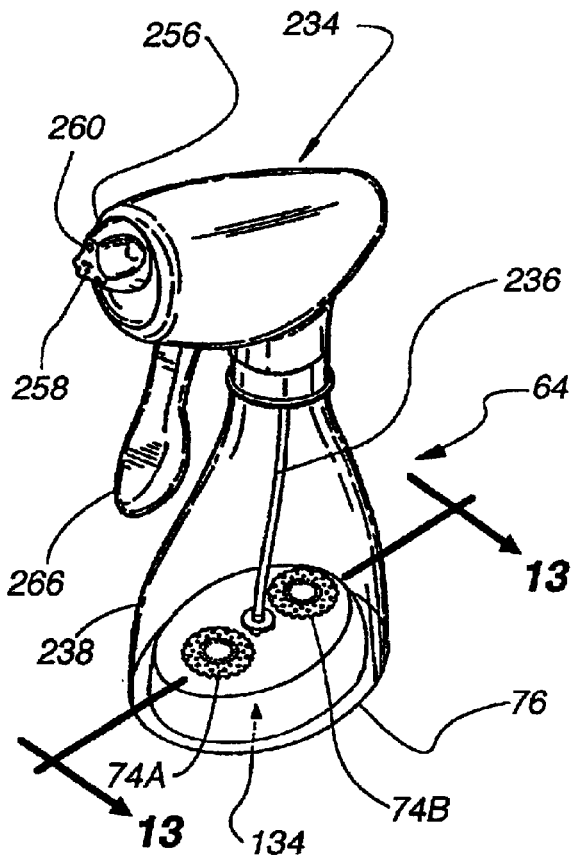
Fig. 11
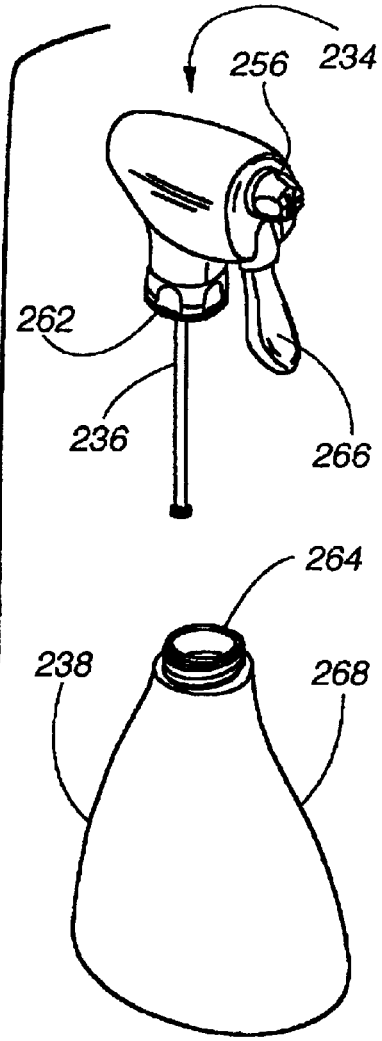
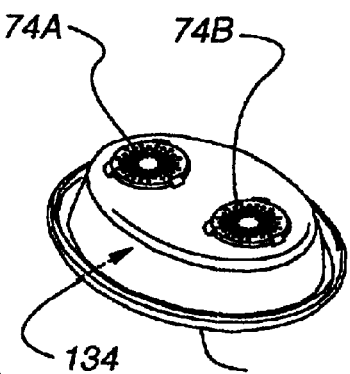
Fig. 12

DEVICE AND METHOD FOR GENERATING AND APPLYING OZONATED WATER

CROSS-REFERENCE TO RELATED APPLICATIONS

This application claims priority to and the benefit of Provisional Patent Application No. 60/261,534, filed Jan. 12, 2001, Provisional Patent Application No. 60/254,820, filed Dec. 12, 2000, and Provisional Patent Application No. 60/261,101, filed Jan. 10, 2001, which are each hereby incorporated by reference in their entirety as if fully disclosed herein.

FIELD OF THE INVENTION

This invention relates to a system and device for producing and applying a cleaning liquid, such as ozonated water. More generally, this invention relates to a device for treating a first liquid to form a second liquid modified from the first liquid, and having additional cleaning qualities. More specifically, this invention relates to a device that ozonates water for use in cleansing and/or disinfecting food or surfaces.

BACKGROUND OF THE INVENTION

The benefits of ozonated water are well known in the art, as are processes for generating ozonated water. Municipal water companies have used ozone technology to treat large quantities of water for many years because of its effectiveness in purifying and conditioning water. Ozone technology has been found to treat water in various ways: by killing bacteria on contact faster than most other conventional treatments; by killing viruses on contact; by killing algae spores, fungus, mold and yeast spores; by removing excess iron, manganese, and sulfur by a process known as microflocculation, thus conditioning the water naturally without chemical additives; and by removing color and odor.

The use of ozonated water leaves no residue; increases plant growth and plant life (due to the high oxygen content in ozonated water); acts as a more effective cleaning agent to produce cleaner clothes; has a better flavor and odor than tap water; and vegetables treated with ozonated water are cleaner and experience a greater shelf-life.

Most known ozone treatment systems for residential use involve complex ozone generators and must be plumbed into the home's water supply system. Such systems are costly, require disruption of a home's water service for an extended period of time, and take a significant period of time to install. In addition, such systems are not mobile and cannot be removed from a home for use in another location without considerable expense to both remove the system and re-install the system. To use ozonated water from current ozonation systems for household tasks such as cleaning surfaces or foods, typically a user must transfer the water to a container such as a spray bottle or carafe. Because the level of ozonation decreases rapidly over time, the act of transferring the ozonated water decreases the overall cleaning effectiveness of the water.

There is a need for a system to produce ozonated water that is both inexpensive and easy to install (i.e., does not require a plumber or disruption of water service). There is a need for a system to produce ozonated water that is readily mobile and can be easily transported and used at multiple locations. There is a need for an ozonation system that ozonates water in a container ready for use, such as a spray bottle or carafe, thereby increasing the overall cleaning effectiveness of the ozonated water. There is a need for a countertop ozonation system that includes easily replaceable parts.

It is with these needs in mind that the present invention was developed.

SUMMARY OF THE INVENTION

The present invention is a device and method for ozonating water and applying the ozonated water to surfaces for cleaning purposes. More generally, other liquid media can also be similarly modified to produce liquid media with increased oxidative properties. Additional contemplated applications include the modification of acids to per-acids, such as acetic acid to peracetic acid. Depending on the properties of the liquid media selected, the reaction cell creating the increased oxidative properties may or may not have to be modified accordingly. The instant invention allows a user to transform water, or other liquid such as vinegar, into a liquid with more robust cleaning properties conveniently and in a short time. These additional liquids may have the ability to retain the oxidative properties substantially longer than ozone in water, thus increasing their utility.

The present invention includes a cleaning apparatus having a reservoir containing a liquid, the reservoir able to be easily manipulated by a user to dispense the liquid, a device for increasing the level of oxidative properties in the liquid, and a circulation flow path communicating with the reservoir and the device to allow at least some of the liquid in the reservoir to flow from the reservoir to the device and back to the reservoir.

In another aspect of the invention, the liquid is water; and the device is an ozone cell for dispensing ozone into the water flowing to the device.

Another aspect of the invention is that the device is positioned in a base unit; and the reservoir is selectively connectable to the base unit and the circulation flow path.

A further aspect of the invention is that the circulation flow path includes a recirculation flow path and a treatment flow path, where the treatment flow path directs water from the recirculation flow path to the device and back to the recirculation flow path.

Yet another aspect of the invention is that the treatment flow path includes a de-ionization pre-treatment region upstream of the device and downstream of the diversion of the treatment flow path from the recirculation flow path.

A further aspect of the invention is that the treatment flow path includes a post-treatment region downstream of the device and upstream of the reconvergence of the treatment flow path and the recirculation flow path.

In another embodiment of the invention, it is a residential cleaning apparatus including a base unit including an ozone generator; a reservoir for holding water and for use by a user to selectively dispense water, the reservoir being selectively and fluidically attachable to the base unit; a circulation flow path formed between the reservoir and the base unit, and fluidically and at least in part connecting the reservoir with the ozone generator; and wherein the at least some of the water flows in the circulation flow path between the reservoir and the ozone generator and back to the reservoir, the ozone generator dispensing ozone into the water.

A further aspect of the invention is that the circulation flow path includes a recirculation flow path and a treatment flow path, the recirculation flow path extending between the reservoir, the base, and back to the reservoir, and the treatment flow path extending from the recirculation flow path to the ozone generator and back to the recirculation flow path; and wherein the ozone generator dispenses ozone into the water in the treatment flow path.

Another aspect of the invention is that the treatment flow path includes a deionization filter media positioned upstream of the ozone generator.

A further aspect of the invention is that the deionization filter media is positioned in the base unit.

Yet another aspect of the invention is includes a cartridge selectively and fluidically connectable to the base unit, and forming part of the treatment flow path; and wherein the deionization filter media is positioned in the cartridge.

Another aspect of the invention is a mixing device, such as a venturi, connected between the treatment flow path and the recirculation flow path, the mixing device to help mix the treated water in the treatment flow path with the untreated water in the recirculation flow path.

In another aspect of the invention, a pump is positioned in the circulation flow path to assist in moving the water along the circulation flow path.

Another embodiment of the present invention includes a reservoir having a bottom surface including a valve means; a base unit for receiving the reservoir, the base unit including an ozone generator for ozonating water, a pump for drawing water from the reservoir into the base unit and through the ozone generator, and pumping water back into the reservoir; and a means for de-ionizing the water drawn from the reservoir. The base unit also includes a means for diverting the water from the reservoir back, past the ozone generator, and back into the reservoir.

Other features, utilities and advantages of various embodiments of the invention will be apparent from the following more particular description of embodiments of the invention as illustrated in the accompanying drawings.

BRIEF DESCRIPTION OF THE DRAWINGS

FIG. 2 is a perspective view of the present invention, including a base unit, a spray bottle and a cartridge.

FIG. 3 is an exploded view of the present invention shown in FIG. 2.

FIG. 8 is a rear view of the removable cartridge.

FIG. 9 is a section view of the removable cartridge, taken along line 9—9 of FIG. 8, including the cover, filter, de-ionization resin, serpentine region, diffuser plate, and inlet plate.

FIG. 11 is a perspective view of the spray bottle version of the reservoir.

FIG. 12 is an exploded view of the spray bottle shown in FIG. 11.

DETAILED DESCRIPTION OF THE INVENTION

Figure 1:
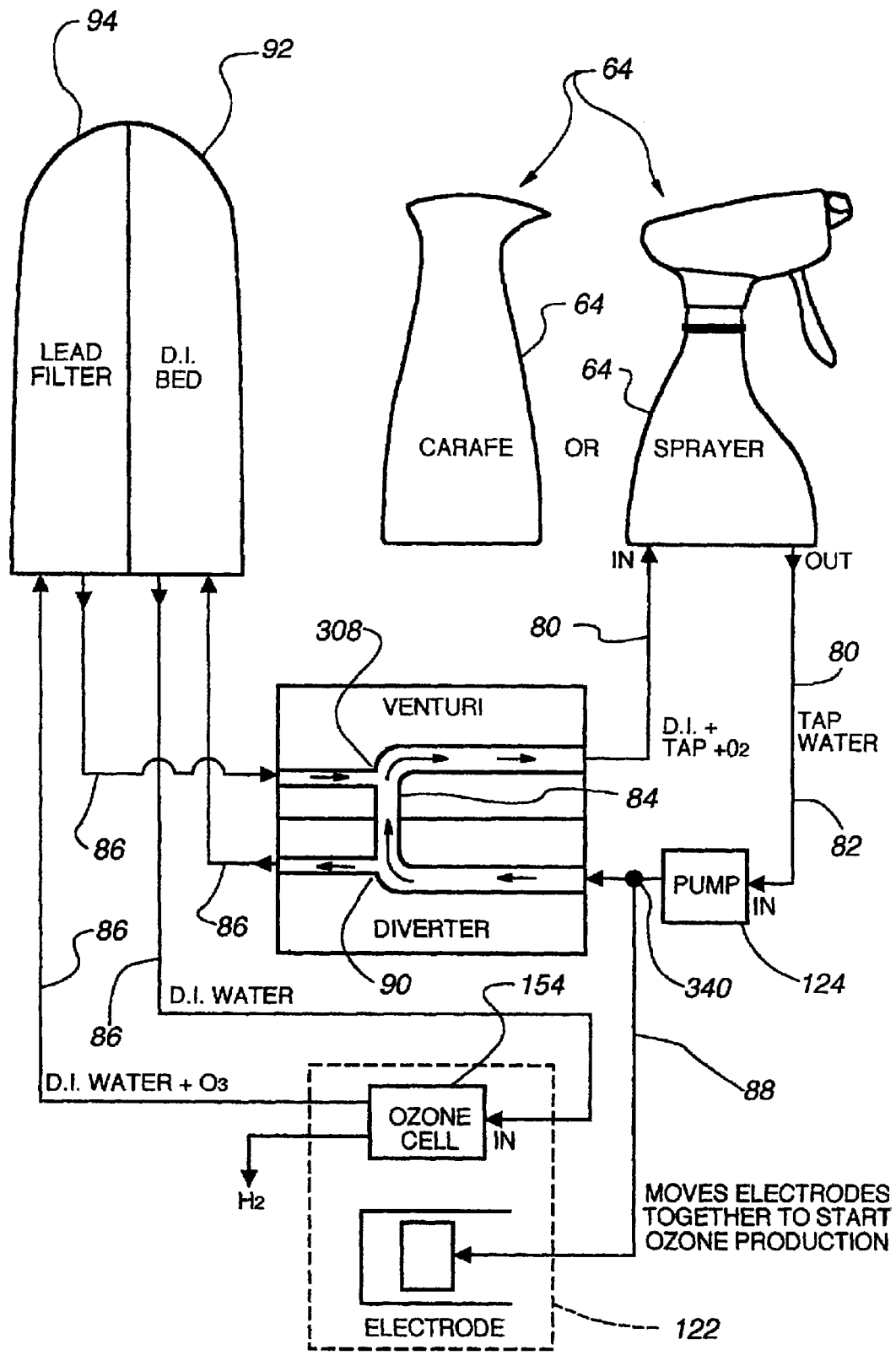
FIG. 1 is a schematic of the flow path circuit and related components of the present invention.

The present invention ozonation device is a compact and portable system for introducing ozone into water and for providing a convenient means for utilizing the ozonated water. In short, the present invention allows water in a handy reservoir to be ozonated in a simple, convenient and efficient manner. The ozonated water can then be applied to a variety of surfaces for cleaning and/or disinfecting purposes. The unit 60 includes a base 62, a reservoir 64 and a filter cartridge 66. The reservoir 64 is filled with water and placed on the base 62. The water in the reservoir 64 circulates through the base 62 and filter cartridge 66 to become ozonated, and then flows back into the reservoir 64. After this "charging" step is complete, the reservoir can be removed from the base 62 and used to apply the ozonated water in any manner desirable. The filter cartridge 66 is a separate element because it requires periodic replacement when its filtering qualities are diminished. It could, however, be built integrally with the base. The base 62 includes a control unit, using software to control the operation of the ozonating function. For instance, the control unit controls the "charging" of the water with ozone, turns on and off the ozone generator, senses performance (filter cartridge usefulness) and many other features to make the system work.

In one embodiment of the present invention, the invention is encompassed by the combination of a base unit 62, a reservoir 64 and a cartridge 66. The reservoir 64, typically defined by a spray bottle or carafe, is removably retained within a recess 68 defined in the top surface 70 of the main housing of the base 62. In addition, the water treatment cartridge containing deionization media and lead abatement media is removably retained within a second recess 72 in the top surface of the main housing. An ozone generator is also contained within the main housing 62. Finally, a circulating flow path is defined between the reservoir, the ozone generator, and the water treatment cartridge 66.

In operation, a user fills the reservoir 64 and places it in the corresponding recess 68 in the top surface 70 of the main housing 62. Automatic valves 74 formed in the bottom of the reservoir 64 form part of the circulation path and connect with valve assembly 78 formed in the surface of the main housing 62 and are in fluid connection with the ozone generator. The automatic valves 74 work as part of the circulation path to allow water to flow from the reservoir 64 to the ozone generator and back into the reservoir 64, during operation of the device 60. The user next actuates the device 60 by a control unit thereby causing both a device pump and ozone generator to actuate. Generally, water is circulated from the reservoir 64 to the ozone generator (and also through a deionization media and lead abatement media) and back to the reservoir 64 for a predetermined amount of time. Over time, the level of ozone in the water contained within the reservoir is increased. After the cycle ends, the user simply removes the reservoir 64 from the base and uses it as desired. In an embodiment where the reservoir 64 is defined by a spray bottle, the user might use the ozonated water to clean vegetables or clean countertops.

FIG. 1 is a block diagram that illustrates the water circuit of one embodiment of the present invention. To use the present invention system, the user fills the reservoir 64, in this case represented by a spray bottle, with tap water and installs it on the main housing 62. The interface between the bottle 64 and the main housing 62 contains two one-way valves 74 (one for outflow from the bottle to the main housing and one for inflow to the bottle from the main housing) that cooperate to automatically open when the spray bottle 64 is installed on the main housing 62 thereby allowing water to pass between the base main housing 62 and the spray bottle 64.

The user then activates a start switch of the control unit on the base main housing; the system could also automatically activate. The switch activates the pump, which draws tap water from the spray bottle into the ozone generator contained in the main housing. In one embodiment, the output of the pump has three branches including: a recirculation water path to a venturi mixer which then flows back to the bottle; a second flow path to the DI resin bed, which leads to the ozone cell; and a third path that leads a mechanical system to actuate the ozone generator (and thus the ozone cell). The water that goes through the recirculation branch flows through the venturi, then flows back to the bottle. The water that flows down the second path, is diverted to the DI resin and then through the ozone cell, then back to the venturi to be re-mixed with the water in the recirculation path, which flows back into the bottle. The water in the third path pressurizes a piston assembly in the ozone generator to move one member of the ozone cell towards the other member to complete the cell and start creating ozone for introduction to the water in the second path. This circulation path is described in more detail below with respect to FIG. 1.

As designed, the ozone cell needs DI water input to prevent "poisoning" of the cell by ions commonly present in tap water, which would shorten its life. The ozone cell uses DI water as input and dissociates part of the DI water flowing through it into ozone gas ($O_3$), oxygen gas ($O_2$), and hydrogen gas ($H_2$). The $H_2$ gas dissipates into the air as a waste product. The DI water exiting the ozone cell contains $O_2$ and $O_3$ gases. It may also contain trace amounts of dissolved lead from the lead oxide plating used in the cell as a catalyst. The cell generates the $O_3$ gas as micro bubbles that dissolve into the water. The water exiting the ozone cell (containing $O_2$ and $O_3$ gases) flows through a lead removal media to remove any trace amounts of lead. After exiting the lead filter, the ozonated DI water and ozone gas are fed back into the recirculation water line through a venturi. The venturi helps dissolve the ozone into the water. The water then flows back to the bottle.

The cycle continues for a preset amount of time during which the ozone concentration increases in the spray bottle to a desired level. The time period may vary depending on the size of the reservoir being ozonated. For example, a large reservoir may take approximately 15 minutes, while a small container may take approximately 10 minutes. The spray bottle or carafe ozone concentration is preferably about 2.0 ppm. At the end of the time period, the control unit instructs the pump and ozone cell to shut off. When the pump shuts off, the pressure on the piston keeping the cell in an operating orientation is released, and a biasing force, such as a spring, moves the movable member of the cell away from the rest of the cell, and thus terminates the ozone production. The user can then remove the reservoir and use the ozonated water to clean and/or disinfect food or surfaces.

Referring to FIG. 1, the circulation path 80 incorporated in the present invention is disclosed. The circulation path is generally a loop extending between the reservoir 64 and the ozone generator 122 to allow the water in the reservoir 64 to become charged or ozonated. In particular reference to FIG. 1, the circulation path 80, for a point of reference, begins and ends in the reservoir 64. The first section 82 of the circulation path flows from the reservoir 64 to the pump 124. Pump 124 comprises an electric motor 286 and a gear pump 288. The water flows to and through the pump 124 due to gravity as well as the draw created by the pump. After the pump, the circulation path braches into three different paths. The first path 84 is the recirculation path that flows back to the reservoir 64 through the venturi 308. The second path 86 flows to the ozone generator 122 for treatment by the ozone cell 154, and the third path 88 flows to the ozone generator 122 to actuate the ozone cell 154.

The first path (recirculation path) 84 flows through the venturi 308 to allow mixing with the treated water flowing in the second path 86, after that water has been treated by the ozone generator 122. The water stream in the first path 84 and second path 86 recombine at the venturi 308 to flow back to the reservoir 64.

The second path (the treatment path) 86 splits from the first path 84 in a diverter 90 (such as an aperture) to direct the water to the ozone generator 122 to be treated by the ozone cell 154. In the embodiment described herein, the second path 86, after splitting from the first path 84, leads to a DI resin bed 92 to deionize the water prior to the water being treated by the ozone cell 154. After the water flows through the DI bed 92, the second path 86 flows through the ozone cell 154 for treatment thereby. The ozone cell 154 ozonates the water, as described below. After the ozone cell 154, the second path 86 leads to a lead abatement filter 94 to remove any residual lead that may have been placed in the water stream in the ozone cell 154. After flowing through the lead abatement filter 94, the second channel 86 flows to the venturi 308 for recombination with the first path (the recirculation path) 84, which again Rows back to the reservoir 64.

The third path 88 formed by the circulation path 80 after the pump leads to the ozone generator 122 to actuate the ozone cell 154. This is the actuation path. The ozone generator 122 includes the ozone cell 154 and related mechanism that allow the ozone cell 154 to be in one of two positions: 1) disengaged where the ozone cell 154 is not operable, and 2) engaged, where the ozone cell 154 is operable. The third path 88 actuates the mechanism to cause the ozone cell 154 go change from the first, unengaged position to the second, engaged position. In the embodiment described herein, the third path 88 is a dead leg which creates pressure on a piston 350 (the pressure being developed by the pump) to move the ozone cell 154 into the second, operable position.

The circulation path shown in FIG. 1 is representative of one circulation path only. The important path is the one flowing from the reservoir 64 to the ozone cell 154 and back to the reservoir. The pathway through the DI resin bed, or through the lead abatement filter are not necessarily required. In addition, with a different cell structure, the pathway to actuate the mechanism to engage the ozone cell is also not necessary where the ozone cell does not require such actuation.

Figure 4:
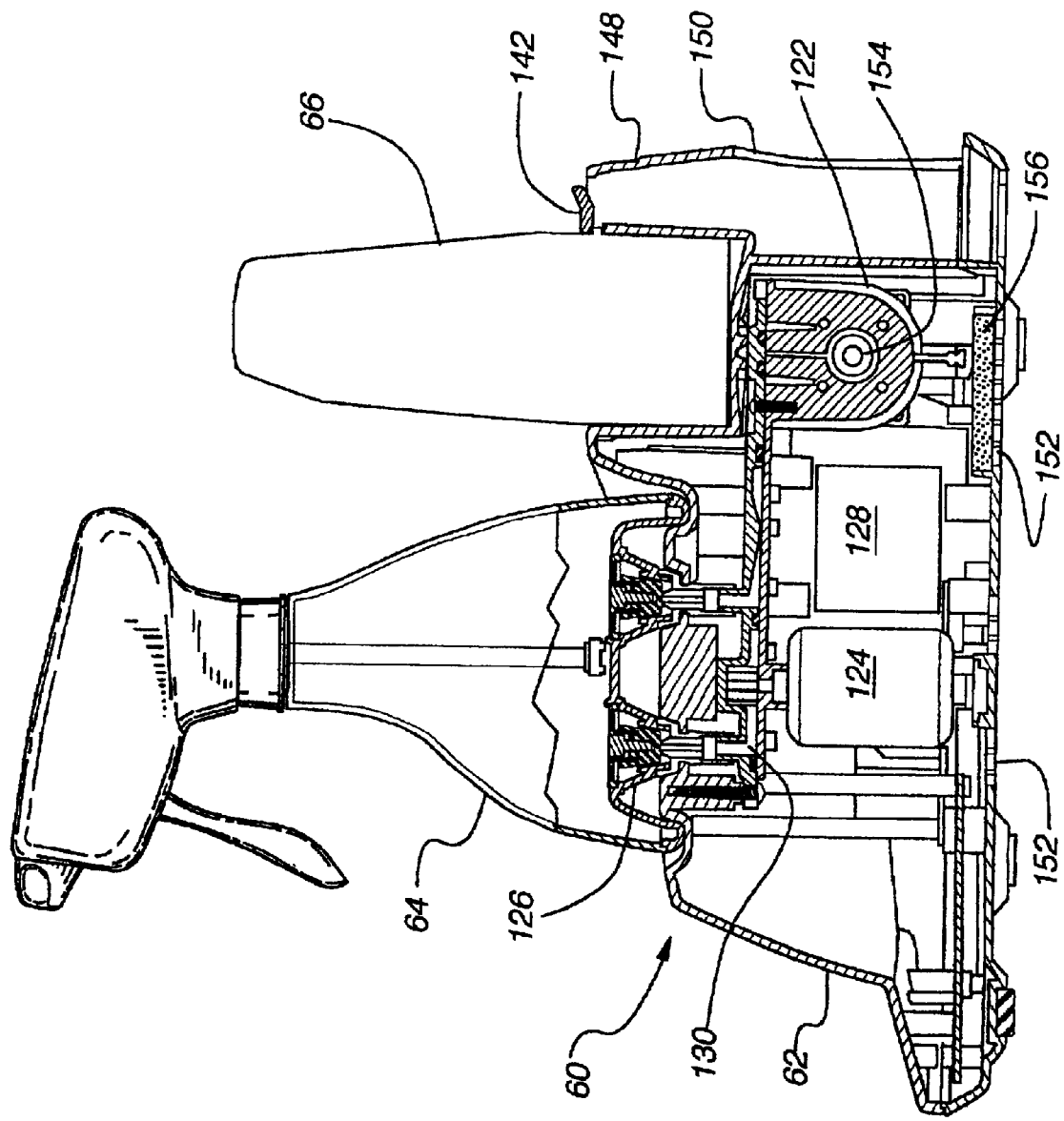
FIG. 4 is a section view of the present invention taken along line 4—4 of FIG. 2.

The spray bottle 64, base unit 62, and deionization and lead filter cartridge 66 (cartridge unit) according to one embodiment of the present invention are shown in FIGS. 2–4. While in the embodiment illustrated in FIG. 2 a spray bottle 64 is illustrated, a carafe or other container can be used in the system providing it includes a valve assembly 74 adapted to work with the valve assembly 78 in the base unit 62 of the system, all as part of the circulation path for charging the fluid in the reservoir 64 (bottle or carafe) with $O_3$.

As illustrated in FIG. 3, both the spray bottle 64 and cartridge 66 can be removed from the base unit 62 of the system 60. Typically, a user will remove the spray bottle 64 after the water is ozonated to spray the ozonated water as desired. The cartridge unit 66 will usually remain in the base unit 62. However, when the filtration media of the cartridge unit 66 is exhausted, the cartridge unit 66 can be removed and replaced with a new cartridge unit 66.

The base unit 62 is a housing containing: the ozone generator 122; the pump 124 and valve assembly 126 for moving the treated and untreated water along the circulation flow path; the control unit 128 for controlling the process; and a substantial part of the circulation path 80. As illustrated in FIG. 4, the ozone generator 122 and pump 124 mentioned above are enclosed within the base unit housing 62. Additional details regarding the spray bottle 64, the cartridge unit 66, and the base unit 62 are provided below.

As shown in FIGS. 2 and 3 and FIGS. 3 and 4, the base unit housing 62 contains the ozone generator 122, the pump 124, and the valve assemblies 126 for diverting both treated and untreated water. In one embodiment of the base unit housing 62, the base unit 62 is substantially oval in shape in the lateral dimensions. However, any shape could be used for the base unit housing 62 so long as the base unit housing design provides stability to hold the spray bottle 64 and cartridge unit 66 and house the ozone generator 122 described below. As illustrated in FIG. 3, there are two recesses 68, 72 in the top surface of the base unit housing 62. The front and larger recess 68 is adapted to receive a lower portion 76 of the reservoir 64. For the purposes of this description, reference to a spray bottle will be made, understanding that a carafe or other type of reservoir could be used. The rear and smaller recess 72 is adapted to receive the cartridge unit 66.

As illustrated in FIG. 3, the bottom surface of the front recess includes valve assemblies 78 adapted to correspondingly connect with the valve assemblies 74 on the bottom surface of the spray bottle 64. The recess 72 for the cartridge unit 66 defines apertures on a bottom wall of the recess to correspond to apertures on a base wall of the cartridge unit. These apertures are part of the circulation path. As also illustrated in FIGS. 2 and 3, a user places the spray bottle 64 in the larger recess 68 towards the front of the top surface 70 of the base unit 62. The user places the cartridge unit 66 in the rear recess 72 of the base unit 62. Both the spray bottle recess 68 and the cartridge unit recess 72 are configured to securely hold the spray bottle 64 and cartridge unit 66, respectively. The larger recess 68, or spray bottle recess, as illustrated in FIG. 3, includes a raised portion 132 on the bottom surface of the recess 68. The valve assemblies 78 on the base unit 62 for the spray bottle 64 reside within the raised portion 132. The bottom 76 of the reservoir defines a recess 134 having sidewalls and a ceiling (part of the bottom wall of the reservoir). The valve assemblies 74 for the bottle 64 are in the ceiling of the recess 134. The raised portion 132 has the same general shape as the recess 134, and provides added stability for the spray bottle 64 as it resides within the recess 68 in the main housing. In addition, the shape of the raised surface 132 acts as a key to help the user properly orient the spray bottle 64 within the recess 68 in the main housing 62.

A lower front portion of the base unit 136 illustrated in FIGS. 2 and 3 defines a shelf 138. In one embodiment, the shelf 138 includes an interface for the control unit 128 for actuating the device. In addition to the dimensions of the spray bottle 64 and the cartridge unit 66, other parameters that affect the dimensions of the base unit 62 include the desired water flow capacity of the system, the necessary size of the ozone generator 122 to meet the desired capacity, the power supply, printed circuit board, and other elements.

A cantilever deflecting rib 142 on the back of the cartridge housing cooperates with a catch 144 on the back portion of the corresponding cartridge recess 72 to releasably secure the cartridge housing 66 within the main housing cartridge recess 72. (See FIGS. 3 and 4.) A power switch is located along one of the side surfaces of the main housing 62 and supplies power to the control unit 128, the pump 124, and the ozone generator 122 when turned on. The unit is powered by line voltage from regular 110ν electrical service, and can also be battery powered.

A backside wall 148 is vented to facilitate cooling of the generator motor and drying of an evaporation media. FIG. 4 shows two vents, a first vented area 150 located to reside below the motor, and a second smaller vented area 152 is located to reside below cell chamber 154.

Figure 5:
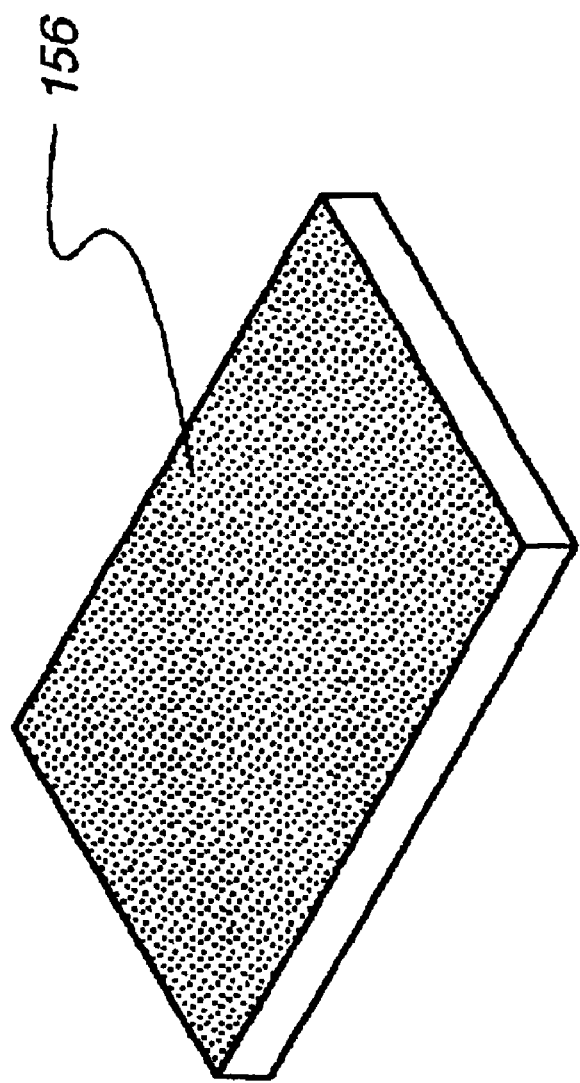
FIG. 5 is a perspective view of the evaporation media incorporated in the present invention.

An evaporation media 156 (see FIG. 5) is located adjacent the smaller vented area 152 beneath the ozone generator cell chamber 154 (see FIG. 4). Referring to FIG. 5, the evaporation media 156 is formed from a sponge-like absorbent material. The evaporation media is configured to collect any moisture that leaks from the ozone generator 122. The vented bottom surface 152 in the lower housing portion and vented sidewall 150 in the back 148 of the upper housing portion 62 facilitate drying of the evaporation media 156.

Figure 6:
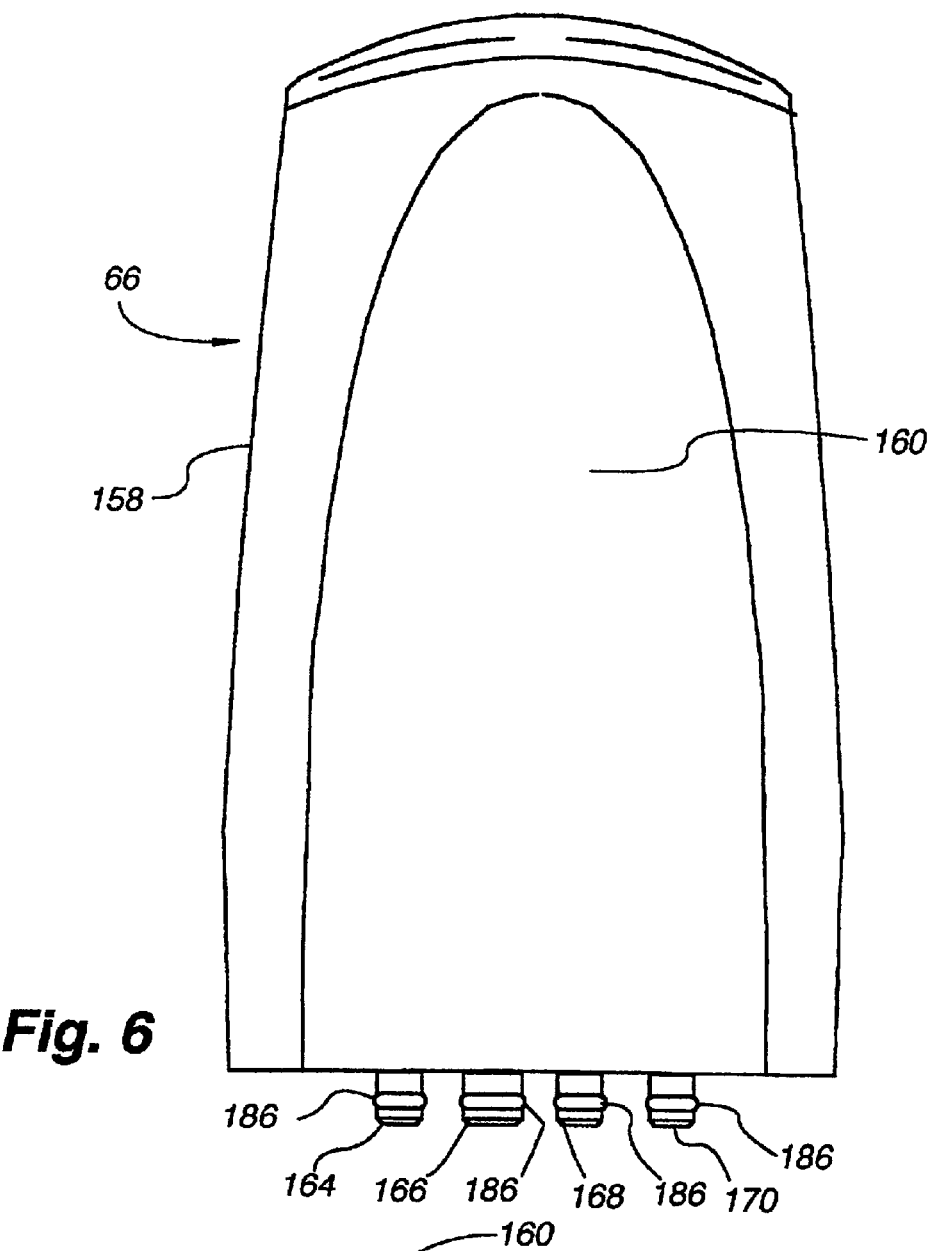
FIG. 6 is a front view of the removable cartridge.
Figure 7:
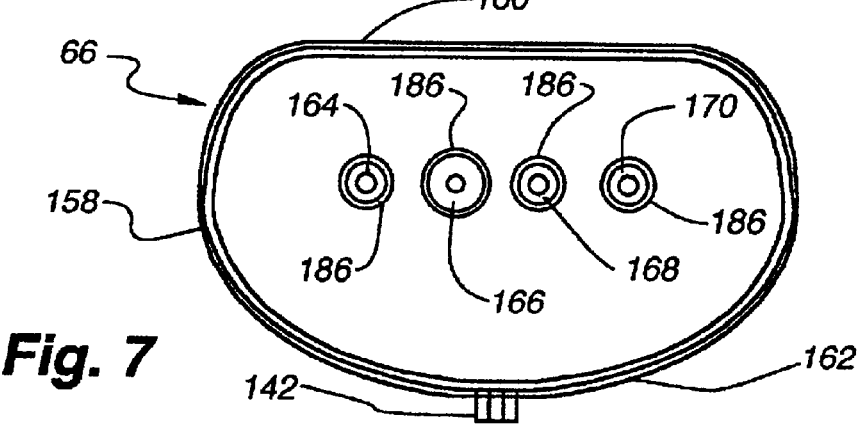
FIG. 7 is a bottom view of the removable cartridge and shows the ports for interconnecting with the circulation path formed in the base unit.

FIGS. 6–10B illustrate the cartridge element 66. The cartridge includes a cartridge housing 158 having a flat front surface 160 and a rounded back surface 162. The cartridge housing 158 contains a DI resin filter separated into several separate but interconnected chambers 172, and a lead abatement region in a serpentine layout. FIG. 6 shows the four apertures formed in the bottom of the cartridge. From left to right, aperture 164 is the inlet to the DI chamber. Aperture 166 is the outlet from the DI chamber. Aperture 168 is the inlet to the lead abatement region, and aperture 170 is the outlet from the lead abatement region. FIG. 7 shows the apertures from a bottom view. FIG. 8 shows the rib 142 that helps keep the cartridge 66 in the recess 72. FIG. 9 is a cross section showing a couple DI chambers 172, down tubes, fitter tops, and the lead abatement serpentine 178. These will be described in more detail below.

Figure 10A:
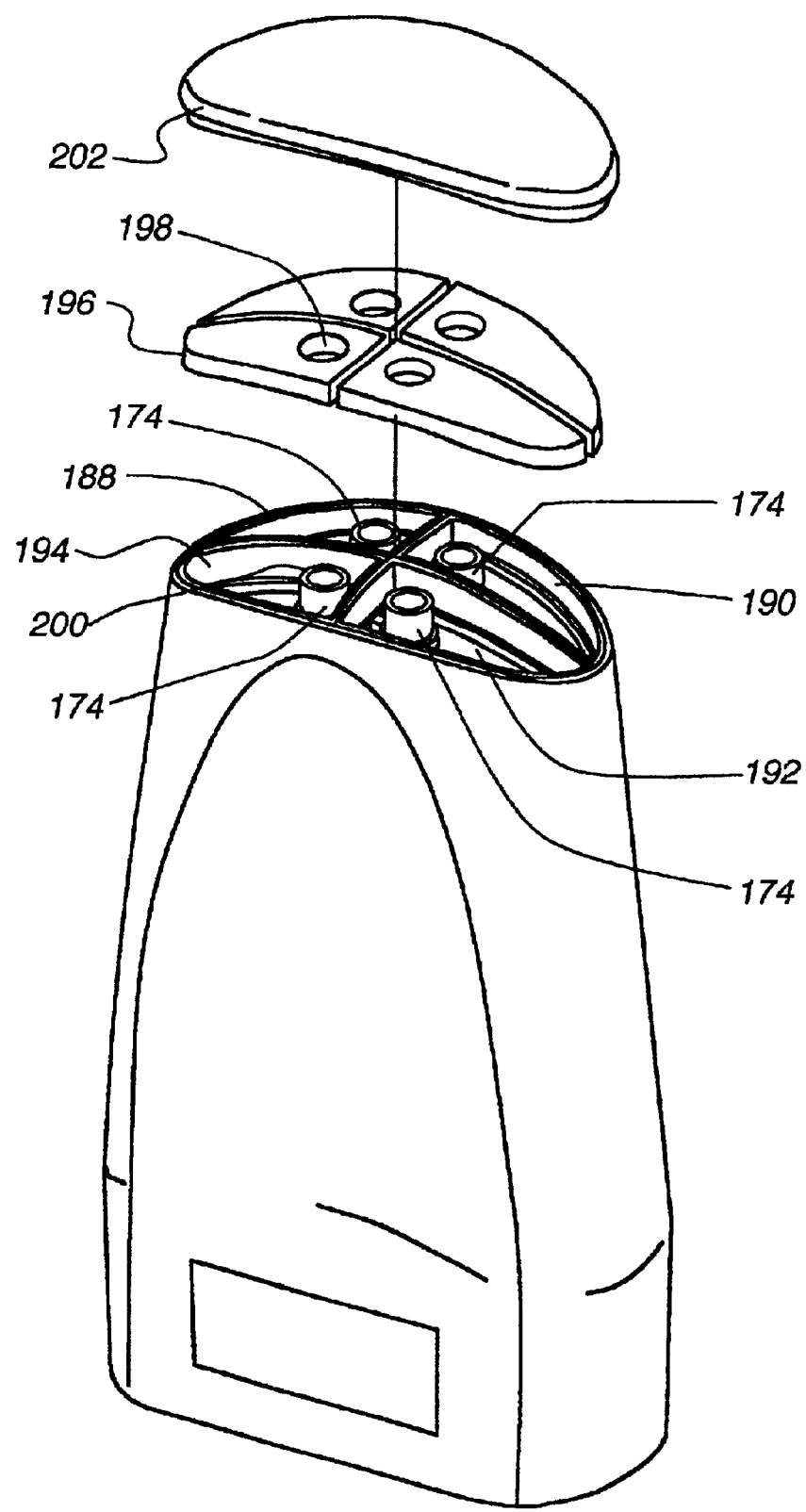
FIGS. 10A and B are an exploded view of the cartridge.
Figure 10B:
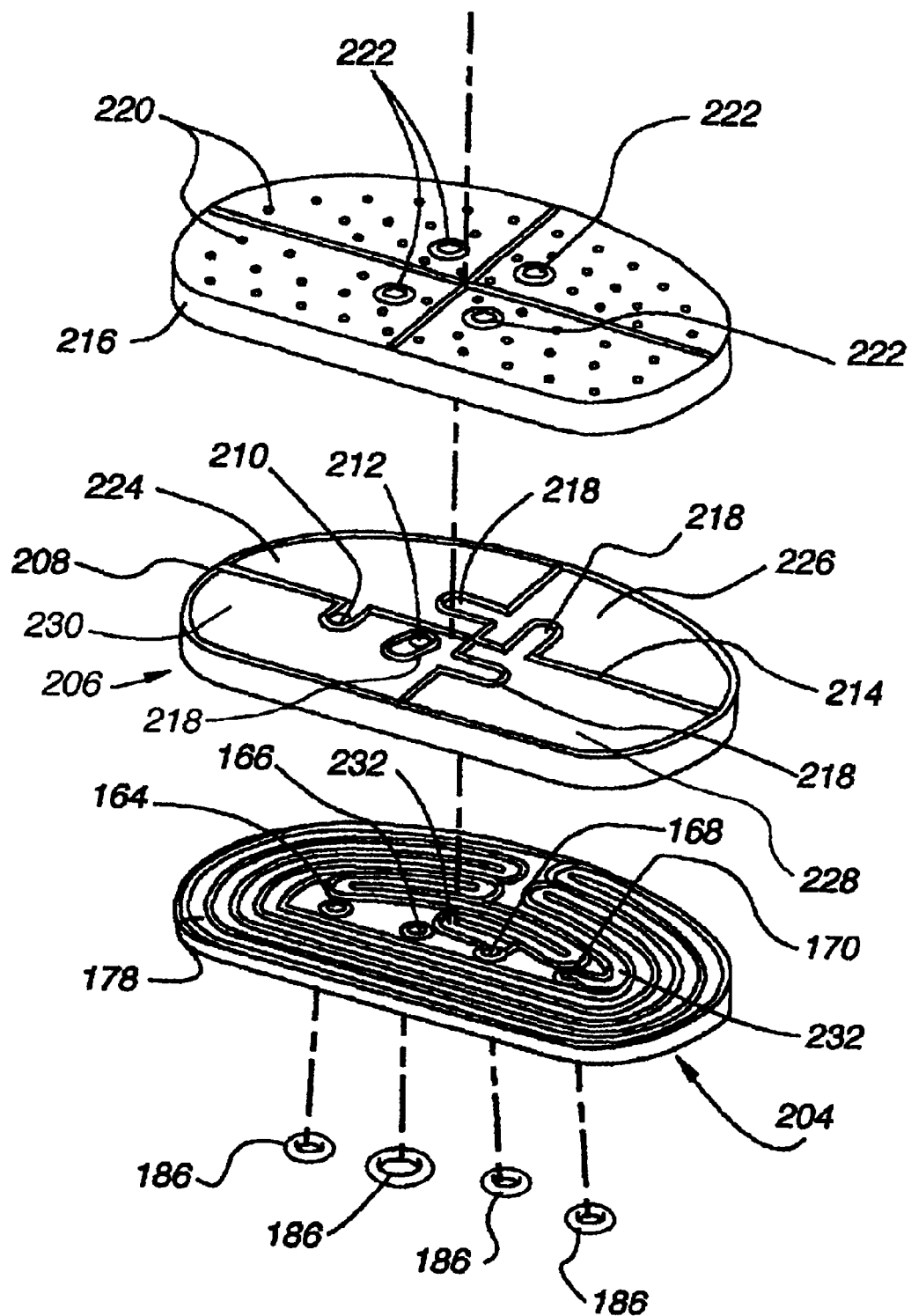

FIGS. 10A and B are front exploded isometric views of the cartridge unit 66. In the embodiment illustrated in FIGS. 6, 10A and 10B, the cartridge unit 66 encloses media 180 for deionizing water prior to entering the ozone generator 122, and the lead abatement filter 178 for removing trace amounts of lead after the water has passed through the ozone generator 122. In one embodiment the cartridge unit 66 is divided into two regions, one for the DI water treatment and one for the lead abatement treatment. In the preferred embodiment, the top chamber 182 includes the deionizing media 180 and a bottom chamber 184 includes the lead filter. (See FIG. 9.) Although the embodiment illustrated in FIGS. 10A and B is generally rectangular in shape, any shape capable of enclosing both the deionizing media 180 and the lead filter 178 is acceptable providing it corresponds with the recess 72 in the base unit 62 of the system 60 and the applicable apertures 164, 166, 168, 170. The two chambers 182, 184 could also be side by side or in any different configuration.

As mentioned above, in addition, the back surface 162 of the cartridge housing 158 also includes a rib 142 that mates with a catch 144 located on the device base 62. The catch 144 operates with the rib 142 on the cartridge 66 to hold the cartridge 66 in place during operation of the device 60.

As illustrated in FIGS. 6 and 7, the bottom surface of the cartridge unit 66 includes apertures 164, 166, 168, 170 for allowing water to enter and exit both the deionization chamber 182 and the lead filter chamber 184. The apertures can be watertight fittings that mate with corresponding fittings in the base of the recess 72 for the cartridge 66. O-rings 186 or the like can be used to allow the fittings to seal tightly together but also provide a removable fit. The apertures 164, 166, 168, 170 can also be similar to those between the bottom of the reservoir 64 and the circulation path, which are open when engaged and closed when not engaged. This valve variation is described in more detail below.

Since the cartridge 66 is not removed and replaced very often, the fittings structure (without valves) would be appropriate. The fittings, or valves, on the bottom of the recess 72 for the cartridge 66 are part of the circulation path, and either lead from the path to the DI water treatment, or from the DI water treatment to the ozone generator 122 or from the ozone generator 122 to the lead abatement region, or from the lead abatement region to the venturi to mix the charged water with the water in the recirculation path.

For example, in one embodiment of the cartridge unit 66 illustrated in FIG. 7, the circles illustrated on the left side of the bottom surface of the cartridge unit represent an inlet 164 and an outlet 166 for water to enter and exit the deionization media. The circles illustrated on the right side of the bottom surface of the cartridge unit represent an inlet 168 and outlet 170 for water to enter and exit the lead abatement filter 178 in the cartridge unit 66. The valve assemblies used in one embodiment of the present invention cartridge unit are adapted to cooperate with the valve assemblies in the corresponding cartridge recess in the base unit 62 of the system 60. The valve assemblies utilized in the cartridge unit are substantially similar to those used in the spray bottle 64 and spray bottle recess 68 (described below). When a cartridge unit 66 is removed from the base unit 62, the valve assemblies on the cartridge 66 automatically close to seal the cartridge unit 66. Correspondingly, when the cartridge unit 66 is placed in the recess 72 within the base unit, the valves assembled on the bottom of the cartridge 66 automatically open to allow water to enter and exit the cartridge unit 66. As described above, in one embodiment of the present invention system, untreated water is pumped through the deionization media 180 in the cartridge unit prior to introducing the water to the ozone cell. After ozonation, the de-ionized and ozonated water is then fed to the lead abatement filter 178 in the cartridge prior to ultimately exiting the base unit 62 and reentering the spray bottle 64.

The top chamber 182 of the cartridge housing 158 (see FIG. 9) for DI filtering is divided into four quadrants. As illustrated in FIGS. 10A and B, quadrant one 188 is in the upper left hand corner and the remaining quadrants are numbered sequentially in a clockwise manner. Each quadrant forms a sub-chamber that extends the length of the top portion 182. Each quadrant includes a tube 174 extending the length of the sub-chamber, which tube serves as a down-flow tube. Each sub-chamber is filled with a deionizing (DI) material to de-ionize the tap water used in the device 60. A porous filter 196 is positioned at the top of each sub-chamber to collect the DI fines out of the water so they do not clog the venturi. The porous filter 196 in each sub-chamber defines an aperture 198 that fits over the down-flow tube. The upper end 200 of the down-flow tube extends above or flush with the top surface of the filter. The filter 196 can be one piece, as shown in FIGS. 10A and B, to fit fully over the top of the DI chambers. A cover 202 fits over the open top of the cartridge and is attached with a watertight seal. There is a space between the cover and the filter to allow the water to flow therebetween. (See FIG. 9.)

The bottom of the cartridge includes three plates delineating two intervening layers. The bottom or inlet plate 204 forms the four apertures 164, 166, 168, 170 therethrough (described above) to allow in-flow and out-flow to and from the DI and lead abatement regions. The top surface of the inlet plate forms a continuous channel in a labyrinth, serpentine-like shape. The channel leads from the inlet of the lead abatement region (aperture in inlet plate) to the outlet of the lead abatement 178 region (aperture in inlet plate).

The second plate 206, or labyrinth plate, has the same labyrinth design on its bottom surface as the design on the top surface of the inlet plate. These two plates are connected together along the common walls of the channel (which weld together) and along the outer rim 208 of the second plate. This forms the labyrinth pathway between the two plates. The second plate has two apertures 210, 212 in it that match and align with the two apertures in the inlet plate that are associated with the inlet 164 and outlet 166 of the DI chamber. The top of the second plate 206 is divided into four quadrants 224, 226, 228, 230 to match with and seal 214 between the four quadrants formed in the distribution plate, as described below. These quadrants also correspond to the quadrants 188, 190, 192, 194 of the DI chamber. The upper left quadrant, or first quadrant, of the second plate 206 is sealed to the bottom of the corresponding chamber. The DI inlet aperture 164 is encompassed by the perimeter of the first quadrant wall in the distribution plate, so the water flows into the first quadrant and up through the DI material in the first DI chamber. More detail on the water flow path is provided below.

The other quadrants on the top of the second plate also seal with the corresponding quadrants in the distribution plate, forming a plurality of DI chambers 172 attached in series. The perimeter of each quadrant defines a protrusion 218 to encompass a down-flow tube 174 and to divert the water into the next chamber, or to allow the water to enter the first chamber or exit the last chamber and continue on the circulation path.

A distribution plate 216 is positioned above the second plate 206. The distribution plate 216 is also separated into the four quadrants on both its top and bottom surfaces. The shape of the quadrants on the bottom surface of the distribution plate 216 match the shape of the quadrants on the top of the second plate, in order to facilitate the correct water flow from one DI quadrant to another. Each of the quadrants in the distribution plate are perforated with small apertures 220 in order to distribute the water somewhat evenly over the cross-sectional area of the DI material 180 in the particular chamber. This helps minimize channeling and increases the efficiency of the effect and length of life of the DI filtration process. Each quadrant also defines a larger aperture 222 that matches with the protrusions 218 in the perimeters of the quadrants on the top side of the second plate 206. Each of these apertures 222 seals with the bottom of a down-flow tube 174 to direct the water to the next quadrant, as is explained in more detail below. The top surface of the distribution plate 216 seals with the quadrant walls of the main body 158.

The flow path of the water through the DI chamber starts at the inlet aperture 164 formed in the inlet plate 204. The water flows up through the inlet aperture 164, and up through the inlet aperture 210 in the second plate 206. The water is distributed through the perforations 220 in the first quadrant section of the perforation plate 216, and then flows upwardly through the DI material 180 in the first quadrant chamber 188. The water then flows through the top filter 196 above the first quadrant 188 and enters the first down-flow tube 174 and flows downwardly to the bottom of the tube and exits into the protrusion 218 that leads the water into the second quadrant 226. The water then flows upwardly through the perforations in the second quadrant section of the perforation plate 216, and then flows upwardly through the DI material in the second quadrant chamber. The water then flows through the top filter 196 above the second quadrant 190, and enters the second down-flow tube 200 and flows downwardly to the bottom of the tube and exits into the protrusion 218 that leads the water into the third quadrant 228. The water then flows upwardly through the perforations 220 in the third quadrant section 228 of the perforation plate, and then flows upwardly through the DI material 180 in the third quadrant chamber 192. The water then flows through the top filter 196 above the third quadrant 192, and enters the third down-flow tube 174 and flows downwardly to the bottom of the tube and exits into the protrusion 218 that leads the water into the fourth quadrant 230. The water then flows upwardly through the perforations 220 in the fourth quadrant section 230 of the perforation plate 216, and then flows upwardly through the DI material 180 in the fourth quadrant chamber 194. The water then flows through the top filter 196 above the fourth quadrant 194, and enters the fourth down-flow tube 174 and flows downwardly to the bottom of the tube and out the outlet hole in the distribution plate, which is connected to the outlet hole 212 in the second plate, and which is in turn connected to the outlet hole 166 in the inlet plate 204. The water then continues flowing along the circulation path to the ozone generator 122.

The flow through the DI resin material 180 is designed to maximize the residence time of the water with the DI material 180. This could also be done with various other flow geometries inside of the cartridge 66, or inside the base housing 62 if this portion of the circulation path was designed to be inside the main housing. The inlet 164 and outlet 166 ports of the DI material flow-path are sealingly engaged (such as with o-ring seals to allow a removable engagement) with the corresponding circulation flow path structures.

As described above, after the DI process, the water flows through the enlarged port 166 and into the ozone generator cell chamber 154. Deionized water is used to prevent "poisoning" the ozone generation cell by ions in tap water, which could shorten the cell life. Distilled water could also be used in place of deionized water to prevent poisoning of the ozone generation cell by ions in tap water. While not necessary, in practice, utilizing deionization is a cost effective way of pre-treating the tap water.

After the water is ozonated in the ozone generator 122, the water is pumped into the bottom chamber 184 of the cartridge housing 158 and into the lead abatement section 178 to remove any trace amounts of lead that may be present in the water. The ozonated water enters the cartridge housing via the lead abatement inlet port 168. The ozonated water enters the labyrinth pathway channels defined by the underside of the labyrinth plate and the inlet plate, as described above. The ozonated water flows through lead removal resin that resides in the labyrinth pathway channels 232. The labyrinth pathway channels 232 are comprised of small channels containing lead abatement material, and the channels serve to keep the velocity of the gas/fluid mixture high enough to transport the gases through the lead abatement resin thereby preventing gas from being trapped in the cartridge housing. In one embodiment the labyrinth channels 232 are 0.125 inches by 0.100 inches. In the unlikely event that the ozonated water contains trace amount of lead from the lead dioxide on the anode, the lead removal resin will substantially remove any trace amounts of lead. The preferred lead abatement resin is activated alumina. Typical activated alumina beads are 0.06–0.09 inches in diameter. However, other lead removal resins could be utilized (e.g., ATS coated alumina). After flowing through the labyrinth 232, the ozonated water exits the cartridge housing 158 via the lead abatement exit port 170. The water flows from the fourth port and re-enters the ozone generator 122, flowing into the channel that leads to the venturi for re-introduction into the circulation stream. The lead abatement medium is not necessary given the slight levels of lead that might be found in the ozonated water. In the case where it is unnecessary, the lead abatement material can simply be removed from the lead abatement region of the cartridge, or the flow path can be modified altogether to flow directly from the ozone cell to the venturi.

The DI resin 180 generally loses its effectiveness after approximately 300 ozonation cycles. The flow control software described below includes a counter that counts the number of ozonation cycles run through a filter. As described in more detail below, an alarm and signal notifies the user when the DI resin 180 requires replacement. In other embodiments, the status of the DI resin could be indicated using color indicating resin or from an alarm or indicator that is activated based on the results of conductivity measurements of the DI resin 180.

Regarding the geometry of the DI resin chamber 172, a tall, cylindrical DI resin chamber has been found to be effective. The four-quadrant columnar chambers generally replicate the preferred geometry by connecting 4 shorter length chambers. This design is preferred to provide a design with a lower profile. Regarding the type of DI resin 180, in one embodiment, a mixed bed DI resin is utilized. In a mixed bed resin, the resin is comprised of both anion and cation exchange resins, which can be synthetic, natural (such as zeolite). Other suitable DI resins include product number MBD-10-NS from RESINTECH, Inc., which is a combination anion/cation resin, or equivalent.

The cartridge housing 158 and related elements are generally constructed of ABS, white, RM No. 20000839 (Virgin). Alternate materials include but are not limited to regrind ABS, white, RM No. 20000840 (25% blend).

FIGS. 11 and 12 illustrate a spray bottle 64 that can be used as part of the present invention. A spray bottle 64 allows the user to spray the ozonated water on surfaces, foods and vegetables, and clothing. The present invention spray bottle 64 includes a hand-actuated spray nozzle 234 with a tube 236 extending to the bottom of the bottle 64 as known in the art; preferably the present invention spray nozzle is adjustable and can provide a fine stream spray or a wide stream spray.

The spray nozzle removably attaches to a transparent spray bottle 238. The spray nozzle 234 is removed from the spray bottle for the purpose of filling the spray bottle 238 with water. The spray bottle portion is generally well known in the art. However, in the present invention, the spray bottle includes valve assemblies 74 on its bottom surface 76. As illustrated in FIG. 11, the bottom surface 76 of the spray bottle includes a portion that extends upwardly into the spray bottle to form a recess 134. The recess 134 is configured to receive the raised portion 132 on the bottom surface of the spray bottle recess 68 in the base unit 62.

As seen in FIGS. 11 and 12, the bottom surface 76 of the spray bottle 64 includes valve assemblies 74 adapted to connect with the valve assemblies 78 located on the bottom surface of the spray bottle recess 68 in the base unit. The valve assemblies 74 on the bottom surface of the spray bottle are adapted to automatically close when the spray bottle 64 is removed from the base unit recess 68, thereby effectively sealing the bottom surface 76 of the spray bottle 64. Conversely, when the spray bottle 64 is placed in the spray bottle recess 68 in the base unit 62, the valve assemblies 74 on the bottom surface 76 of the spray bottle 64 automatically open and cooperate with the valve assemblies 78 on the bottom surface of the spray bottle recess 68 to allow water to flow in and out of both the spray bottle 64 and the base unit 62.

Figure 13:
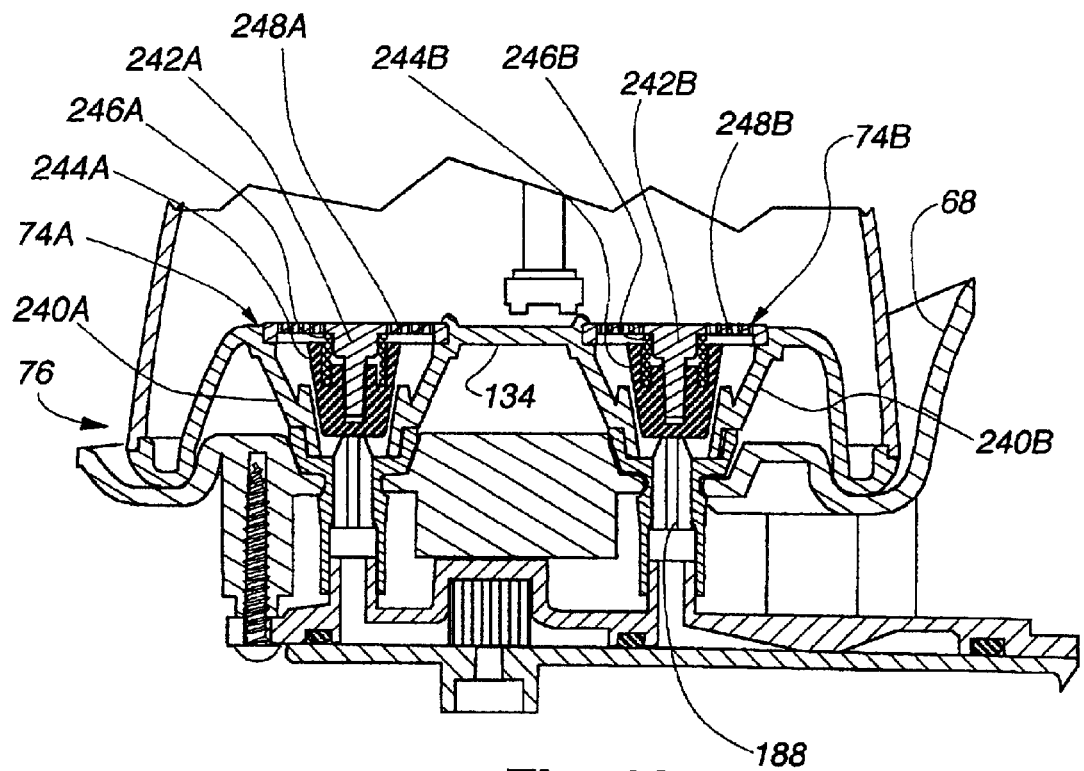
FIG. 13 is a partial section view taken along line 13—13 of FIG. 11, showing the valve assemblies at the bottom of the bottle, with the bottle placed on the base unit, the valve assemblies in the open position.
Figure 14:
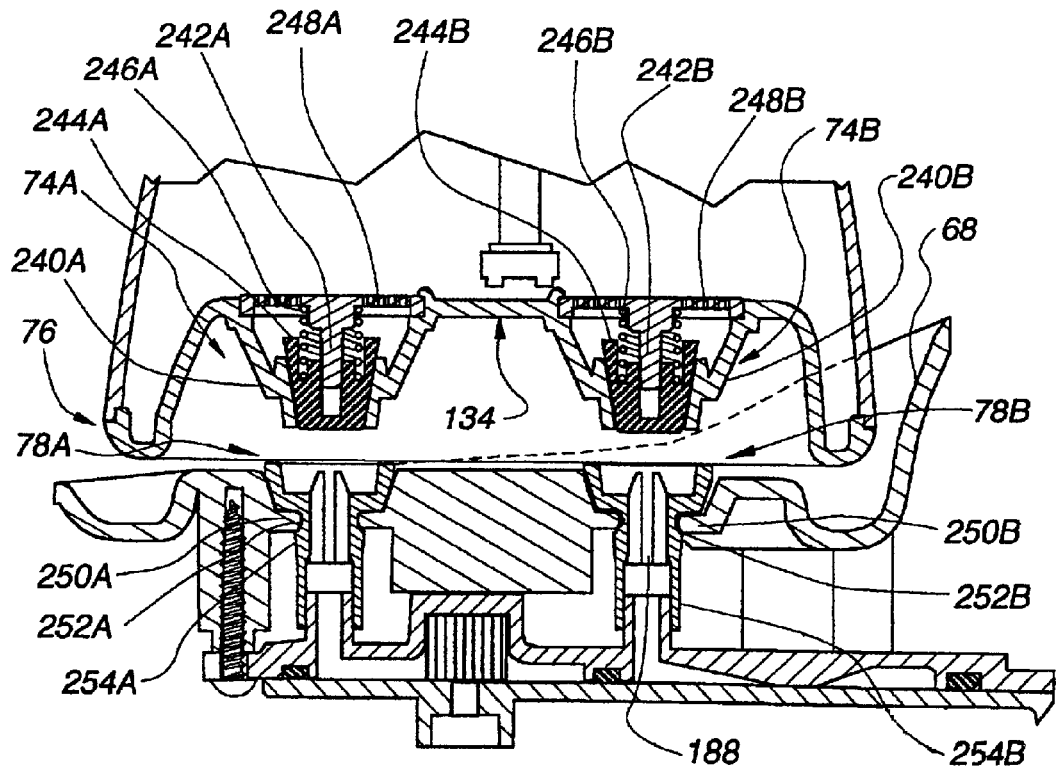
FIG. 14 is a partial section view similar to that shown in FIG. 13, wherein the valve assemblies are closed.

As shown in FIGS. 13 and 14, the valve assemblies 74 on the bottom of the bottle work with the corresponding valve assemblies 78 positioned in the aperture at the bottom of the bottle recess 68 in the main housing 62. The front aperture 78A in the main housing recess 68 allows water to flow from the bottle 64 into the main housing 62 and to the ozone generator 122, and the rear aperture 188 allows water to flow from the main housing 62 (already having been treated by the ozone generator and the venturi) and back into the bottle 64. The bottle 64 and inlet 74A and outlet 74B valves are part of the circulation path. The front 74A and rear 74B outlets can be reversed or re-positioned with the appropriate changes being made to the circulation path structure inside the main housing.

Still referring to FIGS. 13 and 14, the valve assemblies 74A, 74B on the bottom of the bottle each include a collar 240A, 240B forming the aperture, a pin 242A, 242B extending down into the aperture, a plug 244A, 244B slidably positioned on the pin 242, a spring mechanism 246A, 246B biasing the plug 244 into the lower, closed position, and a screen 248A, 248B covering the top opening of the collar 240. The collar 240 is slightly cone-shaped (smaller diameter downwardly positioned) to allow the tapered plug 244 to seat in the collar 240 and make a watertight seal when in the lower position. The spring 246 keeps the plug 244 in the seated position. The plug 244 can be slid upwardly along the pin 242 to an unseated, or unsealed, position by an adequate force. When the force is removed, the plug 244 is biased back into the seated position by the spring 246.

The valve assemblies 78A, 78B in the bottom of the recess in the main housing 62 each include an outer flange 250A, 250B forming the aperture into the main housing 62. Each flange 250 also forms an annular groove 252A, 252B around a stand tube 254A, 254B for receiving the bottom end of the collar 240. The stand tube 254 extends upwardly from the groove 252 in the center of the flange 250. The stand tube 254 extends sufficiently above the bottom of the annular groove 252 such that when the bottle 64 is placed in the recess 68 and the corresponding two valve assemblies 74, 78 engage, the stand tube 254 pushes the plug 244 upwardly enough to move it to an unseated position in the collar 240 (see FIG. 13). This allows water to either flow out of bottle 62 through the particular valve assembly 74A, or into the bottle through the other valve assembly 74B.

Referring back to FIGS. 11 and 12, the sprayer mechanism assembly 234 is generally typical of those found in the art. However, the present invention sprayer mechanism assembly 234 has a nozzle 256 that is designed to not atomize the mixture while spraying. The present invention sprayer mechanism assembly reduces the amount of mist created while the mixture is being sprayed. It is designed to eject small streams of the mixture, which helps keep the ozone gas in the liquid. The stream spray basically has a larger stream size than normal to keep the stream from misting when sprayed. The nozzle includes six holes: three inner holes 258 and three outer holes 260. In one embodiment, the nozzle provides at least two modes of spray: 1) where the nozzle is completely open or unscrewed, all six streams 258, 260 combine to form a spray; and 2) where the nozzle is screwed all the way in, the three outside streams 260 are blocked and only the three smaller holes 258 combine to form spray. The nozzle 256 may also include a fully closed position that prevents fluids or gases from escaping the spray bottle. In one embodiment, all of the holes in the nozzle are 0.04 inches in diameter. In normal operation, approximately 2.5 ml of mixture is ejected from the sprayer per spray. By avoiding atomization of the mixture, the ozone loss is limited to 20–30% each spray. The sprayer mechanism assembly 234 is configured to releasably attach to an open top portion of the spray bottle portion 238. The grooved collar 262 releasably attaches to a threaded open top portion 264 of the spray bottle 238. Fluid and gases contained in the sprayer bottle 64 are drawn into the body and forced out of the sprayer nozzle by squeezing the trigger.

As illustrated in FIGS. 11 and 12, the sprayer bottle portion is a typical polymer based material and is typically formed from two pieces: a body portion 268; and a bottom portion 76. The two pieces are typically sonically welded together. In one embodiment, it is substantially transparent to allow the user to view the contents of the bottle 64. In addition, generally the top of the body portion is threaded to allow mating with the collar on the sprayer mechanism assembly. In the present invention, the shape of the body portion bottom is configured to attach to the and to fit within the reservoir container recess formed in the top surface of the upper housing portion of the main housing. The bottom of the bottle includes the valve assemblies.

Figures 15, 16:
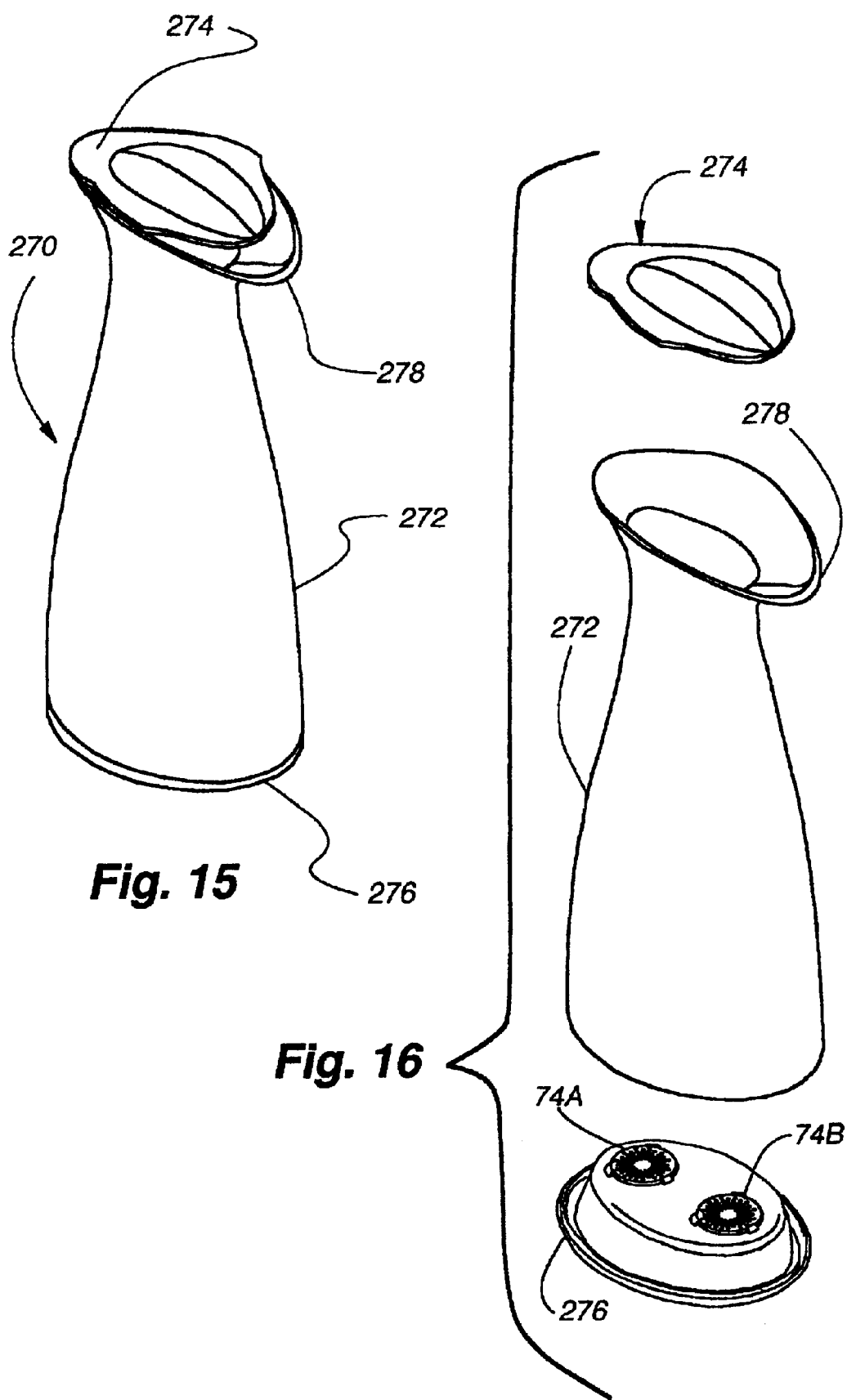
FIG. 15 shows a carafe style reservoir.
FIG. 16 shows an exploded view of the carafe style reservoir of FIG. 15, showing the valve assemblies similar to those shown in FIG. 13.

Alternative reservoir containers can also be utilized in the present invention. One example of an alternative reservoir container is a carafe 270. See FIGS. 15 and 16. A reservoir container having a carafe body 272, a lid 274, and a bottom 276 including the valve assemblies 74A, 74B (same as valve assemblies 126) is illustrated in FIGS. 15 and 16. The lid snap 274 fits to the carafe body 272 and can be opened during use. The body 272 includes a v-notched pour spout 278 for directing fluids while pouring.

The carafe container 270 allows a user to introduce gross quantities of treated water to selected areas or surfaces. Examples of such uses include pouring treated water over plants, over fruits and vegetables, and into drinking containers. The carafe container 270 includes the same valve assemblies used in the spray bottle and described above. Other types of containers could be utilized in the present invention providing they include valve assemblies capable of cooperating with the main housing valve assemblies.

The front shelf portion 138 of the upper housing portion includes a control panel on its surface. The control panel is operably connected to a control unit 128 circuit board (discussed later). The control panel is configured to include push buttons that allow the user to operate the functions of the device. A more detailed description is provided below.

Figure 17:
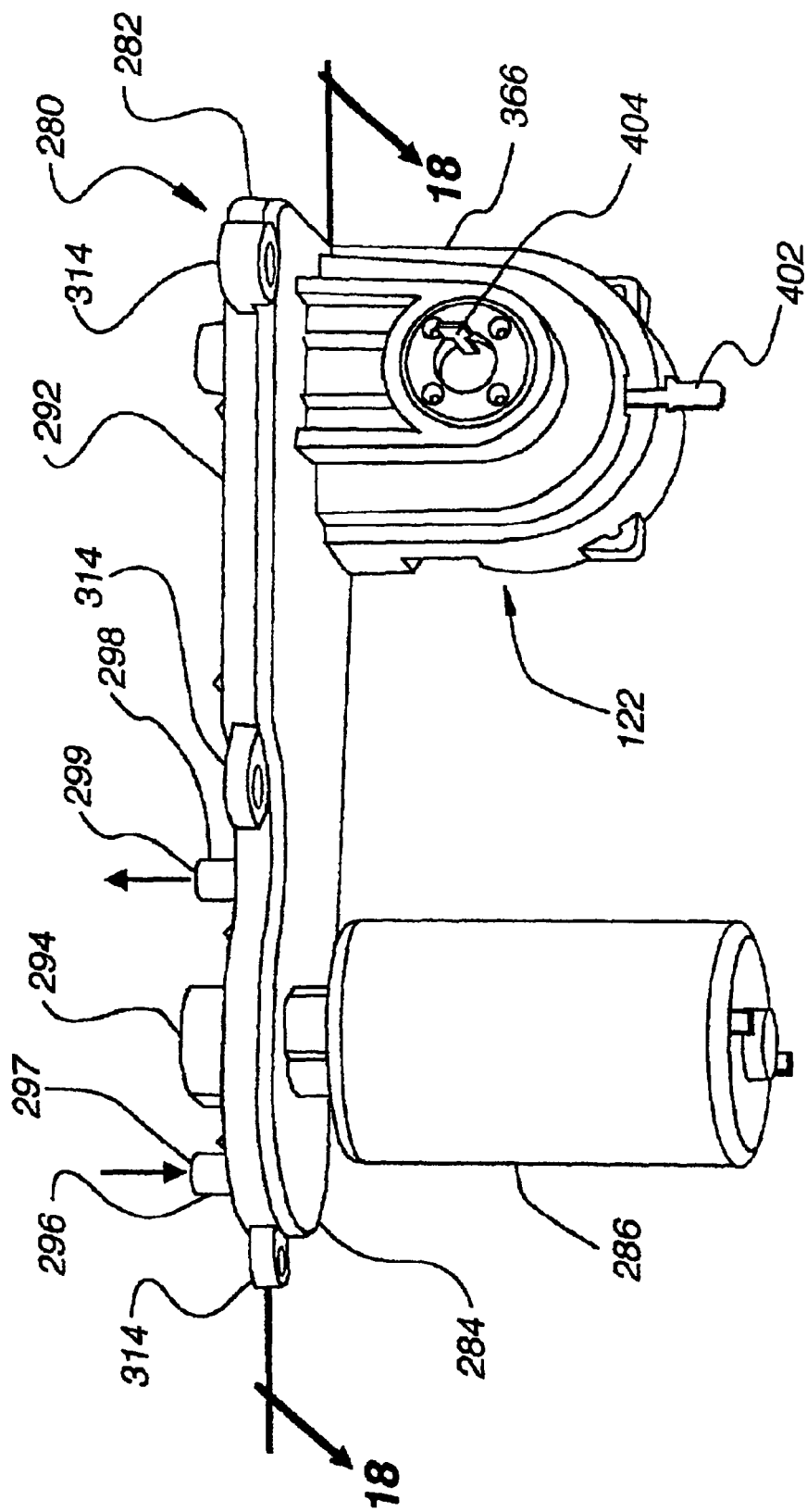
FIG. 17 is a perspective view of the manifold encompassing a portion of the circulation path, the pump and motor, and the ozone generator.

As illustrated in FIG. 17, a manifold is secured to the upper housing portion of the main housing 62. The manifold includes an upper 282 and lower 284 housing portion, the lower portion containing the ozone generator 122 depending downwardly therefrom at one end. At the opposite end, an electric motor 286 depends downwardly from the lower manifold 284. The motor is used to drive the gear pump 288, as is described in greater detail below.

Figure 18:
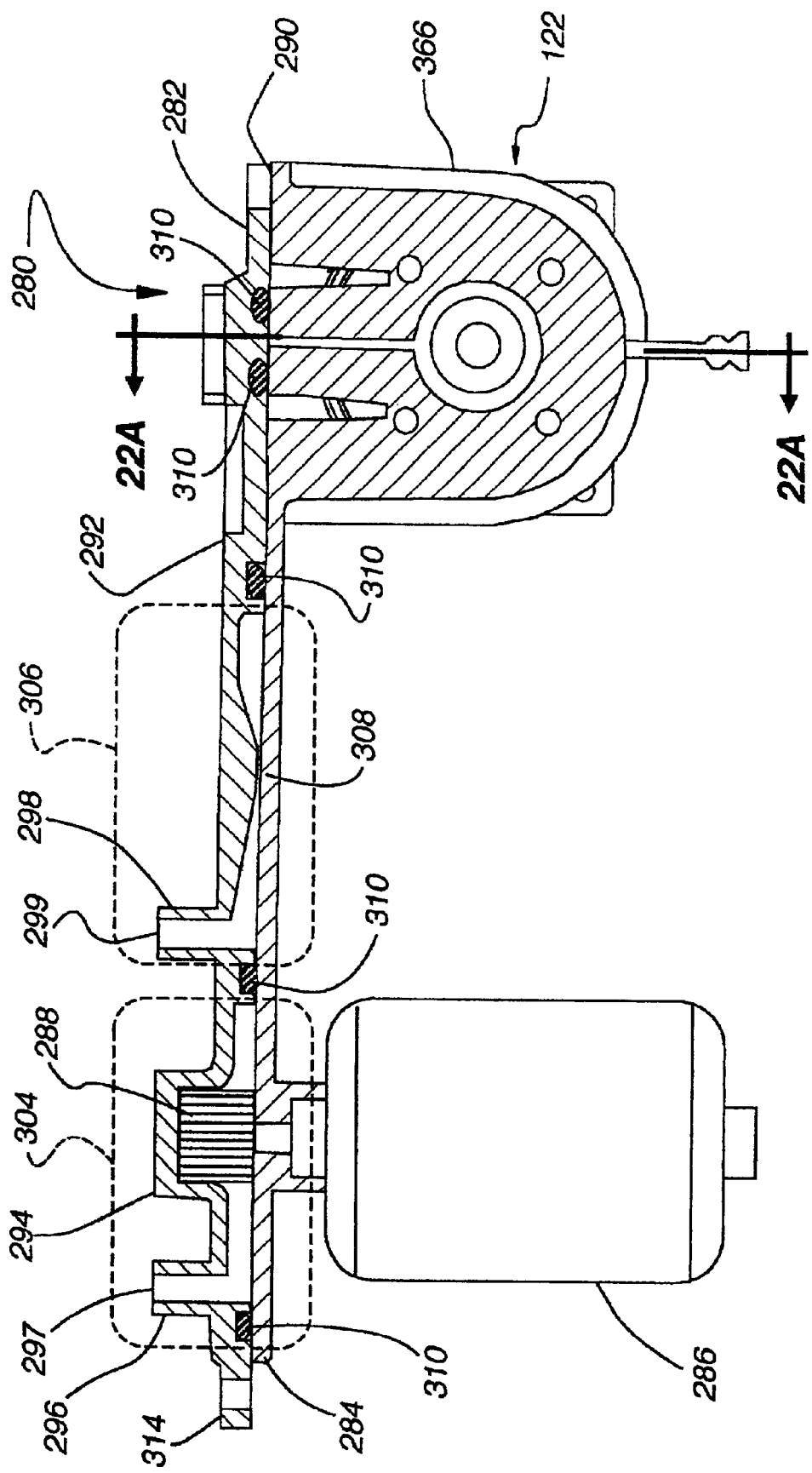
FIG. 18 is a section view of the manifold taken along line 18—18 of FIG. 17, and shows the inlet and outlet ports to the reservoir, the mixing means (venturi) and the top and bottom portions of the manifold.

As illustrated in FIGS. 17 and 18, the lower manifold 284 forms the bottom surface 290 of the manifold 280. The upper manifold 282 forms the top surface of the manifold 280. The gear pump motor 286 resides below and is connected to the gear pump 288, which is located in the gear pump housing 294 formed in the upper manifold 282. The ozone generator 122 is suspended from the right side of the manifold as shown in FIG. 18. The flow ports that allow water to flow to and from the ozone generator 122 are located above the ozone generator 122 on the right side of the manifold. The left-most stand tube 296 defines the port 297 that allows water to flow from the reservoir container 64 into the manifold 280. The next stand tube to the right 298 allows water to flow out of the manifold 280 and back into the reservoir 64 after treatment. Other apertures are formed in the upper manifold to allow flow to and from the cartridge 66.

FIG. 18 shows various parts of the circulation path 80 formed in the manifold. In the first region 304 shown, the water enters the manifold 280 from the reservoir 64 through the valve assembly 126 associated with the left-most aperture or port 297. The gear pump 288, driven by the motor 286, draws the water from the reservoir 64 (with the aid of gravity) and generates sufficient pressure to push it through the rest of the circulation path 80. The motor drives one gear 300, which is engaged with a second free-floating gear 302, and together this gear pump 288 creates sufficient pressure to push the water through the circulation path 80. The second region 306 shown is the venturi 308 and exit from the manifold 280 back into the reservoir 64. In the second region 306, the venturi 308 is formed to take water from the recirculation path 342 and from the ozone generator 122 and mix the two streams together in the venturi 308. The mixed water then flows back into the reservoir 64 through the valve assembly 126 associated with the right-most aperture or port 299. FIG. 18 also indicates that the top of the lower manifold portion 284 is relatively planar, with the flow paths being formed by the seals 310 held in place against the lower manifold by the upper manifold. This will be described in more detail later.

Figure 19:
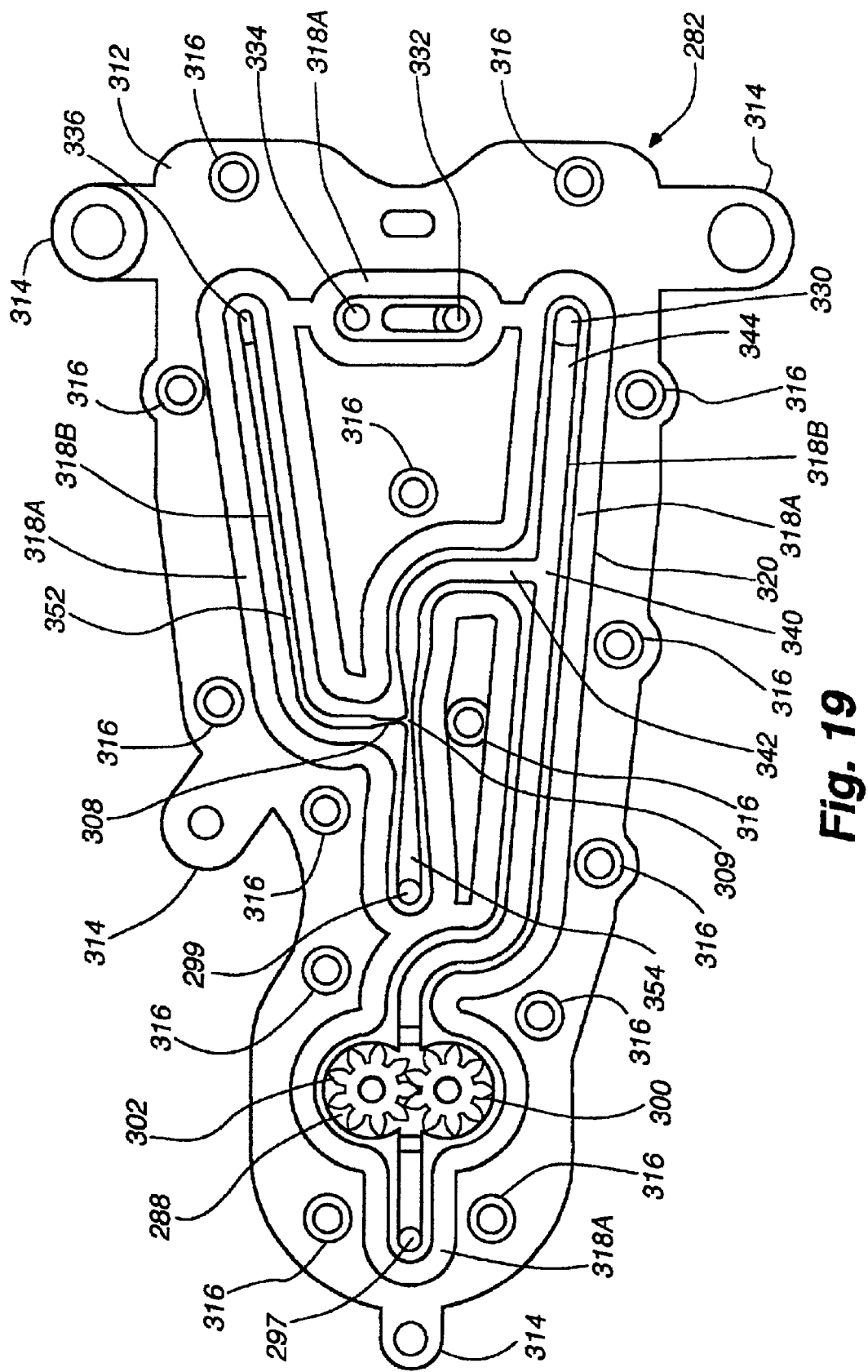
FIG. 19 is an underside view of the top portion of the manifold, and shows the seal groove, a portion of the circulation path, the mixing means (venturi) and various ports.
Figure 20:
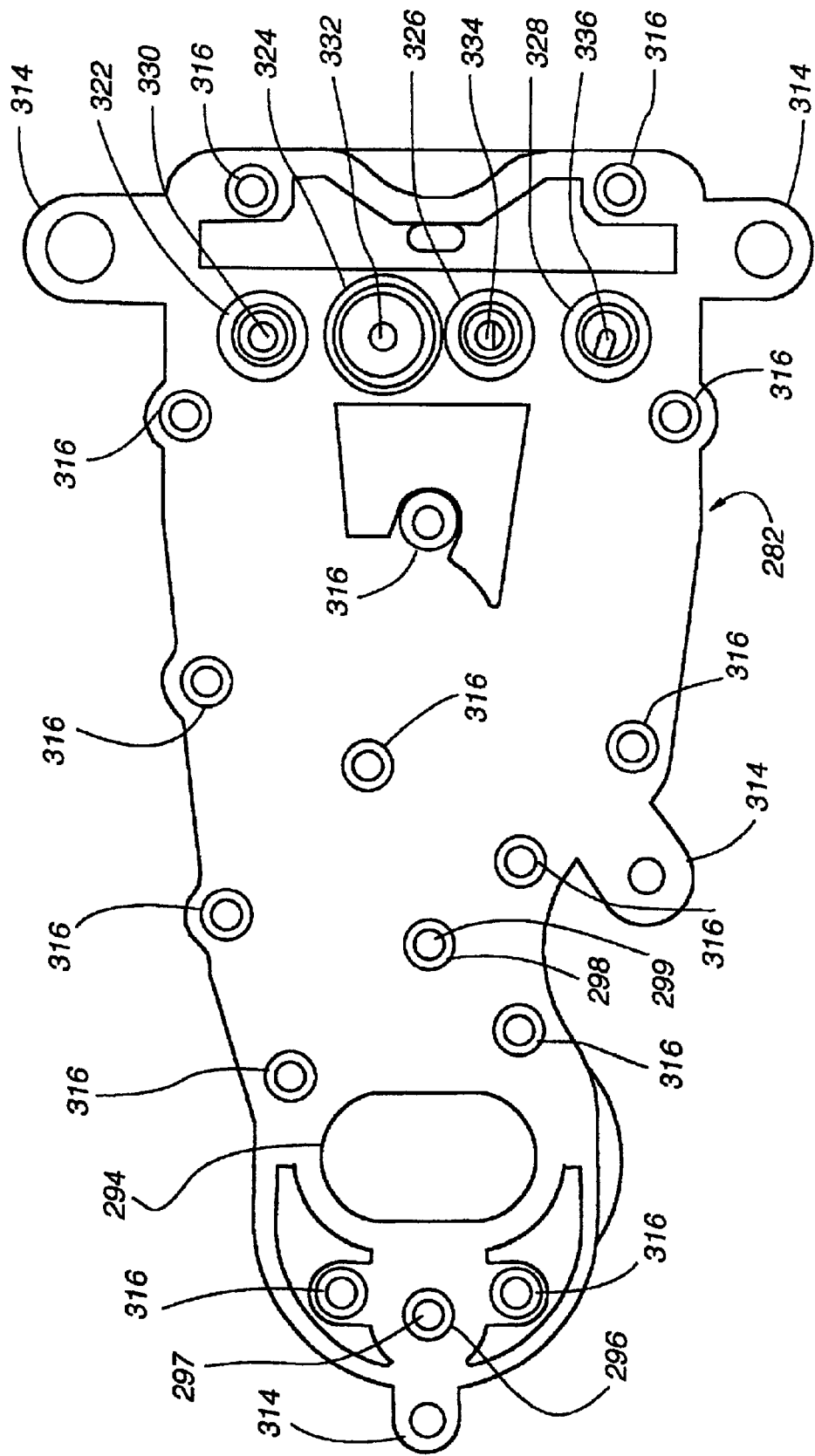
FIG. 20 is a top view of the top portion of the manifold.

FIGS. 19 and 20 provide additional details on the ozone generator system of the present invention. The flow path of the water in the ozone generator system is best illustrated in FIG. 19. FIG. 19 shows the bottom surface 312 of the upper manifold portion 282. The bottom side 312 of the upper manifold 282 includes tabs 314, screw holes 316, and various grooves 318. The overall shape of the upper manifold 282 is configured to fit within the base housing 62 of the present invention device, and to fit precisely with the bottom manifold portion 284.

As mentioned previously, the upper manifold includes mounting tabs 314. The mounting tabs are used to mount the manifold inside the device base housing. In FIG. 19, four mounting tabs 314 are illustrated. However, in other embodiments, more or less mounting tabs may be utilized. As illustrated in FIG. 19, the upper manifold 282 also includes multiple screw holes 316. The screw holes 316 are used to attach the upper manifold 282 to the lower manifold 284. In addition to screw holes 316 and screws 317, other means for attaching the upper and lower manifolds could be utilized. Other means include detent structures or rivets, or the like.

The bottom surface 312 of the upper manifold 282 also includes a series of grooves 318. One groove 318A is for receiving the seal 310 between the upper and lower manifolds, and the other 318B forms the physical channels of the portion of the circulation path 80 formed in the manifold 280. The outermost groove 318A is a groove for receiving a housing seal 310. The housing seal groove 318A is generally exterior to other grooves in the bottom surface of the upper manifold 282. The housing seal groove 218A, in combination with the seal 310, generally provides a seal around all water-flow channels and ports between the upper and lower manifolds. The seal 310 is generally a rubber, plastic, or similar material formed to fit in the seal groove 318A and for a water tight seal when clamped between the upper and lower manifolds. Both the water flow channels and ports are discussed in greater detail below. The housing seal 310 is received by the housing seal groove 318A and sandwiched between the upper 282 and lower 284 manifolds. The housing seal 310 serves to prevent any fluids from leaking out of the circulation path and manifold. In one embodiment (not shown in the drawings), an outer groove may be formed on the lower manifold (outside of the housing seal). This outer groove serves to direct any water that leaks past the housing seal (out of the generator) to an evaporation media (discussed below).

As mentioned above, the bottom surface 312 of the upper manifold 282 also includes the channels 320 that form the portion of the circulation path 80 that is formed by the manifold 280. The water-flow channels 318B within the upper manifold bottom surface are generally U-shaped open channels for ease of manufacture. In use, the flat lower manifold 284 covers the U-shaped channel 318B to form a generally rectangular channel. However, any shape of channel cross section, such as cylindrical channels, could be used in other embodiments (upper and lower manifolds joined to form a cylindrical channel). In one embodiment, the rectangular channels are 0.02 inches wide by 0.02 inches deep.

FIG. 20 illustrates a top view of the upper manifold 282. Mounting tabs 314 and screw holes 316 are also formed in the upper manifold 282. In addition, the stand tubes 296, 298, 322, 324, 326, 328 that connect the reservoir container 64 to the manifold 280, and the cartridge 66 are also illustrated in FIG. 20. On the left-most side of the top surface of the upper manifold 282, is the port 297 through which the water flows from the reservoir 64 to the manifold 280. The next stand tube to the right 298 allows water to flow from the manifold 280 back into the reservoir container 64. The stand tubes may also include a porous plastic screen, or other such device, to prevent debris from clogging the venturi 308.

In between the stand tubes is an oval-shaped surface that represents the top surface of the gear pump housing enclosure 294. At the right end of the upper manifold are four ports 330, 332, 334, 336. The four ports are configured to receive the four apertures 164, 166, 168, 170 on the bottom of the cartridge housing 66. The top port 330 in FIG. 20 allows water to exit the manifold 280 and flow to the DI resin located in the cartridge housing 66. The second port 332 just below the DI resin port 330 is enlarged. The enlarged port 332 allows water to flow from the DI resin back into the ozone generator 122 and into the ozone reaction chamber or cell 154. The third port 334 allows water to flow from the ozone reaction chamber or cell 154 to a labyrinth containing lead abatement resin. The labyrinth and lead abatement resin are located in the bottom portion of the cartridge housing 66. The bottom-most or fourth port 336 allows water to flow from the lead abatement resin in the cartridge housing 66 back into the manifold 280 and towards the venturi 308.

Water entering the manifold flows from the reservoir container 64, through a valve tube, and into a stand tube 296, as illustrated in FIG. 20, and into the receiving channel on the upstream side of the gear pump housing 294. The upstream side of the gear pumping is the side closest to the port 297 where water enters the fluid circuit from the reservoir container 64. As illustrated in FIGS. 19 and 20, water enters the generator on the left side of the upper manifold bottom surface 312. Water is pumped to the right as shown in FIG. 19 within the manifold 280 by a gear pump 288 that resides in a gear pump housing 294 recess. The gear pump 288 draws water from the reservoir container 64 (e.g., spray bottle or carafe) and through the gear pump housing 294 recess and pumps it along the circulation path 80 in the manifold 280. The gear pump 288 is located outside of the ozone generator 122. The water is pumped along the circulation channel to a first junction 340 (see FIG. 1 or 19).

At the first junction 340, the channel branches toward a recirculation channel path 342 and a second way toward the DI resin (DI water path) 344. The water channel 344 leading to toward the DI resin also further branches to a dead leg path 346 that causes pressure to build on the upstream side 349 of the piston 350 in the ozone generator (system actuation path), as described in some detail here, and in more detail below. The pressure on the piston 350 serves to actuate a diaphragm/anode post assembly. When the diaphragm/anode post assembly is actuated, the ozone generation cell and cycle is activated (system is actuated). The second path channel 344 that flows towards the DI resin chamber also flows to the dead-leg channel 346 to actuate the piston 350. The water flowing to the DI resin chamber flows upwardly out of the manifold 280 through aperture 330, and the water that is used to pressurize and actuate the piston flows downwardly into the ozone generator 122.

As also illustrated in FIG. 20, the water flowing toward the DI resin exits a port in the top surface 330 of the upper manifold and enters a DI resin chamber 182 that is housed in the cartridge housing (described above) 66. The water is deionized prior to entering the ozone generation cell to prevent "poisoning" of the cell by ions in the tap water. The use of deionized water in the reservoir container 64 would eliminate the need for DI resin. After circulating through the DI resin, the deionized water enters the ozone generator 122. The deionized water enters the ozone generator through the enlarged port 332 (as illustrated in FIG. 20). The deionized water then flows into and through the ozone cell 154. In the ozone cell 154, the deionized water is ozonated. The anode 356 and possibly other components of the ozone cell 154 are possibly plated with lead dioxide. Lead dioxide serves to increase the electrochemical reactions that produce ozone gases.

The ozonated water is now a mixture of H, $O_3$, $O_2$, and $H_2O$. The ozonated mixture then exits the ozone generator 122 and re-enters the cartridge housing 66. The water exiting the ozone cell 154 is then run through the lead abatement media (as described above) to remove any trace amounts of lead that may exist in the ozonated water. The ozonated water circulates through a labyrinth filled with lead abatement resin and then re-enters the ozone generator 122. The ozonated water exiting the lead abatement labyrinth re-enters the ozone generator via the bottom-most port 336 (as illustrated in FIG. 20).

The ozonated water then flows along a channel 352 formed in the bottom surface of the upper manifold 282 and flows to the venturi 308. At the venturi 308, the ozonated water is mixed with water flowing in the re-circulation line 342. The mixture of ozonated and re-circulated water then flows into an exit channel 354. From the exit channel 354, the ozonated mixture exits the manifold 280 through a stand tube 298 and valve assembly (as described above) and enters the reservoir container 64. Generally, for example, the re-circulation stream flows at 300 ml/minute and the stream flowing through the DI resin and ozone generator flows at 20 ml/minute. In other embodiments, the stream rates may vary (e.g., re-circulation stream of 200–400 ml/minute).

The venturi 308 helps to promote dissolution of the ozone in the water via the following means: by creating a turbulent zone that increases the contact time of the ozone with the water; and by shearing ozone bubbles into smaller bubbles to increase the overall surface area of ozone in the water. The venturi design geometry can affect the pressure loss experienced through the venturi. In one embodiment, the venturi inlet angle is 20° and the outlet angle is 7°. For ease of manufacturing, the venturi in the present invention is formed from rectangular channels 318B (U-shaped channel in upper manifold bottom surface covered by flat lower manifold surface to form a rectangular channel). In other embodiments, cylindrical channels could be used (as formed by upper and lower manifold surfaces). In one embodiment, the rectangular channels are 0.020 by 0.020 inches. The geometry of the venturi channels (channels narrow to an intersection) generally increases the velocity of the water contained therein as it flows through the narrowing channels (velocity=flow rate/area). The accelerated water basically collides at an intersection thereby increasing the mixing of the two flows entering the venturi. The resulting mixed flow enters a third channel. The third channel increases in diameter to help reduce the velocity of the flow.

While the venturi 308 benefits the ozonation of the water by helping mix the ozone into the recirculation path of the water, any mixing device or means would suffice, but possibly not be as effective. In fact, the invention can work without the venturi 308 or any type of mixing means. Other types of mixing means include converging flowpaths (whether at acute, obtuse, or right angles), perforated screens, mechanical mixers, or any other type of structure or system that cause the ozonated sample of water to flow into an untreated stream and mix the two together.

A gear pump 288 draws water from the reservoir container 64 and into the fluid circuit. The majority of the water flows into the re-circulation path 342 towards the venturi 308. The balance of the water flows into the DI path 344 towards the DI resin. The water flowing into the DI path also flows to into a dead leg 346 that forms the system actuation path 348. The system actuation path dead-ends into the upstream side of the piston 350. The water flowing into the system actuation path 348 causes a pressure of 20–30 psi to build against the upstream side of the piston 350 thereby causing the piston to move forward. By moving forward, the piston causes the diaphragm/anode post assembly to move the anode 356 into contact with the proton exchange membrane 358 thereby actuating the ozone generator. The water flowing into the DI resin circulates through the DI resin and then enters the ozone generation cell 154. The ozonated water re-enters the cartridge housing and flows through the lead abatement labyrinth in the bottom of the cartridge housing 66. The ozonated, lead abated water re-enters the fluid circuit and flows to the venturi 308. The re-circulation path 342 and ozonated water path 352 are mixed together and combine at the venturi intersection 309. The ozonated mixture then enters the return path 354 and flows into the reservoir container.

Referring to FIGS. 21A, 21B, 22A and 22B, the ozone generator 122 providing the source of the ozone for application to the water is shown. The ozone generator 122 generally includes the ozone cell 154 and the housing 366, a mechanism for actuating the ozone cell, and flow-paths for passing water past the ozone cell. The ozone cell 154 is described in detail in U.S. patent application Ser. No. 60/261,101, filed Jan. 10, 2001, which application was earlier incorporated by reference herein. A description of the ozone generator 122 is provided below also.

The ozone generator 122 includes a housing 366 having three openings therein. One opening 360 forms part of the dead-leg channel 346 to pressurize the piston 350 and actuate the ozone cell 154. Another opening 362 allows the water flowing from the DI chamber to enter the ozone cell and help the reaction to create ozone and ozonated the water. The third opening 364 leads to the lead abatement chamber which removes any lead that might have migrated into the water during the ozonation process. The housing 366 also defines a cylinder piston chamber 368 having a first diameter, a cylindrical retaining chamber 370 at the end of and opening to the piston chamber 368 having a second diameter (forming an annular spring shoulder between the two), and a diaphragm recess chamber 372 having a third, smaller diameter opening to the retainer chamber 370 (forming an annular seal wall 374 at the end of the retainer wall 376). A fourth, and smallest, cylindrical anode bore 378 extends from the diaphragm recess chamber 372. Each of these chambers have a common axial center-line.

Figure 22A:
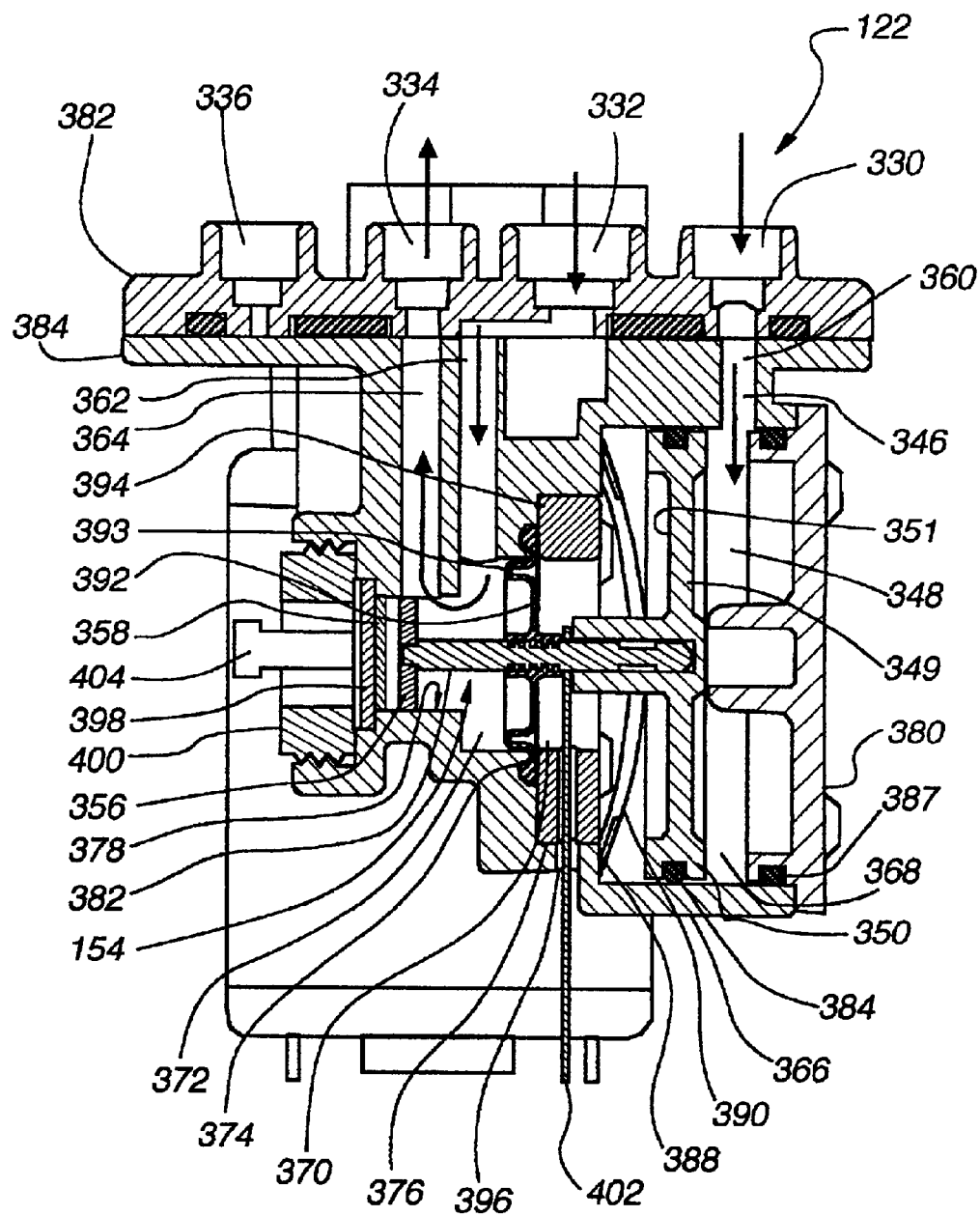
FIG. 22A is a section view taken along line 22—22 of FIG. 18, showing the ozone generator, including the cell in the non-engaged position, prior to the pressure increasing sufficiently to move said piston.
Figure 22B:
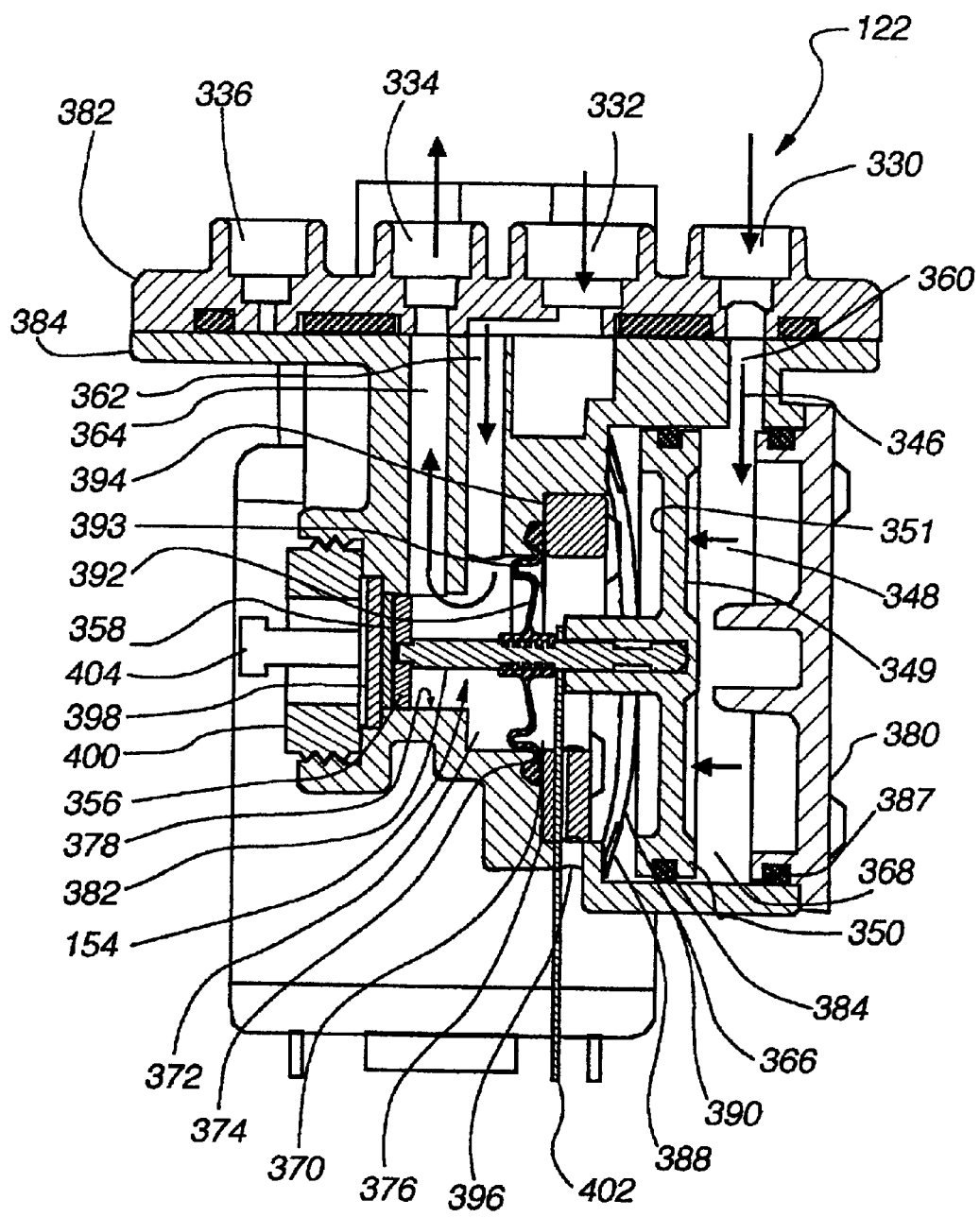
FIG. 22B is a section view similar to that of FIG. 22A, wherein said piston has been actuated by said water pressure to move and cause said cell to be in the engaged position.

A cap 380 is sealingly attached to the open end of the piston chamber 368. A rod 382 is positioned to extend down the center of the interconnected chambers and act as a piston rod. At the right end of the piston rod is fixedly attached a piston 350, which is sealingly engaged with the sidewalls of the piston chamber 368, by such means as an o-ring 384. The axial movement of the piston (and thus the rod) is defined by the engagement contact with the cap at one end (bottom dead-center) and by engagement with the annular spring shoulder 388 at the other end (top dead-center). A spring washer 390 is positioned between the piston 350 and the spring shoulder 388 to bias the piston in the bottom dead-center position against the cap 388. The pressurized side of the piston is between the piston and the cap. The first aperture 360 mentioned above allows the water to flow into the pressurized chamber and cause the piston to move from bottom dead-center (FIG. 22A) to top dead-center (FIG. 22B). This is the dead-leg channel 346, since once the piston is moved to top dead-center, the flow into this leg substantially stops except to maintain the pressure. The pressure is created by the pump 288, as described above.

A diaphragm 392 is positioned on the rod at about a mid-point along its length. The diaphragm 392 is flexible, and has a general circle shape with one circumferential fold 393. The rod 382 extends through the center of the diaphragm 392, and is fixedly and sealably attached thereto. The diaphragm 392 is positioned in the diaphragm recess chamber 372, and the circumferential edge of the diaphragm 392 is held against the annular seal wall 374 by a retainer 394. The retainer 394 has a bore 396 formed radially therein at one location to allow any seepage past the piston 350 to leak out of the housing 366 onto the evaporation media 156.

As the piston 350 moves from bottom dead center to top dead center, the diaphragm 392 stretches, and the circumferential fold 393 extends to allow the rod 382 to move without restriction, while retaining a hermetic and watertight seal between the retainer chamber 370 and the diaphragm recess chamber 372. This keeps any water that might be contaminated with lead from migrating out of the system and into the circulation path without going through the lead abatement region.

An anode 356 (electrode) is attached to the end of the rod 382. The anode 356 is circular in shape to closely match the bore of the anode bore 378. A sealing engagement here is not needed, however. The second aperture 166 noted above (from the DI chamber portion of the cartridge) is positioned to open into the diaphragm recess chamber 372 to allow water to flow into the ozone cell.

The anode post 382 is press fit into the piston 350 making a piston/diaphragm/anode post/anode assembly (with the piston 350 oriented to the outside of the cell and the anode 356 adjacent to the center of the cell). The downstream side 351 of the piston is at atmospheric pressure.

The port 334 entering into the lead abatement region of the cartridge is also open to the diaphragm recess chamber 372 to allow the ozonated water to flow there once charged with ozone. The lead abatement port 334 is the exit path for the water from the ozone cell 154. The operation of the ozone cell 154 causes the oxygen and ozone to form in the chamber adjacent the anode 356, and as this chamber is full of water, the ozone is introduced to the water and swept with it (under the flow caused by the pump 288) up the exit port 334 and into the lead abatement chamber. The hydrogen migrates to the cathode 398 and dissipates into the air beyond the cathode 398.

A cathode 398 is held in position at the end of the anode bore 378 by a cylindrical retainer 400. The cathode 398 has the membrane 358 (proton exchange membrane) attached to the surface exposed to the anode 356. When the piston 350 is moved to the top dead-center position, the anode 356 contacts the membrane 358. An electrical contact is made to the anode post by a metal stampings 402 attached thereto, which is in turn connected to the power supply through the control unit. An electrical contact is made to the cathode 398 by a metal stamping 404 attached thereto (trapped between the retainer and the cathode), which is in turn connected to the power supply through the control unit. The control unit energizes the cell as appropriate to start producing ozone when the anode 356 contacts the membrane 358.

As mentioned above, the gear pump 288 causes water to flow against the upstream side 349 of the piston 350 thereby causing pressure to build against the upstream side of the piston. The pressure on the upstream side 349 of the piston 350 causes the piston and the anode post assembly connected to the piston to move toward top dead-center. The anode 356 attached to the end of the post assembly is pushed into contact with a proton exchange membrane 358. The proton exchange membrane 358 is connected to a cathode 398. Both the anode post and the anode are preferably constructed of titanium to prevent their oxidation in an ozone environment. The anode 356 is fabricated using porous titanium to allow the ozone and oxygen created by the operation of the ozone cell 154 to flow through the anode 356. The diaphragm 392 is fabricated from an ozone resistant material (e.g., silicone rubber). The diaphragm 392 forms a pressure seal within the cell. On the upstream side of the diaphragm (the piston end), pressure builds to 20–30 psi during operation. On the downstream side 351 of the piston 350 (the anode end), the pressure remains at atmosphere at all times. Because the pressure on the downstream side 351 remains at atmosphere, the reaction chamber 154 is full of water at all times (in and out of operation) and the velocity of the water flowing through the generation cell is reduced. Because the water flow through the generation cell at a slower rate than if under pressure, the water has a greater contact time with the ozone being generated and thereby becomes ozonated more efficiently. The anode 356 is electroplated to include lead dioxide (lead dioxide is used as a catalyst in the ozone generation cell).

When the anode 356 contacts the proton exchange membrane 358, the electrical circuit is completed and the ozone cell 154 is activated (according to the control unit) to start producing ozone. As water flows through the current formed by the electrodes, the water is dissociated into hydrogen, oxygen, and ozone gases. When the motor 286 is turned off, thereby causing the gear pump 288 to stop, the pressure on the diaphragm 392 is reduced to zero. At that time, the piston spring 390 causes the piston 350 and anode 356 to return to their default positions with the anode 356 no longer in contact with the proton exchange membrane 358. This makes the electrical circuit no longer complete, and the ozone generation is turned off.

On the cathode side of the generation cell, a proton exchange membrane 358 is sealed against the interior wall of the generation cell by the cathode. A negative electrical stamping 404 makes the electrical connection to the cathode 398. The negative electrical stamping 404 includes an arm that extends from the side of the generation cell and is connected to a power source. The proton exchange membrane 358, cathode 398, and negative electrical stamping 404 are retained in the generation cell chamber 154 by screwing in the cathode plug retainer 400.

When the system is actuated, electrical current runs from the negative and positive electrical stampings to the cathode 398 and anode 356, respectively. Because the cathode 398 and proton exchange membrane 358 are in contact with one another, the electrical current is transferred to the proton exchange membrane 358. When the anode 356 and proton exchange membrane 358 contact one another (when the cell is actuated, see FIG. 22B), the electrical circuit is completed and generation of the ozone gas begins. The negative stamping 404 also serves as a lock washer to help ensure that the cathode plug 400 stays secured to the cell chamber 154.

Water pressure (created by the pump described above) applied to the piston 350 on the opposite side of the piston spring forces the piston/diaphragm/anode post/anode assembly until it bottoms out on the proton exchange membrane 358 (PEM). In one embodiment a pressure of 20–30 psi builds on the up-stream side 349 of the piston 350 and causes the piston to move approximately 0.07 to 0.08 inches to contact the PEM. In one embodiment, the piston spring 390 is a 3-coiled wave washer. The contact of the anode 356 against the PEM completes the electrical circuit, which starts the electrochemical production of ozone. Water traveling though the cell chamber of the lower manifold 284 transfers the ozone gas to the remainder of the water circuit (discussed further below).

Figure 21A:
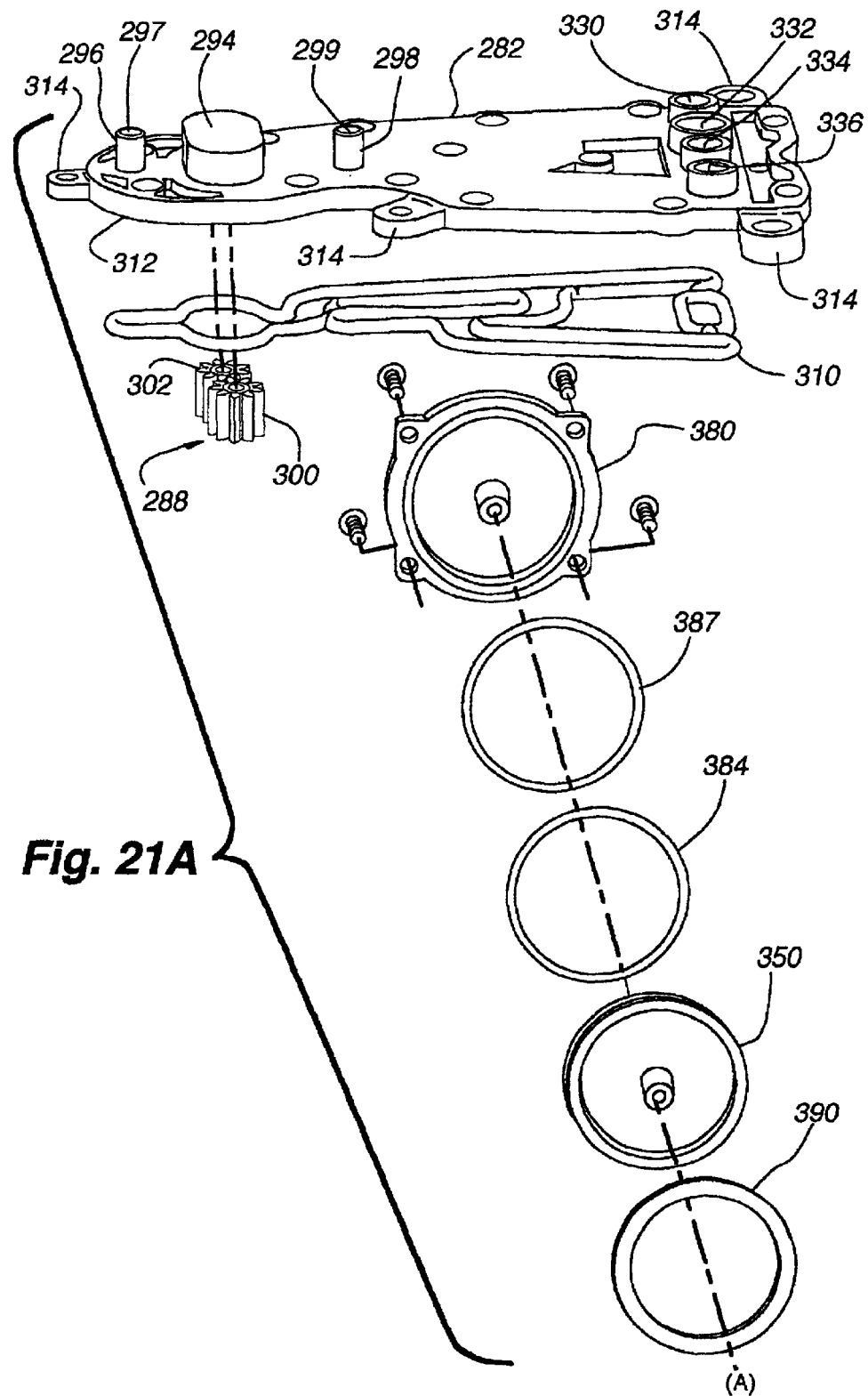
FIGS. 21A and B is an exploded view of the manifold, showing the seal member, pump, ozone generator and cell.
Figure 21B:
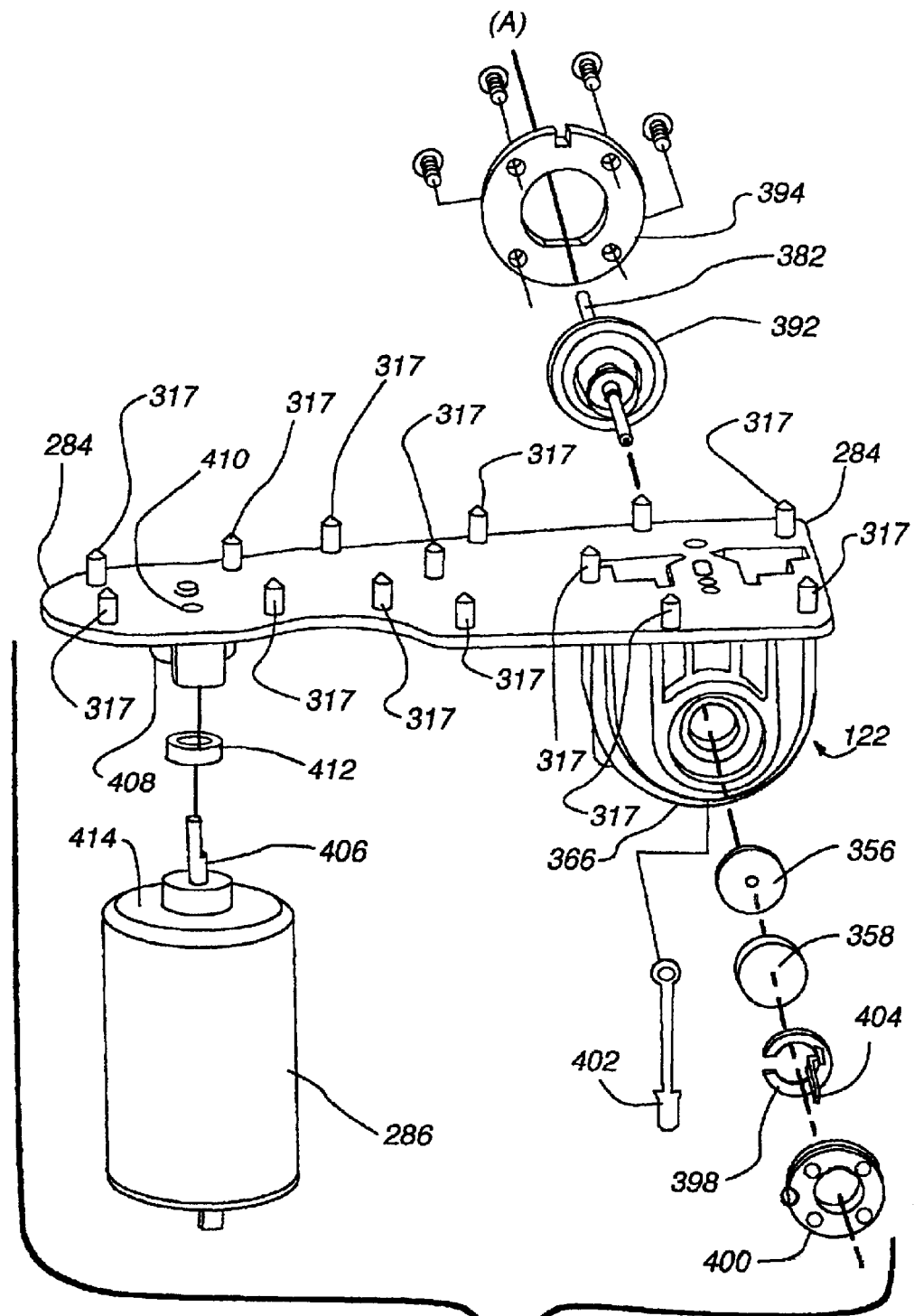

As also illustrated in FIG. 21B, the motor 286 is connected to the end of the lower manifold 284 at the opposite end of the manifold from the ozone generator 122. The motor 286 cooperates with the gears to form a gear pump 288. The motor shaft 406 extends up into a receiving collar 408 and aperture 410. The aperture 410 is configured to allow the shaft 406 to be received by a corresponding aperture in one of the gears 300, see FIG. 21A, retained in the gear pump housing 294. The motor shaft 406 operates to turn the gear 300. The teeth on the first gear 300 are inter-engaged with teeth on a second, free-wheeling gear 302 thereby causing said second gear 302 to turn also. FIG. 21A shows the gear engagement. The resulting gear pump 288 creates pressure with low flow volumes. Alternative pump assemblies could be utilized providing they also are able to increase pressure within a channel that has a low flow volume. A shaft seal 412 fits around the motor shaft 406 and in between the top surface 414 of the motor 286 and the interior surface of the receiving collar 408. The shaft seal 412 prevents any water from migrating from the gear pump housing 294 in the upper manifold 282 to the receiving collar 408 thereby preventing leakage in this area.

While the present invention has been described as a unit that sits on a counter top, it is contemplated that the base unit could be built into an appliance, such as a clothes washer, clothes drier, dishwasher, refrigerator, cabinet, or sink. The base unit could be built into a counter top, or be permanently mounted below a cabinet or in a cupboard.

Generally, the device is constructed by connecting the circuit board and ozone generator to the underside of the upper housing portion, connecting a power source and power source leads to both the ozone generator (negative and positive stampings) and to the motor, and placing the upper housing portion over the lower housing portion. The upper and lower housing portions can be connected to one another using a detent-type structure, hot plate welding, epoxy, or similar means. The control panel is then fixed to the front shelf portion of the upper housing portion (the control panel is operably connected to the circuit board).

The control panel includes buttons that the user can press to select their desired mode of operation for the device. The control panel is operably connected to a circuit board. The circuit board includes memory means that store device process flow software, a clock for timing the flow, and other necessary control instructions. These features are generally well known in the art, but are part of a unique combination as used here. The combination of the control panel, circuit board, and device process flow software are operably connected to the device components and serve to control the operation of the device.

Figure 23:
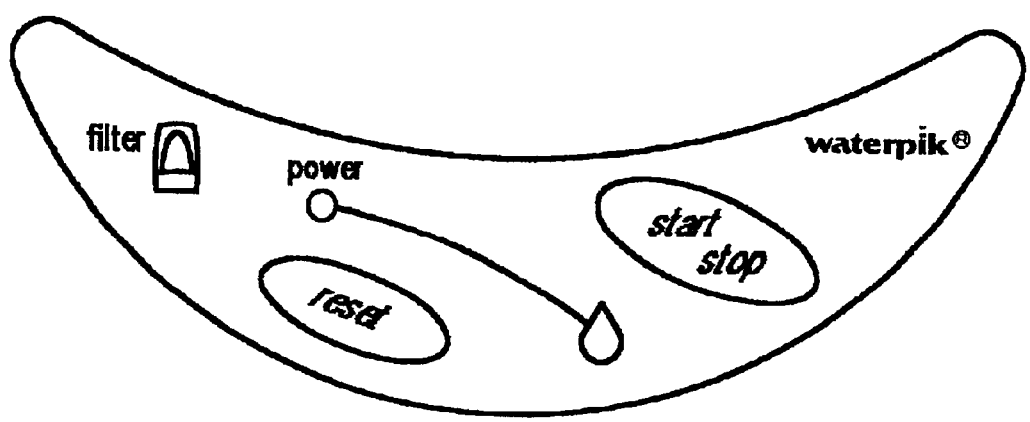
FIG. 23 shows a control panel overlay.

In a first embodiment for spray bottle use and corresponding to the control panel illustrated in FIG. 23, the control panel includes the following buttons and light emitting diodes (LEDs): filter status LED; reset button; start/stop button; power on and 2-minute timer LED; and an ozonated water timer LED. In one embodiment, both the filter status LED and the ozonated water timer LEDs are one color (the filter status is red and the ozonated water timer is green), and the power on and 2-minute timer LED is two color (orange/green). Alternative embodiments may use different colors for the LEDs.

Figure 24:
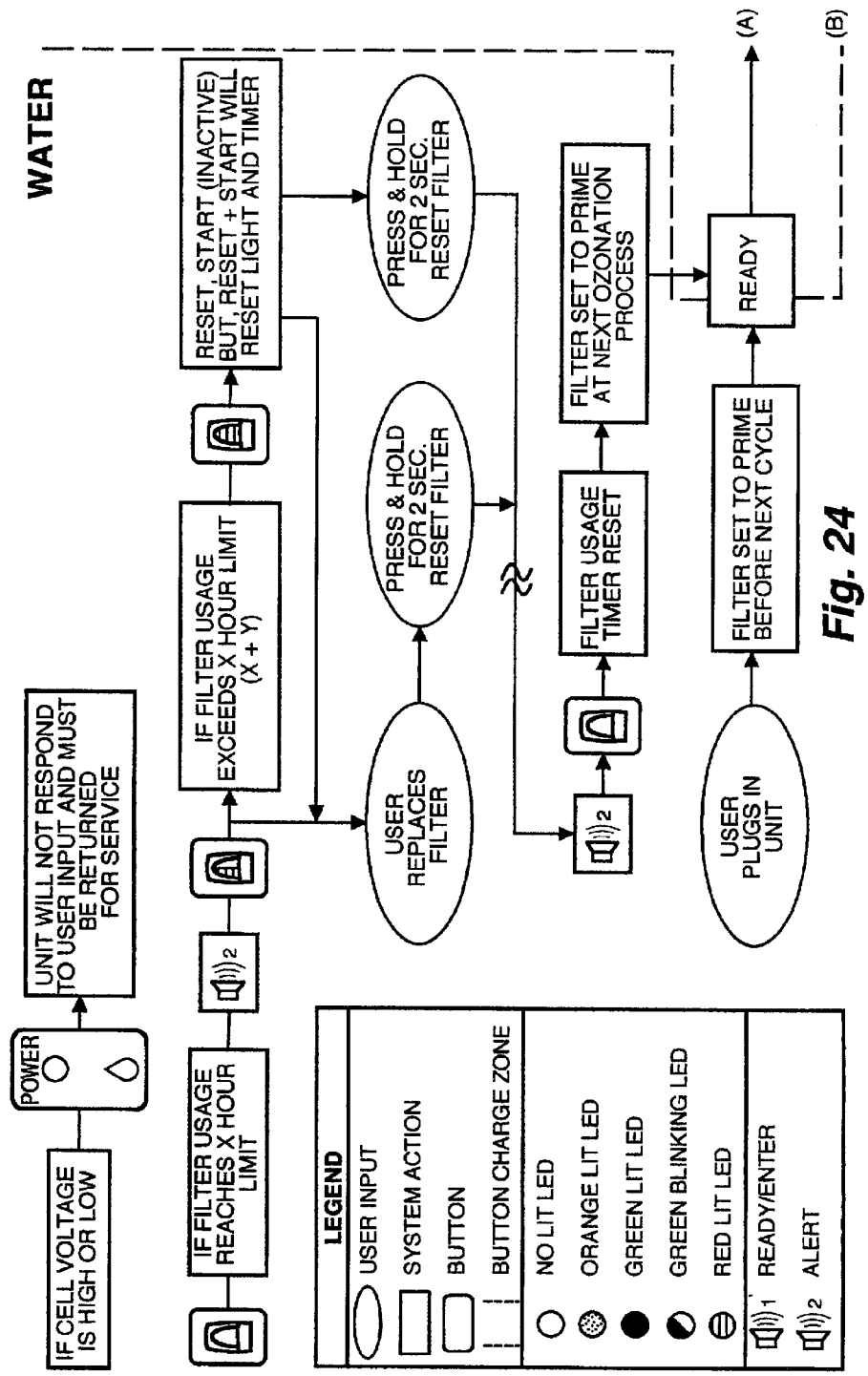
FIGS. 24–28 show the block diagram showing the operation steps used by the control unit in controlling the inventive device, correspond to the control panel overlay shown in FIG. 23.

FIGS. 24–28 illustrate the process flow for the first embodiment and correspond to the control panel in FIG. 23. In the first embodiment, the user operates the present invention device by first plugging the device into an electrical outlet (or by providing the required power source, which may include batteries) and turning the power button or switch to an on position (some embodiments may not include a power button or switch but instead will either maintain a continuous on status, or will power on under other circumstances, such as when the reservoir is filled or placed on a base). Next the user must fill the respective reservoir container (i.e., spray bottle or carafe) with water and place it in the recess on the base of the main housing, the user can check the operational status of the device by viewing the color of the control panel buttons or LEDs. Turning now to FIG. 24, a power LED that is green and blinking indicates that the cell voltage is either high or low and the unit will not respond to user input, in which case the system should be returned to the manufacturer for service. However, if the power LED is orange, it is an indication that the filter has been set to prime before the next cycle and the unit is ready to operate.

Upon starting the device, the device process flow software will also check the filter status. If the filter usage has reached a preset accumulated usage time limit (generally measured in hours), an audible alarm sounds and half of the filter status LED lights in red. The user will be required to replace the filter and press and hold the reset button for 2 seconds to reset the filter. After replacing the filter and resetting the filter, the filter status LED will return to an unlit state, the filter usage timer will reset to zero, and the filter will be set to prime at the next ozonation process. At this point, the power LED should be orange indicating the unit is ready to operate.

If the filter usage has exceeded a preset accumulated time limit by a certain preset amount (X+Y hours), an audible alarm sounds and the filter status LED fully lights in red. For example, if the filter preset accumulated time limit is 10 hours, the X+Y alarm may be programmed to activate if the user goes past the preset limit by more than twenty-percent (2 hours) thereby causing the alarm to activate at 12 hours. A fully lit filter status LED will cause both the reset button and the start button to become inactive. To reset the light and usage timer, the user presses both the reset button and the start/stop button at the same time. Pressing the reset button alone will not affect the operation of the unit in any way. In normal operation, the user would replace the filter and press and hold the reset button for 2 seconds to reset the filter. After replacing the filter and resetting the filter, an audible alarm will sound and the filter status LED will return to an unlit state, the filter usage timer will reset to zero, and the filter will be set to prime at the next ozonation process. At this point, the power LED should be orange indicating the unit is ready to operate.

However, the user could continue to use the unit without replacing the filter by simply pressing and holding the reset button for 2 seconds to reset the filter after pressing both the reset button and the start/stop button at the same time (instead of replacing the filter in between). The filter status LED will return to an unlit state, the filter usage timer will reset to zero, and the filter will be set to prime at the next ozonation process. At this point, the power LED should be orange indicating the unit is ready to operate.

If the power LED is not orange, the user can do one of two things. The user can either push the start button to see if the device will operate regardless of the color of the power LED or the user can simultaneously press the reset+start buttons and press and hold the reset button for 2 seconds. In the latter case, the power LED should then light in orange indicating the unit is ready to operate.

Whether or not the power LED is orange, when the user presses the start button, the device operates based on instructions from the device process flow software program. The beginning of these instructions may be seen on FIG. 25. After the start button is pressed, the unit checks to see if a priming flag was set. If a priming flag was set, the priming cycle is activated and activation of the priming cycle is indicated on the control panel buttons. If the priming flag was not set, the unit checks the filter activity counter to see if more than X days have passed since the unit was last used. If more than X days have passes since the last use, the priming cycle is activated and such activation is indicated on the control panel buttons.

Figure 26:
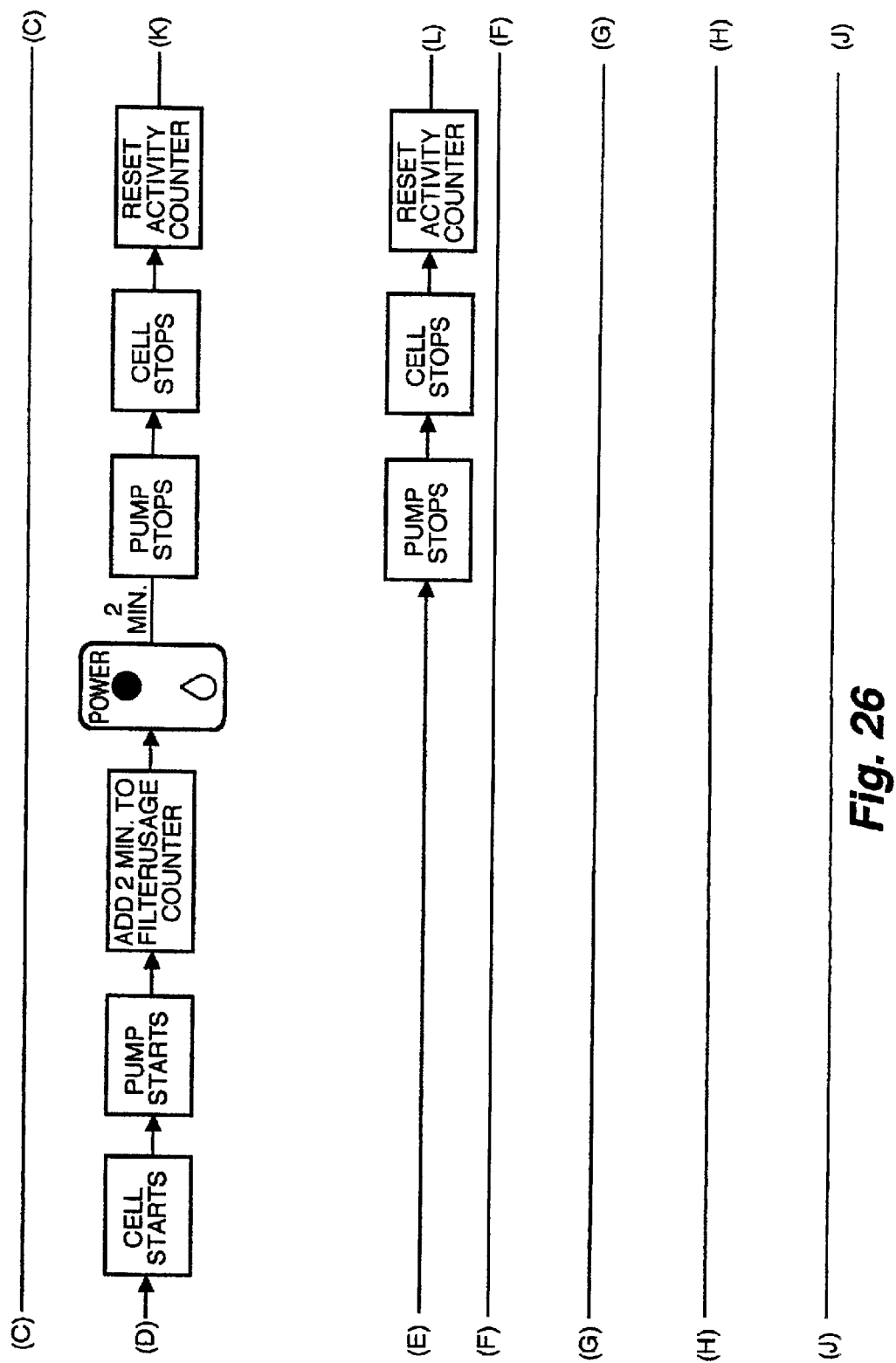
Figure 27:
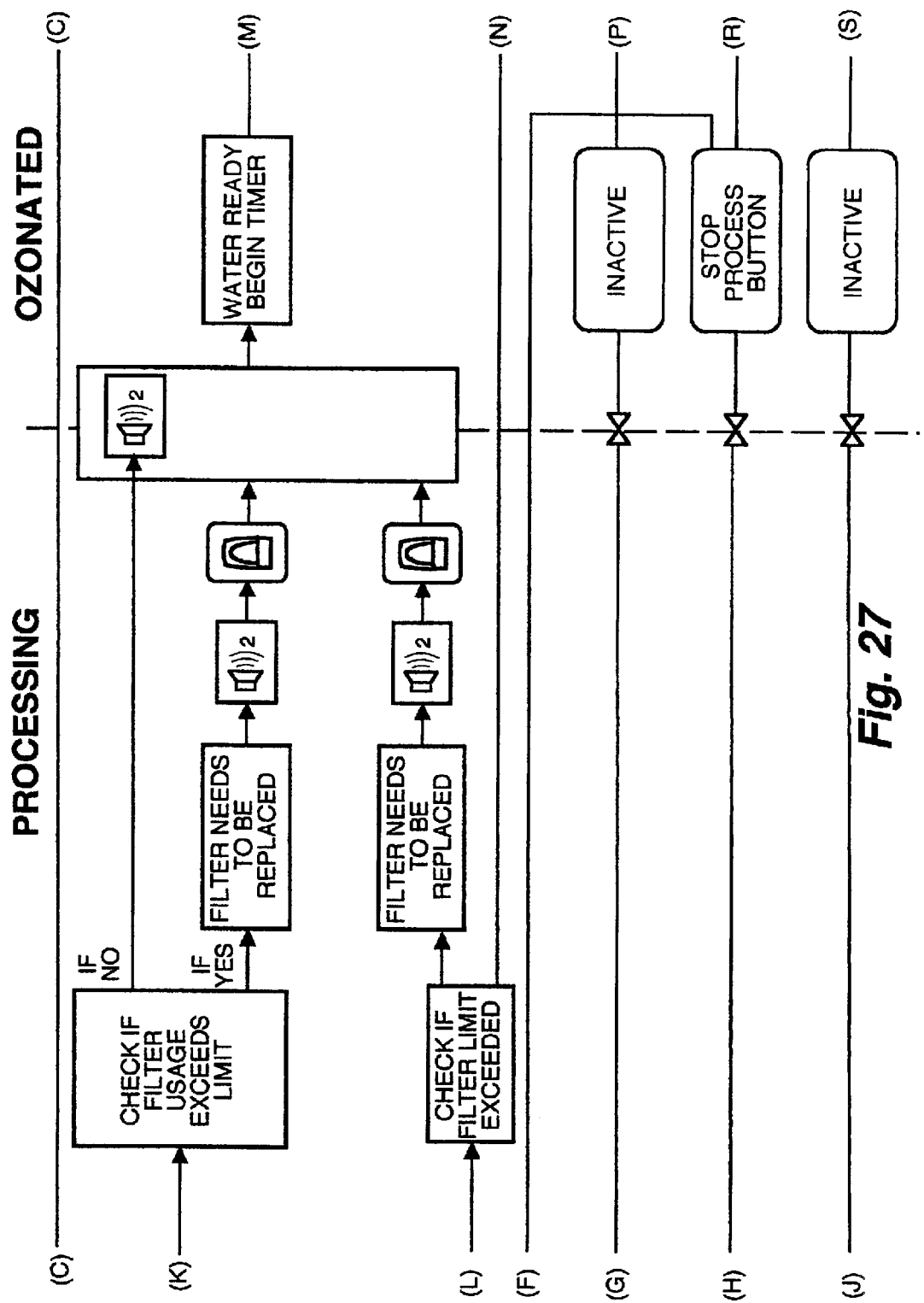
Figure 28:
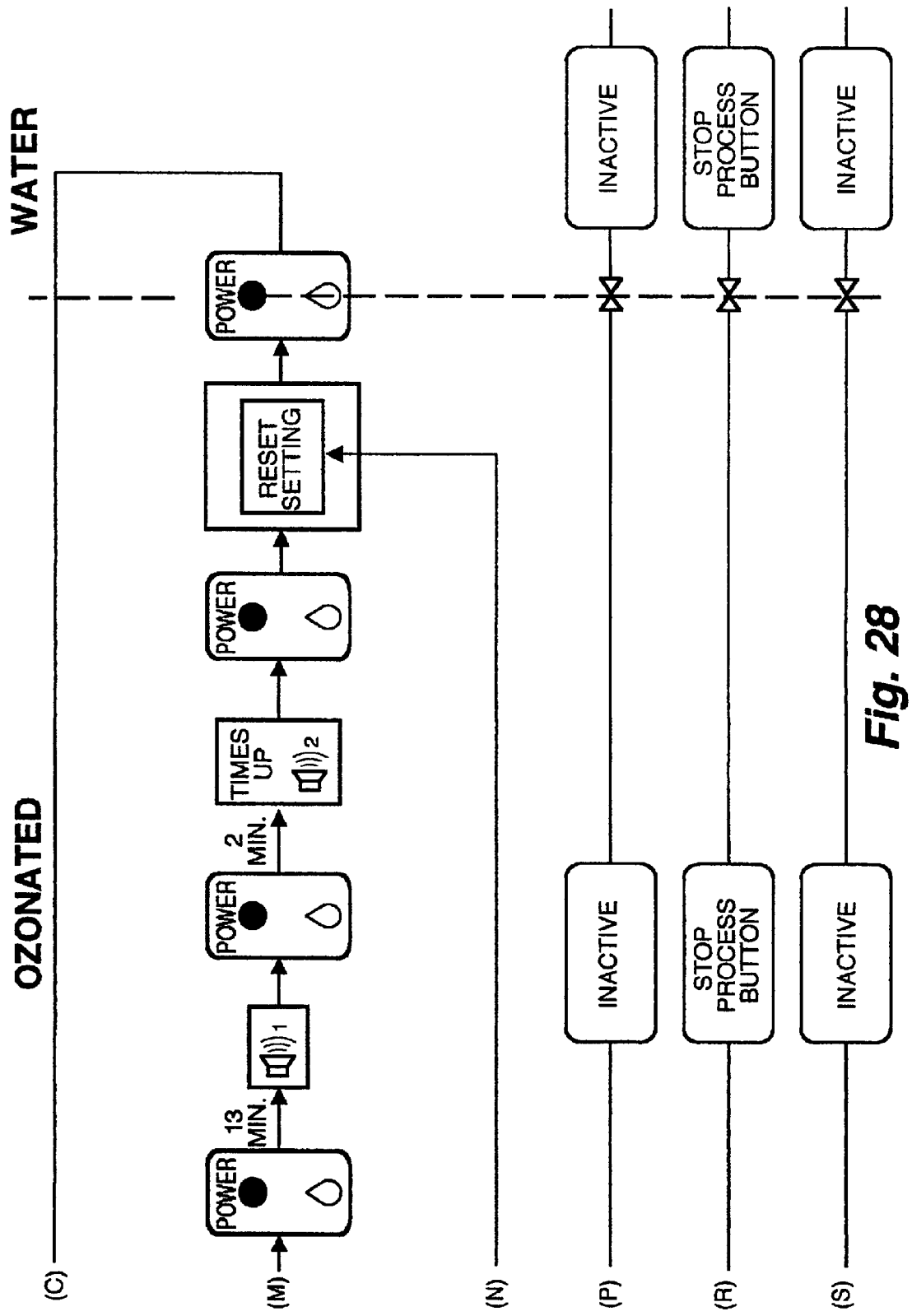

If less than X days have passed since the last use or after the priming cycle terminates, the cell starts, the pump starts, and 2 minutes is added to the filter usage counter, all as shown on FIG. 26. At this time the power LED is green. After two minutes, the pump stops, the cell stops, and the activity counter is reset. In FIG. 27, the unit then checks to see if the filter usage exceeds preset limits. If the filter usage exceeds preset limits, an audible alarm sounds and half of the filter status LED is lit in red indicating that the filter needs to be replaced. If the filter usage does not exceed preset limits, an audible alarm sounds indicating the unit is ready to begin the ozonation cycle. In either case (whether the filter usage does or does not exceed preset usage limits), at this point the water is ready for ozonation and the ozonation cycle timer begins as shown on FIG. 28. When the cycle timer begins, the power LED becomes unlit and the ozonated water timer LED lights in green. After 13 minutes, an audible alarm sounds and the ozonated water timer LED changes to a blinking green. After 2 more minutes, an audible alarm sounds and the ozonated water timer LED becomes unlit, indicating the ozonation cycle is complete. Once the cycle is complete, all control logic settings are reset to their initial setting. At this time, the power LED lights in orange indicating the unit is ready to start another ozonation cycle. The water in the reservoir container is now ready for use.

If the user presses the stop button after pressing the start button but prior to commencement of the ozonation cycle, the pump stops, the cell stops, and the unit activity counter is reset. Next, the control unit checks to see if the preset filter usage limit has been exceeded. If the filter usage exceeds preset limits, an audible alarm sounds and half of the filter status LED is lit in red indicating that the filter needs to be replaced. Whether or not the filter usage exceeds preset limits, next the power LED lights in orange indicating the unit is ready to start another ozonation cycle. This cycle is shown on FIGS. 25–27. If the user presses the start/stop button during the ozonation cycle, the unit returns to the beginning of the ozonation process as described above.

Figure 25:
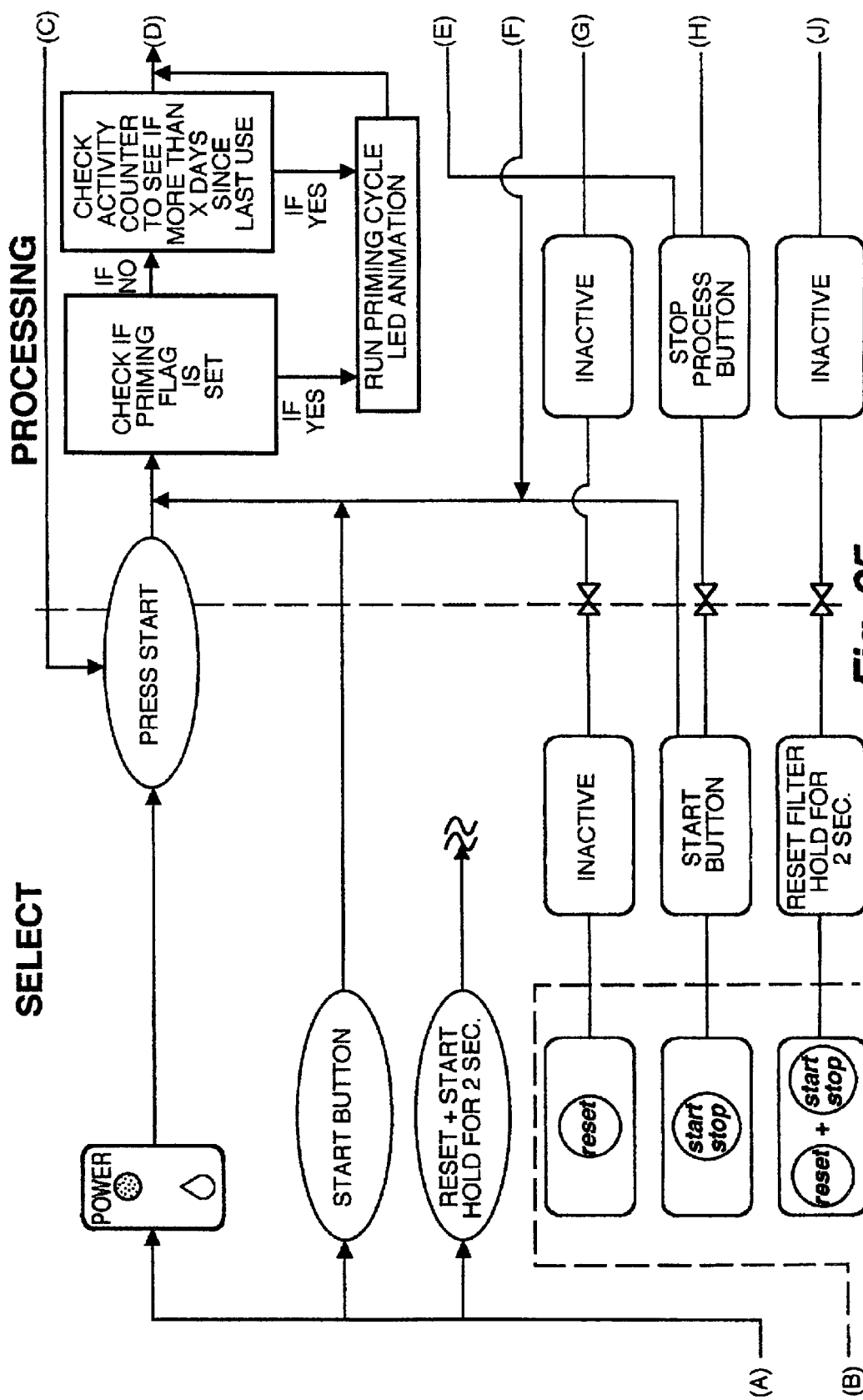

FIGS. 24 and 25 display the effects of a user simultaneously pressing the reset+start/stop buttons for at least two seconds prior to pressing the start button alone. Specifically, an audible alarm sounds, the filter status LED becomes unlit, the filter usage timer is reset, the filter is set to prime at the next ozonation cycle, and the power LED is lit in orange. If the user simultaneously presses the reset+start/stop buttons after pressing the start button alone, no event occurs, as displayed in FIG. 25.

Figure 29:
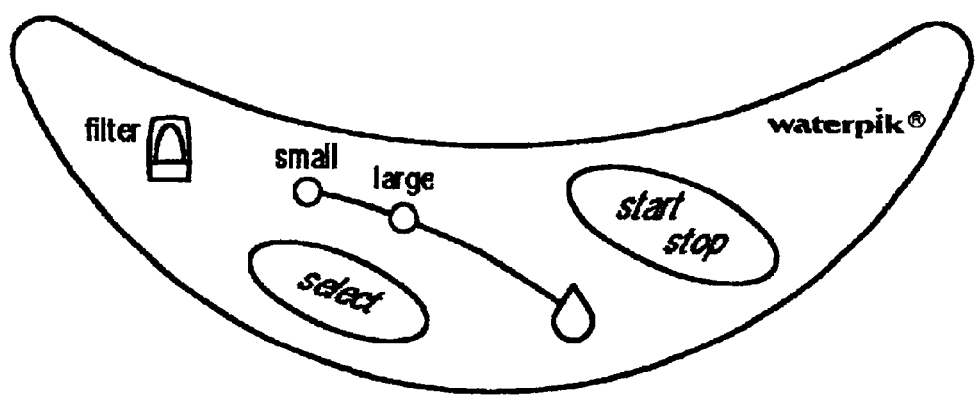
FIG. 29 shows another control panel overlay.

In a second embodiment for both spray bottle and carafe use and corresponding to the control panel illustrated in FIG. 29, the control panel includes the following buttons and LEDs: filter status LED; select button; start/stop button; small select and 2 minutes timer LED; large select and 8 minutes timer LED; and an ozonated water timer LED. In this embodiment, both the filter status LED and the ozonated water timer LED are 1 color (filter status is red and the ozonated water timer is green), while both the small select/2 minutes timer LED and the large select/8 minutes timer LED are two color orange/green. Alternate colors may be used for any of the LEDs without departing from the spirit or scope of the invention.

FIGS. 30–34 illustrate the process flow for the second embodiment and correspond to the control panel in FIG. 29. In the second embodiment, the user operates the present invention by first plugging the device into a standard 120 volt AC power socket and turning on the power switch. The user may fill the respective reservoir container (i.e., spray bottle or carafe) with water and place it in the recess on the base of the main housing. The user can check the operational status of the device by viewing the color of the control panel buttons and LEDs. If both the small select and large select LEDs are solid orange, it is an indication that the cell voltage is either high or low and the unit will not respond to user input—the system should be returned to the manufacturer for service. However, if the small select LED is orange, it is an indication that the filter has been set to prime before the next cycle and the unit is ready to operate.

If the small select LED is orange, it indicates that the unit is ready to operate with a spray bottle. If the user wants to use the unit with a carafe, the user presses the select button. Pressing the select button will cause the small LED to turn off and will light the large LED in orange indicating the unit is ready to operate with a carafe. The user can change the decision and switch to a spray bottle by simply re-pressing the select button.

Figure 30:
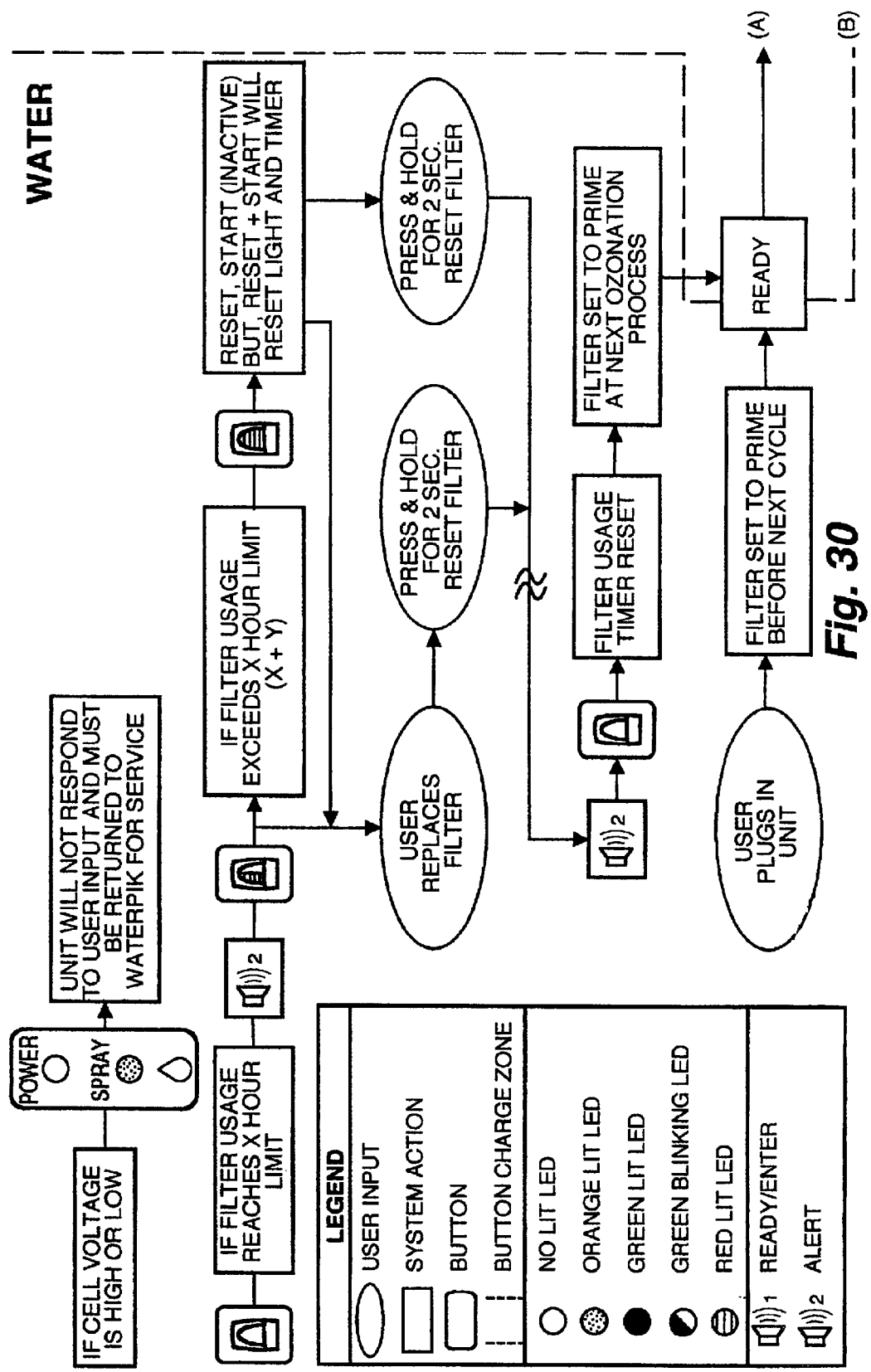
FIGS. 30–34 show the block diagram showing the operation steps used by the control unit in controlling the inventive device, correspond to the control panel overlay shown in FIG. 29.

Upon starting the device, the device process flow software will also check the filter status as shown in FIG. 30. If the filter usage has reached a preset accumulated time limit (X hours), an audible alarm sounds and half of the filter status LED lights in red. The user will be required to replace the filter and press and hold the select button for 2 seconds to reset the filter. After replacing the filter and resetting the filter, a ready signal will sound and the filter status LED will return to an unlit state, the filter usage timer will reset to zero, and the filter will be set to prime at the next ozonation process. At this point, the small LED will be orange indicating the unit is ready to operate with a spray bottle.

If the filter usage has exceeded a preset accumulated time limit by a certain preset amount (X+Y hours), an audible alarm sounds and the filter status LED fully lights in red. A fully lit filter status LED will cause both the start button and the select button to become inactive. To reset the light and timer, the user may press both the select button and the start/stop button at the same time. Pressing the select button alone prior to pressing the start button will cause the unit to switch between the small and large (spray bottle and carafe) timing cycles. Pressing the select button after the start button will not effect the operation of the unit in anyway. In normal operation, the user would replace the filter and press and hold the select button for 2 seconds to reset the filter. After replacing the filter and resetting the filter, an audible alarm will sound and the filter status LED will return to an unlit state, the filter usage timer will reset to zero, and the filter will be set to prime at the next ozonation process. At this point, the small LED may be orange, indicating the unit is ready to operate with a spray bottle. If the large LED was lit, it would be an indication that the unit is ready to operate with a carafe.

However, the user could continue to use the unit without replacing the filter by simply pressing and holding the select button for 2 seconds to reset the filter after pressing both the select button and the start/stop button at the same time (instead of replacing the filter in between). The filter status LED will return to an unlit state, the filter usage timer will reset to zero, and the filter will be set to prime at the next ozonation process. At this point, the small LED should be orange indicating the unit is ready to operate with a spray bottle. If the large LED was lit, it would be an indication that the unit is ready to operate with a carafe.

If the small LED is not orange, the user may do one of two things. The user may either push the start button to see if the device will operate regardless of the color of the small LED or the user can simultaneously press the select+start buttons and press and hold the select button for 2 seconds. In the latter case, the small LED should then light in orange indicating the unit is ready to operate with a spray bottle. If the large LED was lit, it would be an indication that the unit is ready to operate with a carafe.

Figure 31:
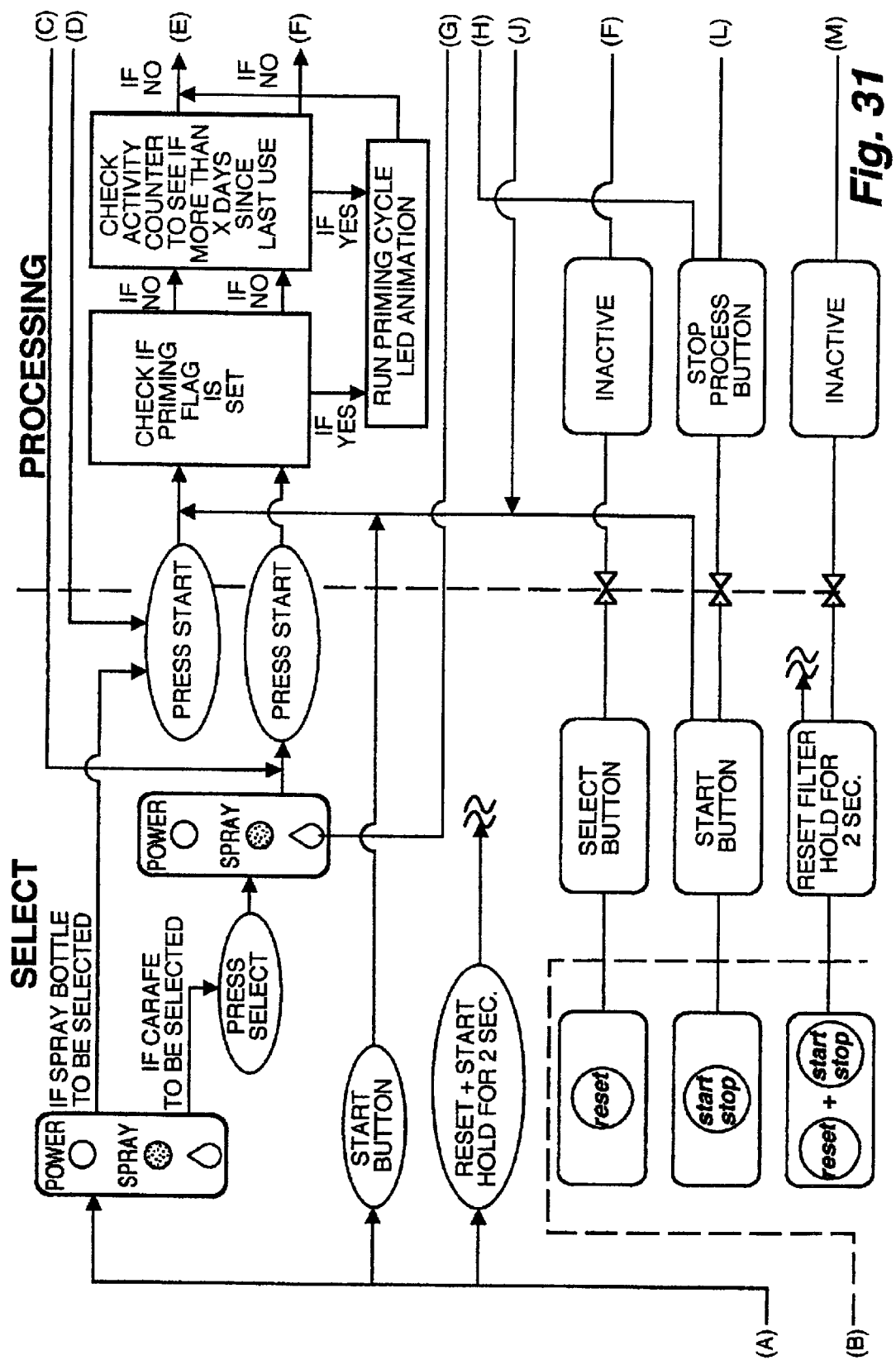

Whether or not either the small or large LEDs are lit in orange, when the user presses the start button, the device operates based on instructions from the device process flow software program. The beginning of this process is shown in FIG. 31. After the start button is pressed, the unit checks to see if a priming flag was set. If a priming flag was set, the priming cycle is activated and activation of the priming cycle is indicated on the control panel buttons. If the priming flag was not set, the unit checks the filter activity counter to see if more than X days have passed since the unit was last used. If more than X days have passes since the last use, the priming cycle is activated and such activation is indicated on the control panel buttons.

Figure 32:
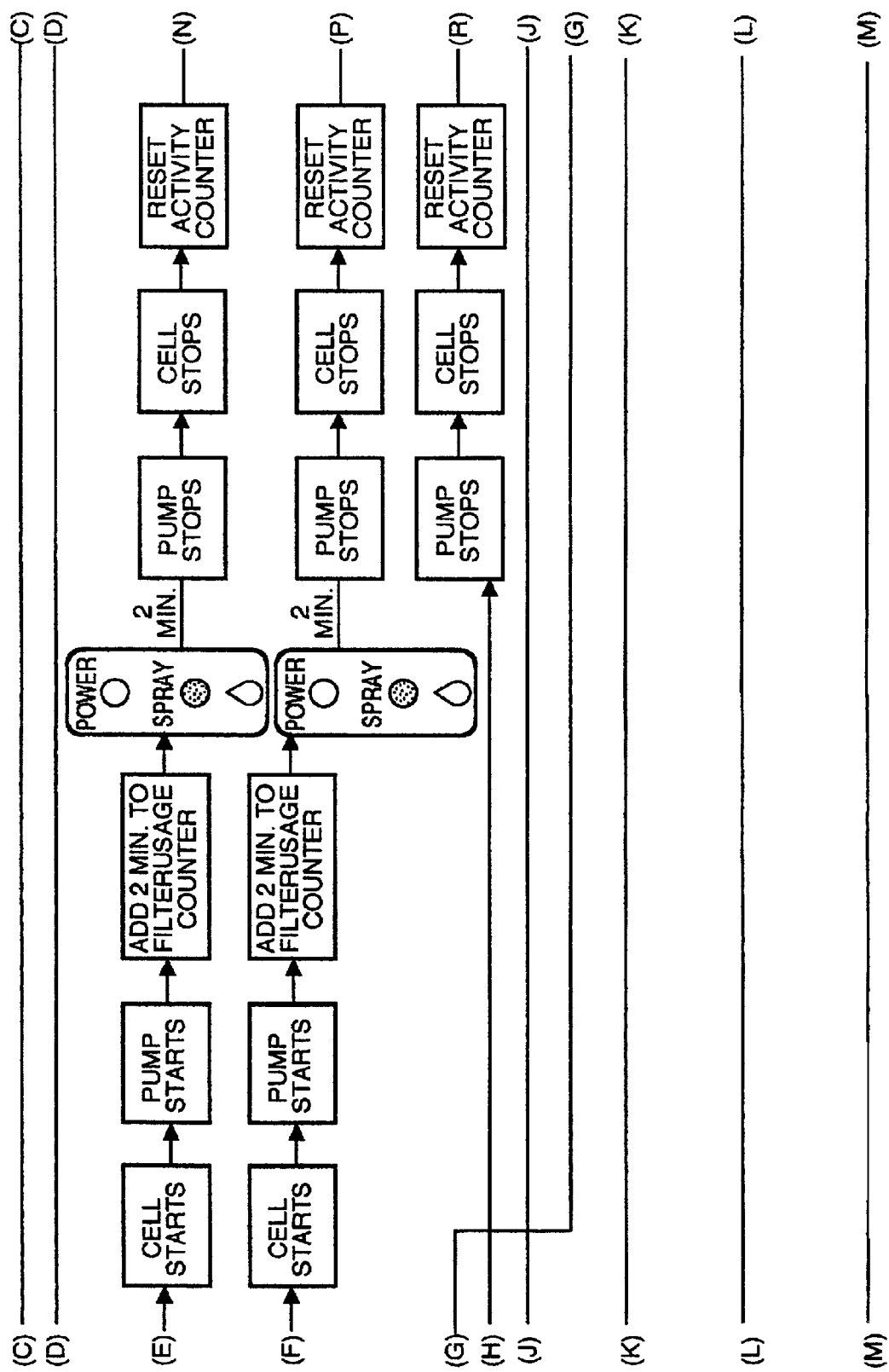
Figure 33:
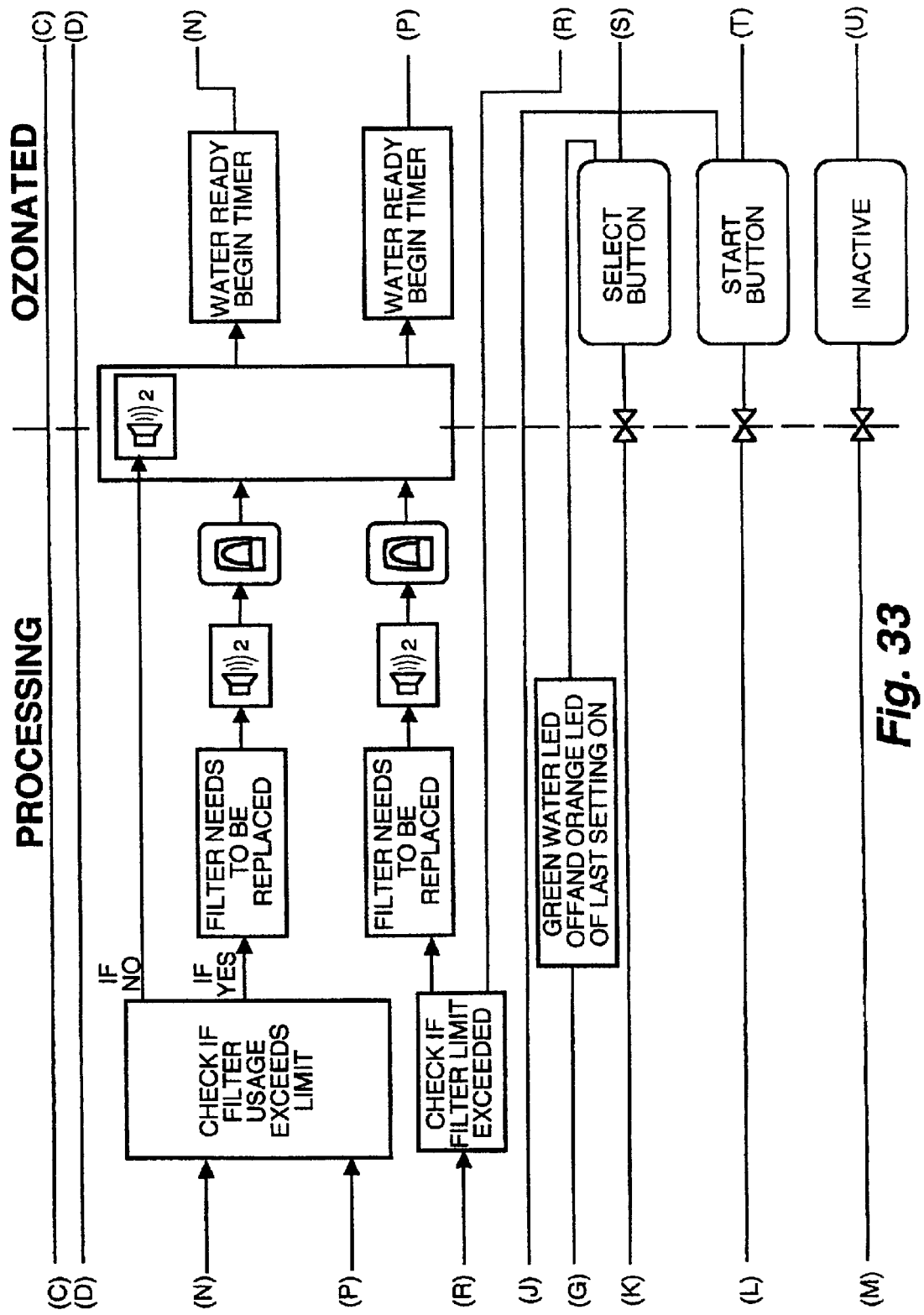
Figure 34:
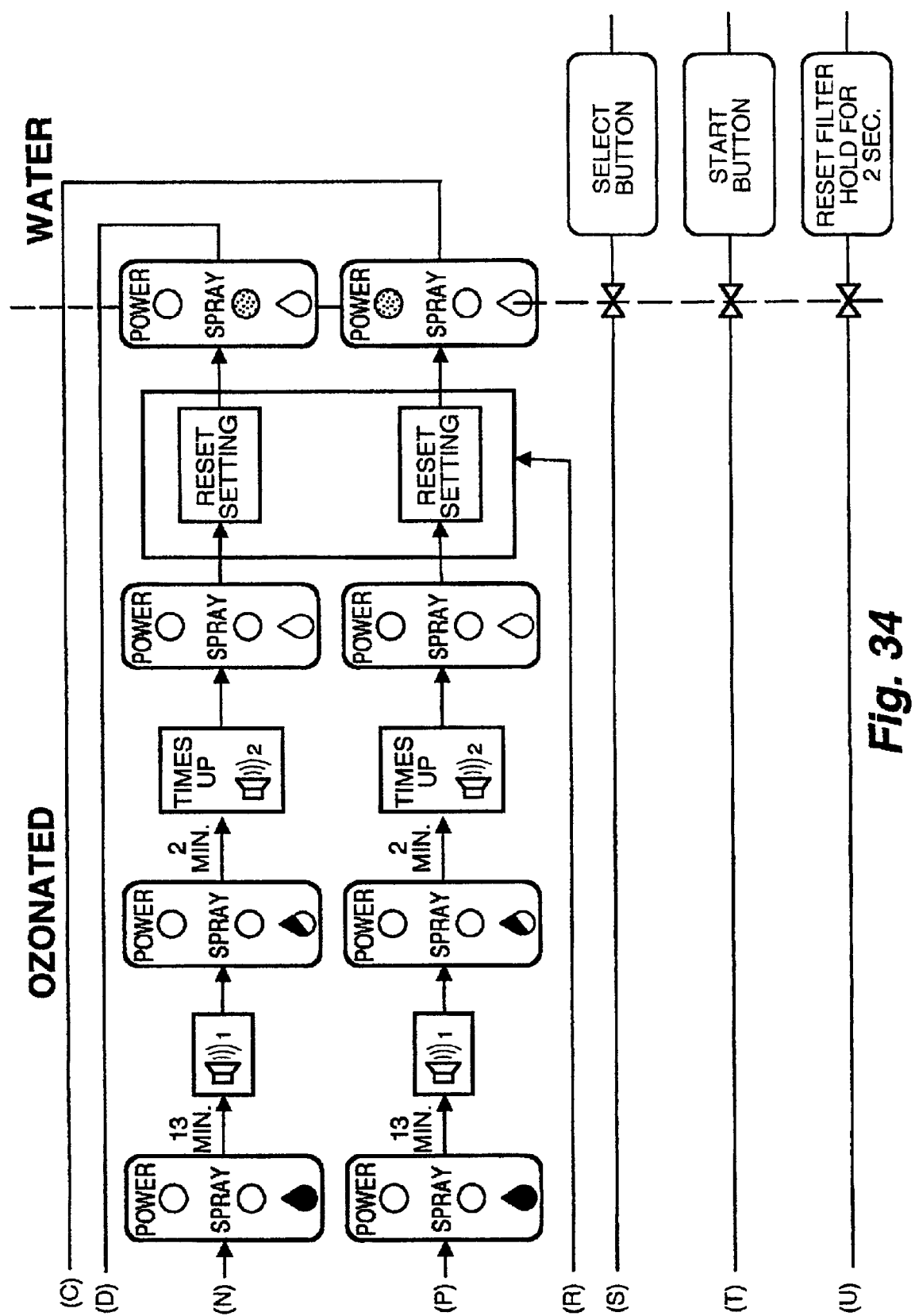

Turning now to FIG. 32, if less than X days have passed since the last use or after the priming cycle terminates, the cell starts, the pump starts, and time is added to the filter usage counter. If the spray bottle (small LED) was selected, 2 minutes are added to the filter usage counter. If the carafe (large LED) was selected, 8 minutes are added to the filter usage counter. At this time either the small LED or the large LED is solid green. After two or eight minutes (depending on whether small or large cycle is selected), the pump stops, the cell stops, and the activity counter is reset. The unit then checks to see if the filter usage exceeds preset limits, as shown in FIG. 33. If the filter usage exceeds preset limits, an audible alarm sounds and half of the filter status LED is lit in red indicating that the filter needs to be replaced. If the filter usage does not exceed preset limits, an audible alarm sounds indicating the unit is ready to begin the ozonation cycle. The water in the reservoir container is now ready for use.

In either case (whether the filter usage does or does not exceed preset usage limits), at this point the water is ready for ozonation and the ozonation cycle timer begins. This process is displayed in FIG. 34. When the cycle timer begins, the cycle size (small or large) LED becomes unlit and the ozonated water timer LED lights in green. After 13 minutes, an audible alarm sounds and the ozonated water timer LED changes to a blinking green. After 2 more minutes, an audible alarm sounds and the ozonated water timer LED becomes unlit indicating the ozonation cycle is complete. All control logic settings then return to their default state. At this time, the originally selected cycle size LED (small or large) lights in orange indicating the unit is ready to start another ozonation cycle.

If the user presses the stop button after pressing the start button but prior to commencement of the ozonation cycle, the pump stops, the cell stops, and the unit activity counter is reset, as shown in FIGS. 31 and 32. Next, the unit checks in FIG. 33 to see if the preset filter usage limit has been exceeded. If the filter usage exceeds preset limits, an audible alarm sounds and half of the filter status LED is lit in red indicating that the filter needs to be replaced. Whether or not the filter usage exceeds preset limits, the originally selected cycle size LED (small or large) lights in orange indicating the unit is ready to start another ozonation cycle. If the user presses the start/stop button during the ozonation cycle, the unit return to the beginning of the ozonation process as described above.

If the user simultaneously presses the select+start/stop buttons for at least 2 seconds prior to pressing the start button alone, an audible alarm sounds, the filter status LED becomes unlit, the filter usage timer is reset, the filter is set to prime at the next ozonation cycle, and the small LED is lit in orange. This process is detailed in FIGS. 30 and 31. If the user simultaneously presses the select+start/stop buttons after pressing the start button alone, no event occurs.

If the user is required to run a priming cycle, the user pours the contents of a charge bottle (typically provided by the manufacturer) into the port in the cartridge housing recess on the rear portion of the device main housing. The charge solution wets the proton exchange membrane (PEM) and the cathode. Both the PEM and cathode should be wet to operate. A unit should be primed prior to its first use or after long periods of inactivity.

Figure 35:
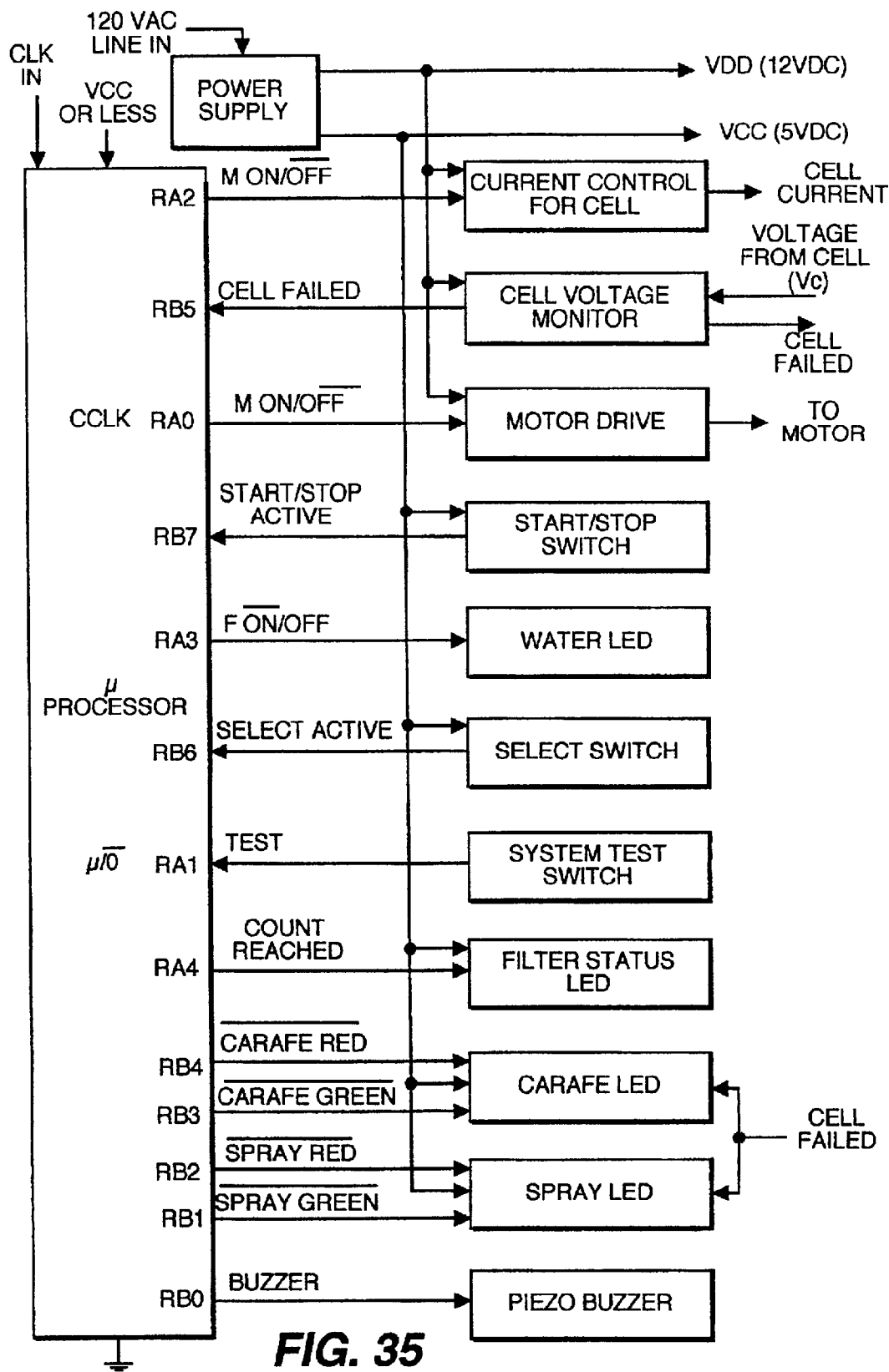
FIG. 35 is the functional block diagram of the control system.

One embodiment of the electric circuit for the spray bottle/carafe interface with the system base unit is illustrated in FIG. 35. The circuit is driven by a 12 volt 4 amp power supply, powered by 120 volt 60 Hz standard wall power. The system is controlled by a microcontroller, such as the PIC 16CE 625 microcontroller manufactured by Durable Metals of China. Of course, alternate embodiments may use different microcontrollers or microprocessors. All 13 I/O lines are used to control the various peripheral functions. The current control for the cell may be a servo type design that will precisely control the value of current being delivered to the cell. This function is controlled via the voltage reference (Vref) function of the microcontroller. This allows for 16 unique steps of current in 100 mA steps. The cell voltage monitor reports if the cell voltage has exceeded 5 volts DC or gone below 1.8 volts DC via a logic level line back to the micro controller. The motor drive is comprised of a logic level controlled transistor, such as a MOSFET, acting as a switch to turn the motor on and off. The start/stop switch is merely a switch pulled to ground that will cause an interrupt when pressed. The appropriate actions will be taken in response to pressing the start/stop switch depending on the present operating state of the device. The select switch functions identically to the start/stop switch but is used to select the bottle. The filter status LED is a standard ultra bright red LED that is used to inform when the system filter's useful life has expired. The carafe LED is used to indicate that the carafe is the currently selected bottle. The spray LED is used to indicate that the spray bottle is the currently selected bottle. The piezo buzzer is a standard buzzer that is driven by a pulse width modulation (PWM) signal from the microcontroller. The buzzer is used to inform the consumer that various locations have been reached or concluded in the device function. The water LED is used to assist in informing the user how much time is left to use the ozonated water. The system test switch is held down on power up to cause the system to enter a state whereby the LEDs and switches may be tested.

In summary, in both embodiments (spray bottle and carafe/spray bottle), there are at least the following counters and/or timers: a filter usage counter for keeping track of the overall accumulated timed use of a filter; an activity counter for keeping track of the amount of time that has elapsed since the last use of the filter; and an activity timer for timing process cycles.

Alternate embodiments of the present invention have also been contemplated. In one alternate embodiment, no deionization means are included in the system. Instead, deionized or distilled water is obtained and poured into the reservoir container and then pumped directly into the ozone generator rather than including DI means to pre-treat tap water. The water is then ozonated and run through lead abatement means.

In yet another embodiment, the device does not include a pump or a venturi. The ozone instead bubbles up from the generation cell into the reservoir container through a hydrophobic membrane. Because no pump exists in such an embodiment, actuation means such as a cam/lever arrangement can be utilized to actuate the ozone cell. The water in the reservoir container becomes ozonated after a predetermined amount of time and the ozone generator is turned off. In such a system, no piston is needed because the system is mechanically actuated rather than actuated by fluid pressure build-up.

In still another embodiment, the system may include both a pump for drawing water through the ozone generator and a separate arrangement for actuating the ozone cell. In such a system, no piston assembly is required. Instead, a separate arrangement for actuating the ozone cell may be included. Such arrangements will typically be mechanical in nature. However, alternative arrangements for actuating the ozone cell that are both non-mechanical and do not incorporate a piston assembly are generally acceptable providing they cooperate with the system pump.

Any ozone generator can be utilized in the present invention device to ozonate water in the fluid circuit described herein. Other suitable ozone generators incorporate the corona discharge and ultraviolet means to generate ozone. However, the method of generating ozone described above is preferred because it generally provides a higher weight percentage of ozone to oxygen (approximately 5–10%) than other ozone generation methods, and requires less energy.

Although the present embodiments have been described with respect to the modification of water with ozone, other liquid media, such as vinegar, can also be similarly modified to produce liquid media with increased oxidative properties. Additional contemplated applications include the modification of acids to per-acids, such as acetic acid to peracetic acid. Depending on the properties of the liquid media selected, the reaction cell device creating the increased oxidative properties may or may not have to modified accordingly.

The present invention device provides an ozonated water system that is both inexpensive and easy to install (i.e., does not require a plumber or disruption of water service). The present invention device produces ozonated water that is readily mobile and can be easily transported and used at multiple locations. The present invention device is capable of ozonating water in a container ready for uses such as a spray bottle or carafe thereby increasing the overall cleaning effectiveness of the ozonated water.

Figure 36:
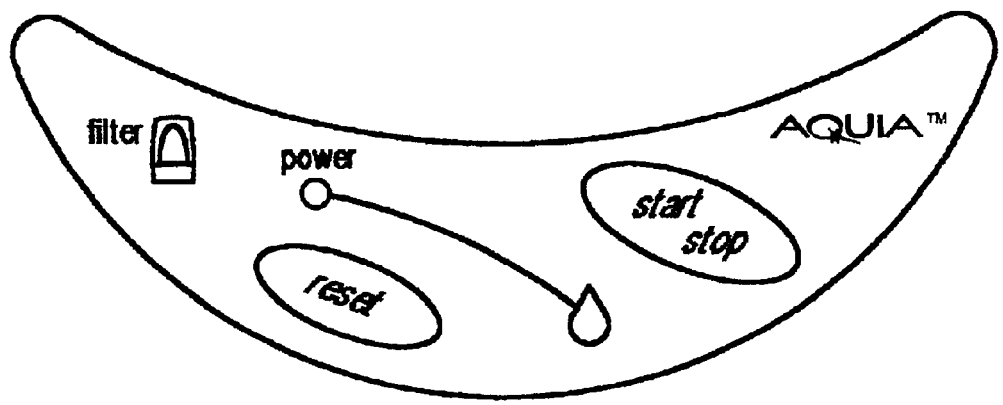
FIG. 36 is another control panel overlay.

FIG. 36 displays another control panel for use with a device embodying the present invention. The control panel generally accepts user input for operation of the device, as well as status light emitting diodes (LEDs) providing user feedback. The control panel is operably connected to a circuit board. The circuit board generally includes memory means for storing control logic, a clock capable of timing flow, and additional control instruction. These features are generally well known in the art, but form part of a unique combination as used in the present invention. The combination of the control panel, circuit board, and control logic are operably connected to the various device components and serve to control the operation of the device.

The control panel generally includes a power LED, and water LED, a filter LED, a reset button, and a start/stop button. Generally, the filter LED indicates the current status of the filter, including whether the filter is due for replacement. Similarly, the power LED indicates whether the device is turned on or off, and the water LED indicates which (if any) stage of the ozonation cycle is currently underway or completed. The filter LED is typically red, while the water LED is typically green. However, alternate colors or multiple colors may be used in other embodiments without departing from the spirit or scope of the invention. Similarly, the LEDs may convey additional information beyond that listed above in some embodiments. The reset button generally permits a user to reset the device operation to a starting state, while the start/stop button toggles operation of the device under certain conditions. It should be noted that, depending on the state of the ozonation cycle, either one or both of the reset and start/stop buttons may be disabled.

Figure 37:
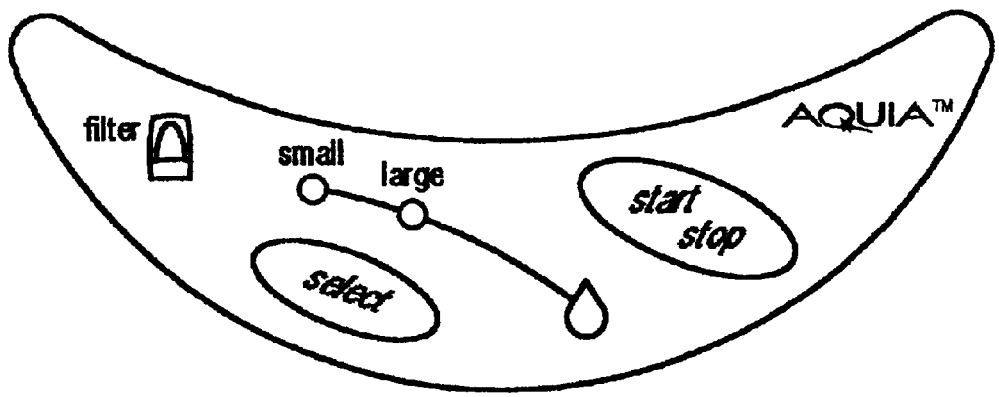
FIG. 37 is another control panel overlay.

FIG. 37 displays another second control panel for use with another device embodying the present invention. The second control panel generally operates in a fashion similar to the control panel described with respect to FIG. 36, but with several key differences. Instead of a single power LED, the second control panel includes a "small" LED and a "large" LED. Similarly, the second control panel has a select button rather than a reset button.

Generally speaking, the select button is used to toggle between two modes of operation: a small reservoir mode, and a large reservoir mode. These two modes correspond to the different reservoir sizes capable of undergoing the ozonation process. If a user desires to process a small volume of water, such as a spray bottle, he may press the select button until the small LED lights up. Similarly, should the user wish to process a large water volume, such as a carafe, he may press the select button until the large LED lights. The small and large LEDs generally indicate which of the two operational modes is currently active. In the present embodiment, both the small and large LEDs are multicolor, capable of displaying either an amber or green hue. Again, alternate embodiments may employ different colors or color combinations without departing from the spirit or scope of the present invention.

Figure 38:
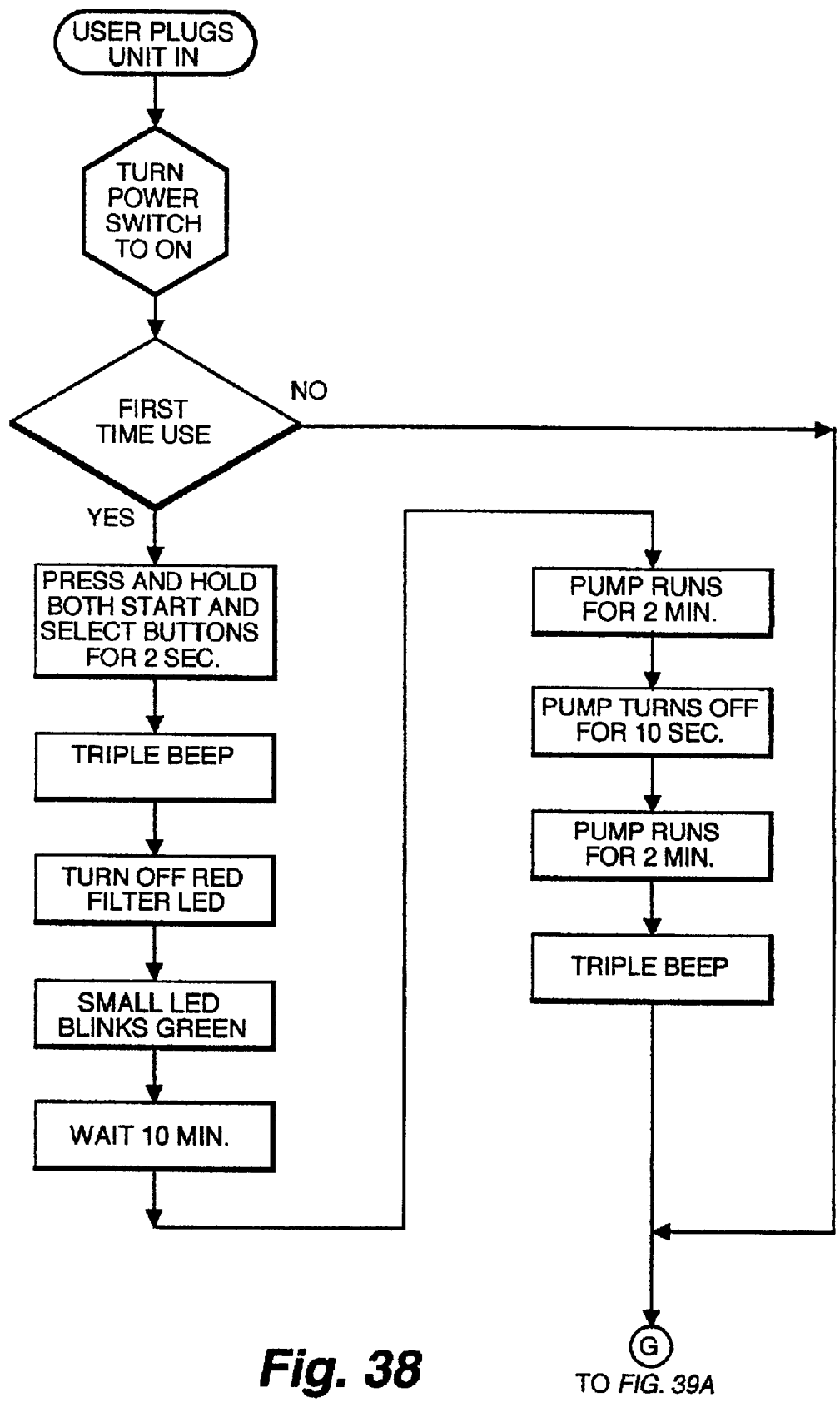
FIGS. 38–41 show the block diagram showing the operation steps used by the control unit in controlling the inventive device, correspond to the control panel overlays shown in FIGS. 36 and 37.

FIG. 38 is a flowchart displaying the control logic for an embodiment of the present invention. Initially, a user activates the device by plugging it into a standard 120 volt AC power socket and turning on the power switch. Once the device is powered, it determines whether the current activation is also the first activation. If so, then the device begins its prime mode by prompting (by the instruction manual, an audible tone, or a visual cue such as flashing lights) the user to press and hold both the start and select buttons for two seconds. Alternately, the user may perform this task without prompting. Once the buttons are pressed, the device emits a triple beep or other audible signal indicating that the user input was received, turns off the red filter LED, and sets the small LED to blink green. Following a ten minute wait, the pump runs for approximately two minutes then turns off for approximately ten seconds. After the ten second power down, the pump again runs for about two minutes. The device next emits another triple beep or audible signal, signifying the end of the prime mode.

Figure 39A:
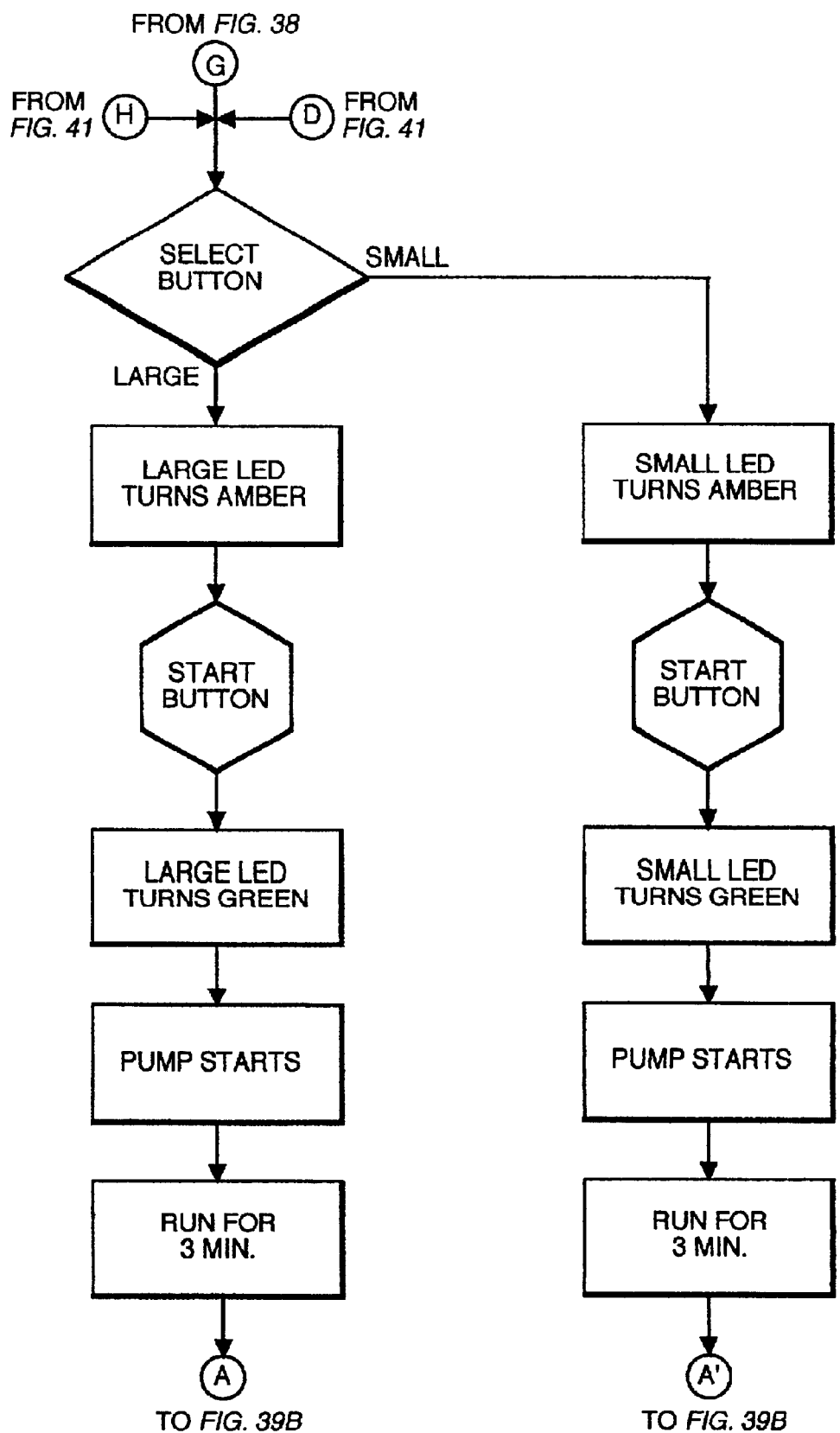
Figure 39B:
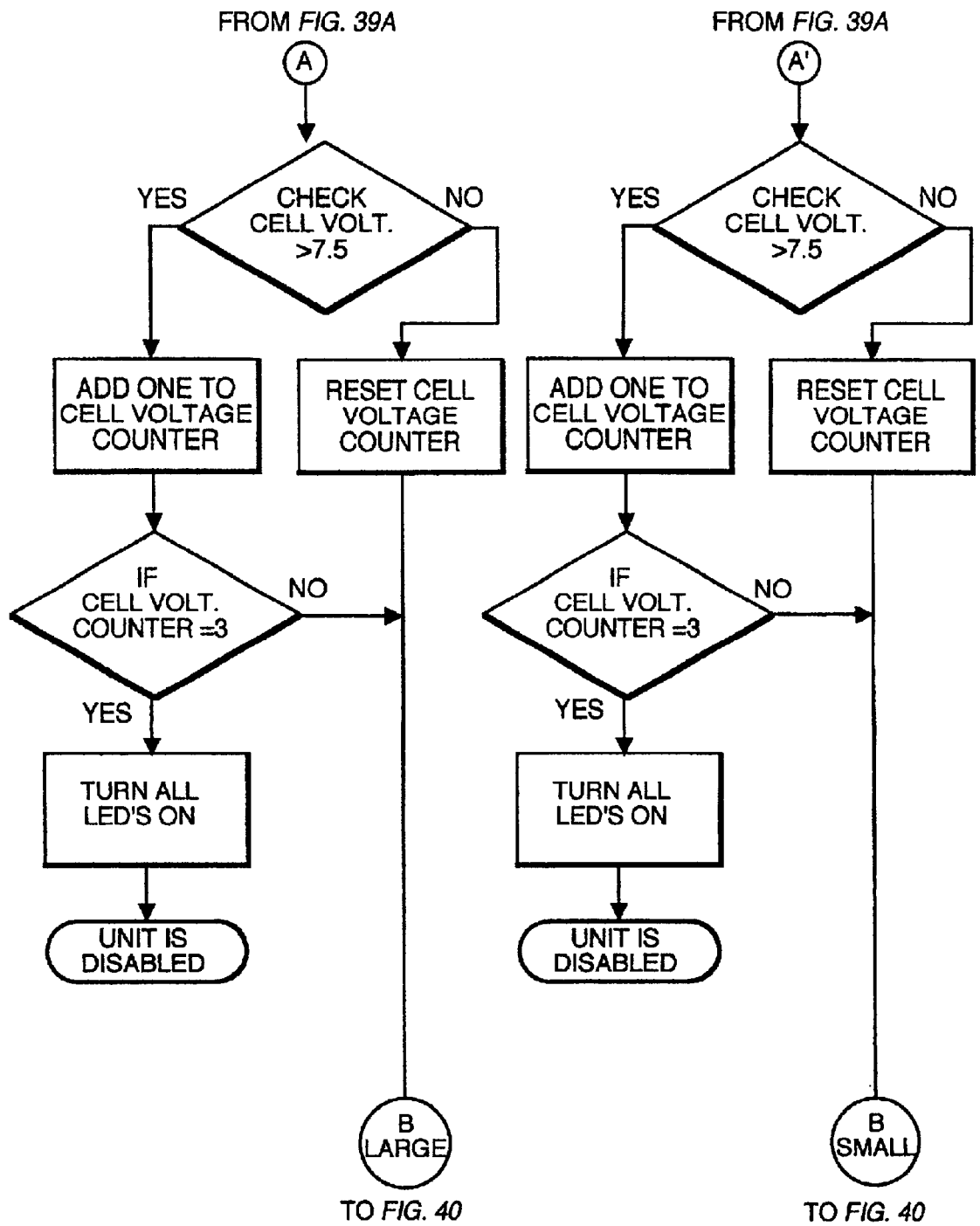

Once the prime mode is complete, or in the event that the device is not being activated for the first time, the control logic governing the water purification process is activated. FIG. 39 displays the initial steps of the control logic. First, the user selects whether the device will process a large or small volume of water. Generally, the small water volume corresponds to a spray bottle, while the large volume corresponds to a carafe. The user may press the select button to toggle between large and small settings. The device is in a ready state while awaiting this user input. Although not shown in FIG. 39, the user typically also fills the container corresponding to the water volume chosen and places it in a recess located on the base of the main housing.

If the large setting is selected, the large LED lights amber. Once the large LED is amber, the user may press the start button, which turns the large LED green and starts the pump. The pump runs for approximately three minutes, after which the device checks the cell voltage. If the cell voltage exceeds 7.5 volts, the cell voltage counter is incremented by one and the device determines whether the cell voltage counter is greater than three. If so, then the device turns on all LEDs to alert the user to a potential problem with the cell voltage and disables the device. The device should accordingly be sent to a qualified technician or vendor for maintenance. However, if the cell voltage counter is less than three, then the device increments filter counter three, as discussed in more detail below with respect to FIG. 40.

Figure 40:
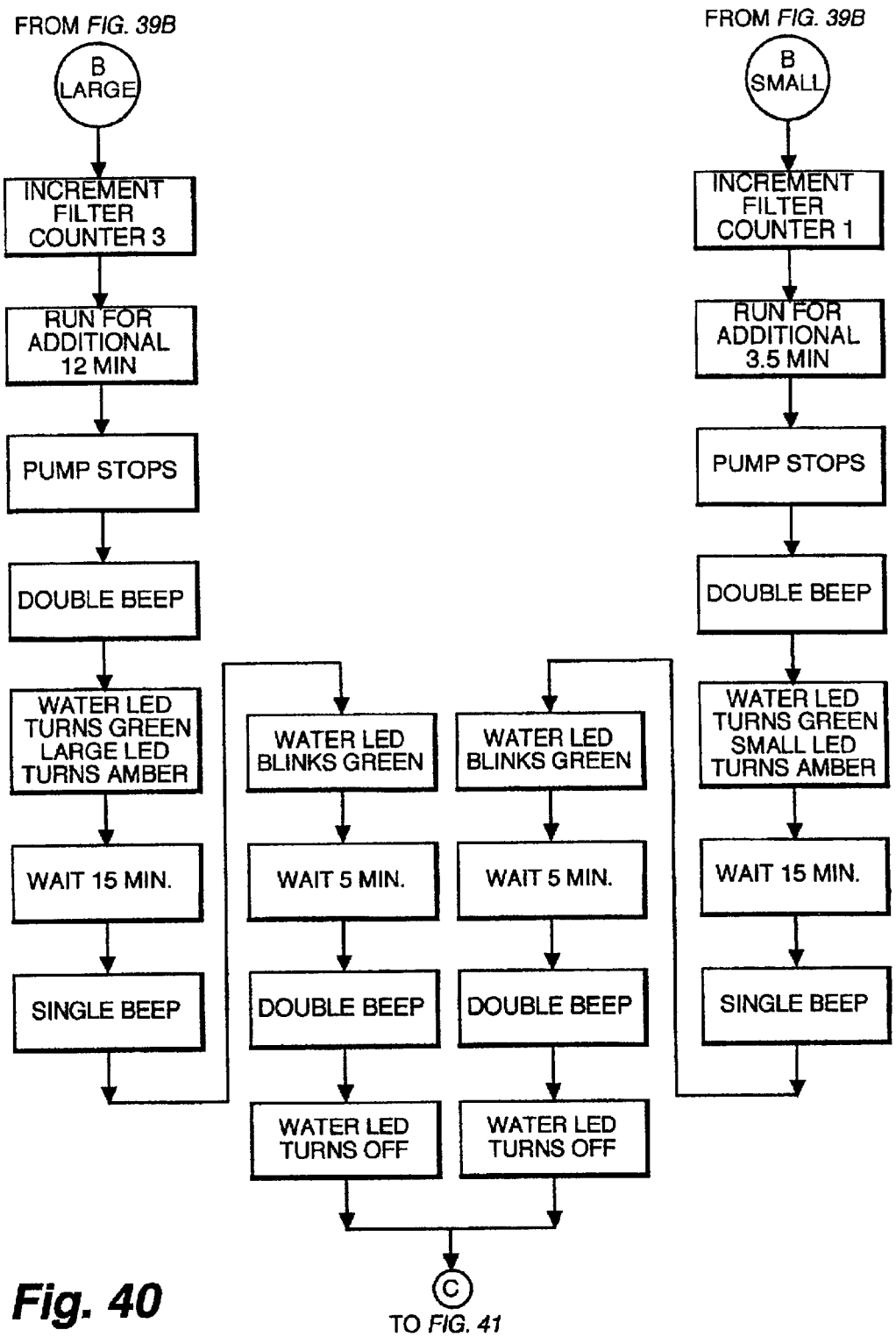

If the device determines that the cell voltage is less than 7.5 volts, it resets the cell voltage counter to zero. Next, the device increments filter counter three, as shown in FIG. 40. After incrementing filter counter three, the pump runs for about twelve minutes then stops. The device may then emit a double beep or other audible signal, indicating that the device is beginning the ozonation cycle. The double beep is accompanied by the water LED turning green and the large LED turning amber.

Following the LED color changes, the device pauses for approximately fifteen minutes, after which it emits a single beep or other audible signal. Additionally, the water LED blinks green. After another five minute pause, the device gives off a double beep or other tone and the water LED turns off, indicating that the ozonation cycle is complete.

The control logic for ozonation of a small volume of water is exactly the same as that set forth above, with the exception that large LED status changes are replaced by small LED status changes.

Figure 41:
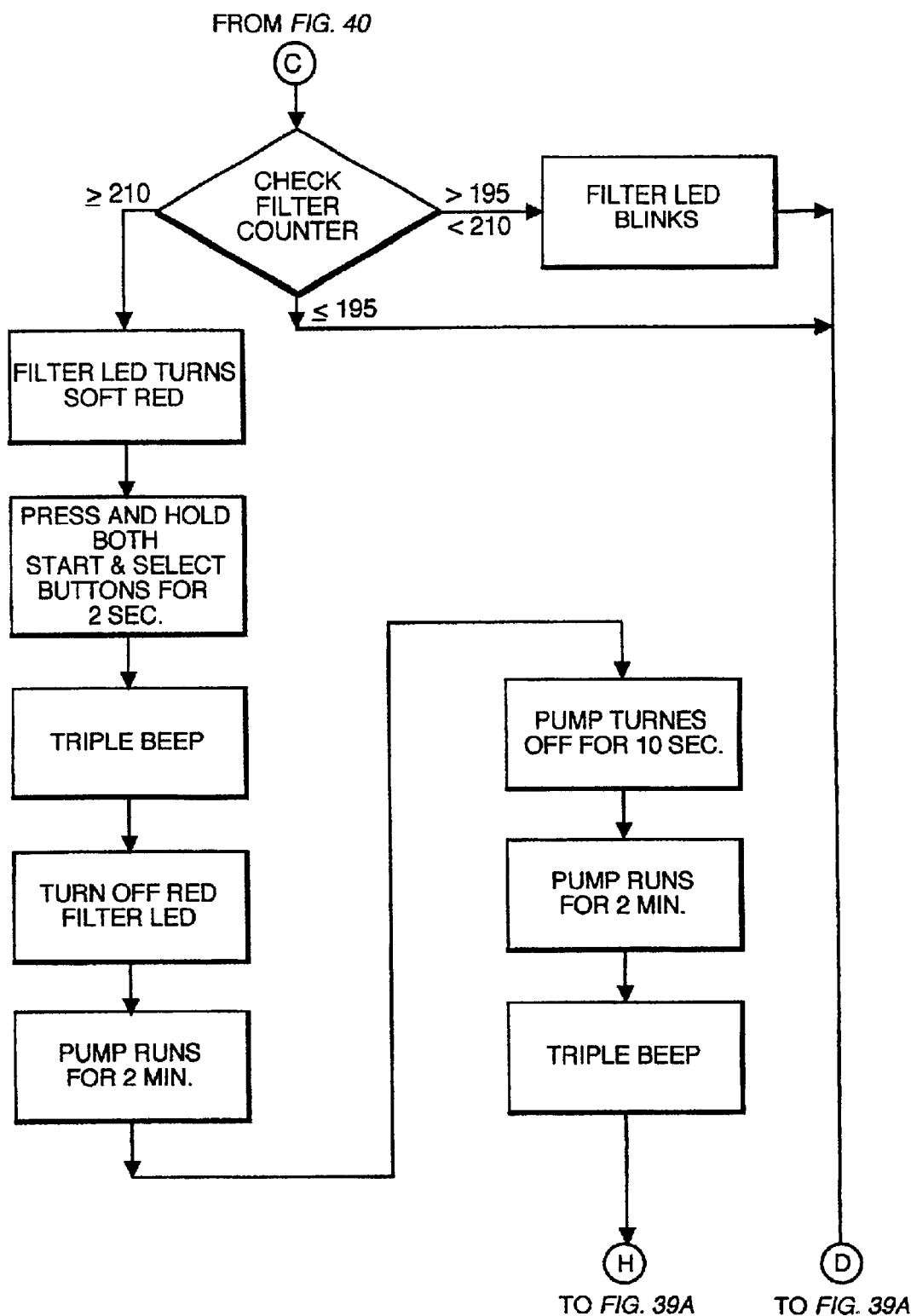

Once the ozonation cycle finishes for either water volume, the device checks the status of the filter counter, as shown in FIG. 41. If the filter counter is below 195, then the filter quality is still acceptable and the control logic returns to its ready state shown in FIG. 37, wherein it waits for the user to initiate the ozonation process by pressing the select button. Should the filter counter be between 195 and 210, the filter LED blinks, indicating that the filter will need replacing shortly. After this, the device returns to its ready state.

Should the filter counter be above 210, the filter LED turns solid red, indicating that the user should change the filter. The user may either change the filter or ignore the suggestion. Either way, the device prompts the user to press and hold both the start and select buttons for two seconds, or the user may press both buttons without any prompt. Once the device receives this user input, it emits a triple beep or other audible cue and extinguishes the red filter LED. The pump then runs for approximately two minutes, after which the pump turns off for ten seconds. This pause is followed by another two minutes of pump activation. Finally, the device emits another triple beep, indicating that the filter has been successfully changed. The device then returns to the ready state, as discussed above.

Although the present invention has been described with a certain degree of particularity, it is understood that the present disclosure has been made by way of example, and changes in detail or structure may be made without departing from the spirit of the invention as defined in the appended claims.

What is claimed is:

1. A cleaning apparatus comprising:
a reservoir containing a liquid, said reservoir able to be easily manipulated by a user to dispense said liquid;
a device for increasing the level of oxidative properties in said liquid;
a circulation flow path communicating with said reservoir and said device to allow at least some of said liquid in said reservoir to flow from said reservoir to said device and back to said reservoir;
wherein said circulation flow path includes a recirculation flow path and a treatment flow path, where said treatment flow path directs water from said recirculation flow path to said device and back to said recirculation flow path; and
wherein said treatment flow path includes a pre-treatment region upstream of said device and downstream of a diversion of said treatment flow path from said recirculation flow path.

2. An apparatus as defined in claim 1, wherein said pre-treatment region is a deionization resin bed.

3. A cleaning apparatus comprising:
a spray bottle containing a liquid, said spray bottle able to be easily manipulated by a user to dispense said liquid;
a device for increasing the level of oxidative properties in said liquid;
a circulation flow path communicating with said spray bottle and said device to allow at least some of said liquid in said spray bottle to flow from said spray bottle to said device and back to said spray bottle.

4. A cleaning apparatus comprising:
a carafe containing a liquid, said carafe able to be easily manipulated by a user to dispense said liquid;
a device for increasing the level of oxidative properties in said liquid;
a circulation flow path communicating with said carafe and said device to allow at least some of said liquid in said carafe to flow from said carafe to said device and back to said carafe.

5. A cleaning apparatus comprising:
a reservoir containing a liquid, said reservoir able to be easily manipulated by a user to dispense said liquid;
a device for increasing the level of oxidative properties in said liquid;
a circulation flow path communicating with said reservoir and said device to allow at least some of said liquid in said reservoir to flow from said reservoir to said device and back to said reservoir;
wherein said circulation flow path includes a recirculation flow path and a treatment flow path, where said treatment flow path directs water from said recirculation flow path to said device and back to said recirculation flow path; and
wherein said treatment flow path includes a pre-treatment region downstream of said device and upstream of a reconvergence of said treatment flow path and said recirculation flow path.

6. An apparatus as defined in claim 5, wherein said post-treatment region is a lead abatement filter.

7. A residential cleaning apparatus comprising:
a base unit including an ozone generator;
a reservoir for holding water and for use by a user to selectively dispense water, said reservoir being selectively and fluidically attachable to said base unit;
a circulation flow path formed between said reservoir and said base unit, and fluidically and at least in part connecting said reservoir with said ozone generator; and
wherein said at least some of said water flows in said circulation flow path between said reservoir and said ozone generator and back to said reservoir, said ozone generator dispensing ozone into said water.

8. An apparatus as defined in claim 7, wherein:
said circulation flow path includes a recirculation flow path and a treatment flow path, said recirculation flow path extending between said reservoir, said base, and back to said reservoir, and said treatment flow path extending from said recirculation flow path to said ozone generator and back to said recirculation flow path; and
wherein said ozone generator dispenses ozone into said water in said treatment flow path.

9. An apparatus as defined in claim 8, wherein:
said treatment flow path includes a deionization filter media positioned upstream of said ozone generator.

10. An apparatus as defined in claim 9, wherein said deionization filter media is positioned in said base unit.

11. An apparatus as defined in claim 9, further comprising:
a cartridge selectively and fluidically connectable to said base unit, and forming part of said treatment flow path; and wherein said deionization filter media is positioned in said cartridge.

12. An apparatus as defined in claim 8, further comprising:
a mixing device connected between said treatment flow path and said recirculation flow path, said mixing device to help mix the treated water in the treatment flow path with the untreated water in the recirculation flow path.

13. An apparatus as defined in claim 12, wherein:
said mixing device is a venturi.

14. An apparatus as defined in claim 8, wherein:
a pump is positioned in said circulation flow path to assist in moving said water along said circulation flow path.

15. An apparatus as defined in claim 7, wherein:
said base unit is positionable on a support surface.

16. An apparatus as defined in claim 7, wherein:
said base unit is built into a household appliance.

17. An apparatus as defined in claim 7, wherein:
said reservoir is a spray bottle.

* * * * *